US012680109B2

(12) United States Patent
Shaw et al.

(10) Patent No.: US 12,680,109 B2
(45) Date of Patent: Jul. 14, 2026

(54) AAV VECTOR FOR NEURONAL EXPRESSION OF PROGRANULIN

(71) Applicant: King's College London, London (GB)

(72) Inventors: Christopher Edward Dennistoun Shaw, London (GB); Youn Bok Lee, London (GB)

(73) Assignee: King's College London, London (GB)

( * ) Notice: Subject to any disclaimer, the term of this patent is extended or adjusted under 35 U.S.C. 154(b) by 1044 days.

(21) Appl. No.: 17/763,644

(22) PCT Filed: Sep. 28, 2020

(86) PCT No.: PCT/EP2020/077144
§ 371 (c)(1),
(2) Date: Mar. 24, 2022

(87) PCT Pub. No.: WO2021/058830
PCT Pub. Date: Apr. 1, 2021

(65) Prior Publication Data
US 2022/0380804 A1      Dec. 1, 2022

(30) Foreign Application Priority Data

Sep. 27, 2019    (GB) ..................................... 1913974

(51) Int. Cl.
*C12N 15/86*          (2006.01)

(52) U.S. Cl.
CPC .... *C12N 15/86* (2013.01); *C12N 2750/14143* (2013.01); *C12N 2800/22* (2013.01); *C12N 2830/008* (2013.01); *C12N 2830/42* (2013.01)

(58) Field of Classification Search
None
See application file for complete search history.

(56) References Cited

U.S. PATENT DOCUMENTS

| | | | | |
|---|---|---|---|---|
| 2003/0152560 A1* | 8/2003 | Selden | ................. | C12N 9/2465 435/208 |
| 2020/0071680 A1* | 3/2020 | Abeliovich | .............. | C12N 7/00 |
| 2020/0397917 A1 | 12/2020 | Tagliatela et al. | | |

FOREIGN PATENT DOCUMENTS

| | | | | |
|---|---|---|---|---|
| TW | 201925474 A | 7/2019 | | |
| WO | 2008019187 A2 | 2/2008 | | |
| WO | WO-2012/145646 A1 | 10/2012 | | |
| WO | 2016115503 A1 | 7/2016 | | |
| WO | WO-2017151884 A1 * | 9/2017 | .............. | A61P 43/00 |
| WO | WO-2020/172490 A1 | 8/2020 | | |
| WO | WO-2020191212 A1 * | 9/2020 | .......... | C12Q 1/6811 |
| WO | WO-2021/016505 A1 | 1/2021 | | |
| WO | WO-2021/058830 A1 | 4/2021 | | |

OTHER PUBLICATIONS

Mignone, et al. Untranslated regions of mRNAs. Genome Biology. Feb. 2002;3(3):1-10. (Year: 2002).*
Holler, et al. Intracellular proteolysis of progranulin generates stable, lysosomal granulins that are haploinsufficient in patients with Frontotemporal Dementia caused by GRN mutations. eNeuro. Jul./Aug. 2017;4(4):1-22. (Year: 2017).*
Benjamin E. Deverman, et al., Gene therapy for neurological disorders: progress and prospects, Nature Reviews Drug Discovery, Aug. 10, 2018, pp. 641-659, vol. 17, No. 9.
Ted Choi, et al., A generic intron increases gene expression in transgenic mice, Molecular and Cellular Biology, Jun. 1991, pp. 3070-3074, vol. 11, No. 6.
Alan B. Rose, Introns as gene regulators: a brick on the accelerator, Frontiers in Genetics, Feb. 7, 2019, article 672, vol. 9.
Kells et al., "Efficient gene therapy-based method for the delivery of therapeutics to primate cortex," PNAS. 106 (7): 2407-2411 (2009).
Green et al. "Axonal transport of AAV9 in nonhuman primate brain," PMC. 23(6): 520-526 (2016) (14 pages).
Naidoo et al. "Extensive Transduction and Enhanced Spread of a Modified AAV2 Capsid in the Non-human Primate CNS," Molecular Therapy. 26(10): 2418-2430 (2018).
Gilkes et al. "Preferred transduction with AAV8 and AAV9 via thalamic administration in the MPS IIIB model: A comparison of four rAAV serotypes," Elsevier Inc. 48-54 (2016).
Yazdan-Shahmorad et al. "Widespread optogenetic expression in macaque cortex obtained with MR-guided, convection enhanced delivery (CED) of AAV vector to the thalamus," Elsevier B.V. 347-358 (2018).
Colle et al. "Efficient intracerebral delivery of AAV5 vector encoding human ARSA in non-human primate," Human Molecular Genetics. 19(1): 147-158 (2010).
Rockwell et al. "AAV-Mediated Gene Delivery in a Feline Model of Sandhoff Disease Corrects Lysosomal Storage in the Central Nervous System," ASN Neuro. 1-13 (2015).
Golebiowski et al. "Direct Intracranial Injection of AAVrh8 Encoding Monkey ß-N-Acetylhexosaminidase Causes Neurotoxicity in the Primate Brain," Human Gene Therapy. 28(6): 510-522 (2017).
Sevin et al. "Intracerebral adeno-associated virus-mediated gene transfer in rapidly progressive forms of metachromatic leukodystrophy," Human Molecular Genetics. 15(1): 53-64 (2006).
(Continued)

*Primary Examiner* — Allison M Fox
*Assistant Examiner* — Gina Pronzati
(74) *Attorney, Agent, or Firm* — Clark & Elbing LLP

(57) ABSTRACT

The present invention relates to the field of recombinant viral vectors suitable for the delivery of therapeutic genes in vivo. Described is an adeno-associated virus (AAV) vector comprising (i) a human growth hormone intron 3 (hGHi3) sequence (ii) a synapsin promoter sequence and/or (iii) a progranulin 3' untranslated region (UTR) sequence, operably coupled to a polynucleotide sequence encoding a polypeptide of interest. Specific use of such a vector lies in the enhanced expression of a polypeptide of interest, such as progranulin (PGRN), to treat subjects who have a genetic mutation or intrinsic polypeptide level that is below a physiologically normal level.

13 Claims, 22 Drawing Sheets

Specification includes a Sequence Listing.

(56) References Cited

OTHER PUBLICATIONS

Cataltepe et al., "Surgical Technique for Bilateral Intrathalamic Infusion of rAAVrh8-HEXA/HEXB Gene Therapy in Infant With Tay-Sachs Disease," Mol Ther. 28(4):295-296 (Apr. 2020).

International Search Report and Written Opinion for PCT/EP2022/072487, dated Feb. 13, 2023 (22 pages).

* cited by examiner b)

c)

| Human | | | | Other species | | | | | |
|---|---|---|---|---|---|---|---|---|---|
| After | | Before | | After | | Before | | | |
| CAI | GC | CAI | GC | CAI | GC | CAI | GC | | |
| 0.92 | 61.08 | 0.83 | 63.23 | 0.93 | 61.08 | 0.82 | 63.28 | *Pongo pygmaeus* | 1 |
| 0.91 | 61.13 | 0.83 | 63.23 | 0.91 | 61.08 | 0.82 | 63.28 | *Gorilla gorilla* | 2 |
| 0.92 | 62.91 | 0.83 | 63.23 | 0.9 | 62.91 | 0.8 | 63.28 | *Pan troglodytes* | 3 |
| 0.95 | 66.27 | 0.83 | 63.23 | 0.89 | 66.27 | 0.75 | 63.23 | *Oryctolagus cuniculus* | 4 |
| 0.92 | 61.96 | 0.83 | 63.23 | 0.93 | 61.96 | 0.83 | 63.23 | *Rattus norvegicus* | 5 |
| 0.93 | 63.1 | 0.83 | 63.23 | 0.9 | 63.1 | 0.81 | 63.23 | *Canis familiaris* | 6 |
| 0.93 | 63.06 | 0.83 | 63.23 | 0.89 | 63.06 | 0.8 | 63.23 | *Bos taurus* | 7 |
| 0.93 | 62.4 | 0.83 | 63.23 | 0.91 | 62.4 | 0.79 | 63.23 | *Capra hircus* | 8 |
| 0.91 | 63.65 | 0.83 | 63.23 | 0.93 | 63.65 | 0.78 | 63.23 | *Ovis aries* | 9 |
| 0.93 | 62.4 | 0.83 | 63.23 | 9 | 62.4 | 0.8 | 63.23 | *Felis catus* | 10 |
| 0.93 | 65.69 | 0.83 | 63.23 | 0.91 | 65.69 | 0.79 | 63.23 | *Pig* | 11 |
| 0.92 | 61.87 | 0.83 | 63.23 | 0.94 | 61.87 | 0.84 | 63.23 | *Mouse* | 12 | a)
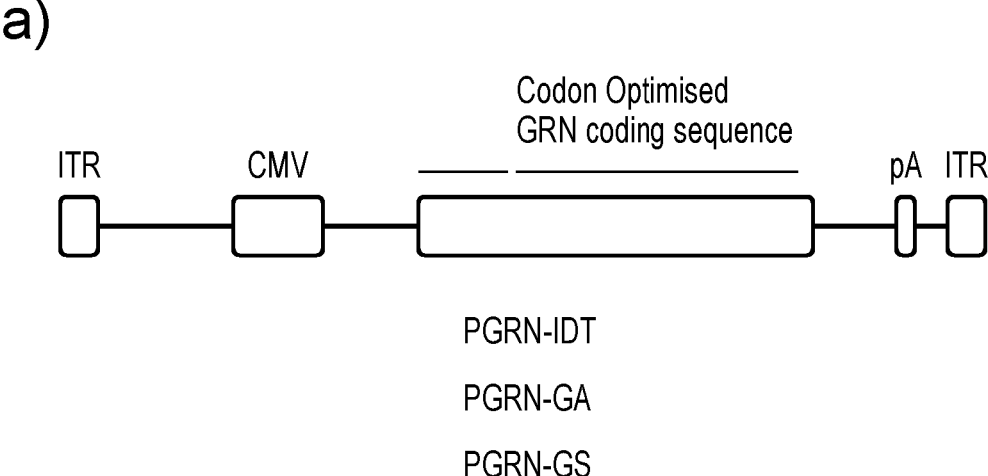
Codon Optimised
GRN coding sequence
ITR    CMV    pA  ITR
PGRN-IDT
PGRN-GA
PGRN-GS
b)
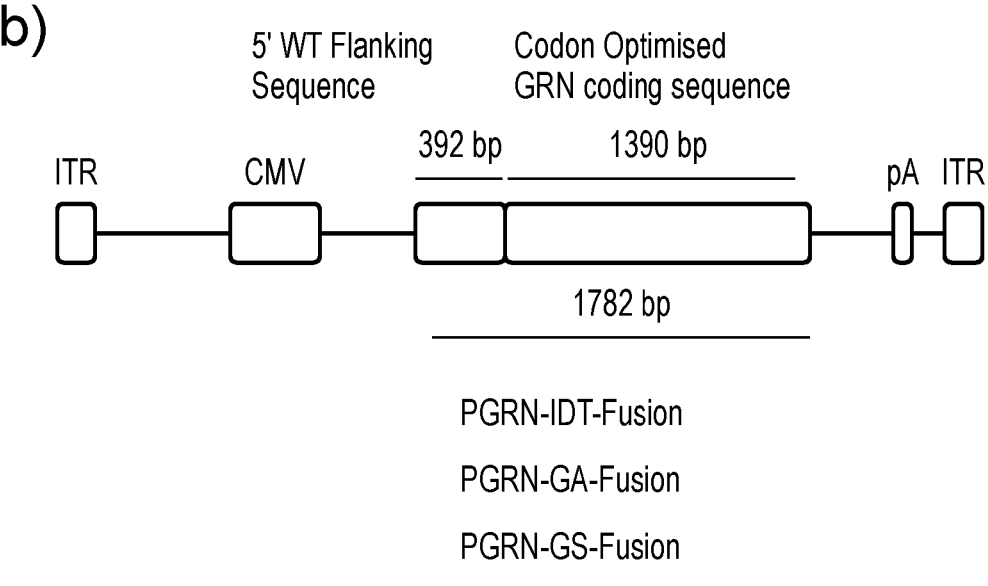
5' WT Flanking
Sequence
Codon Optimised
GRN coding sequence
ITR    CMV    392 bp    1390 bp    pA  ITR
1782 bp
PGRN-IDT-Fusion
PGRN-GA-Fusion
PGRN-GS-Fusion
FIG. 2 a)
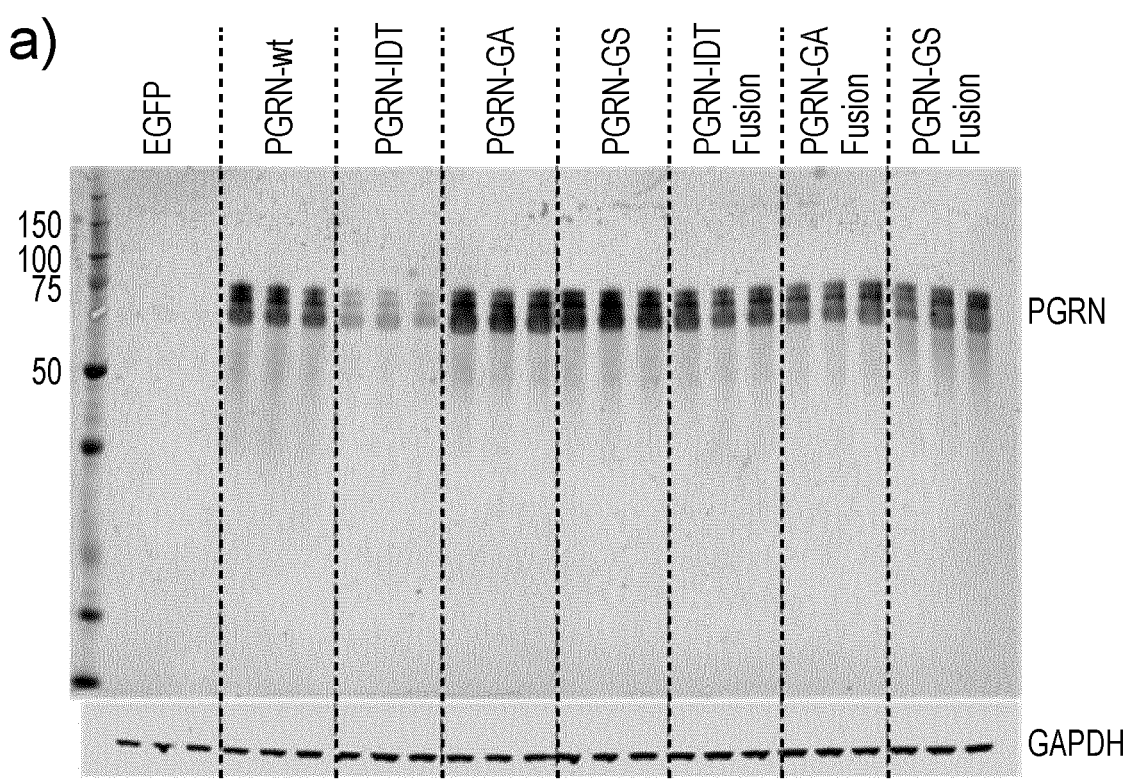
b)
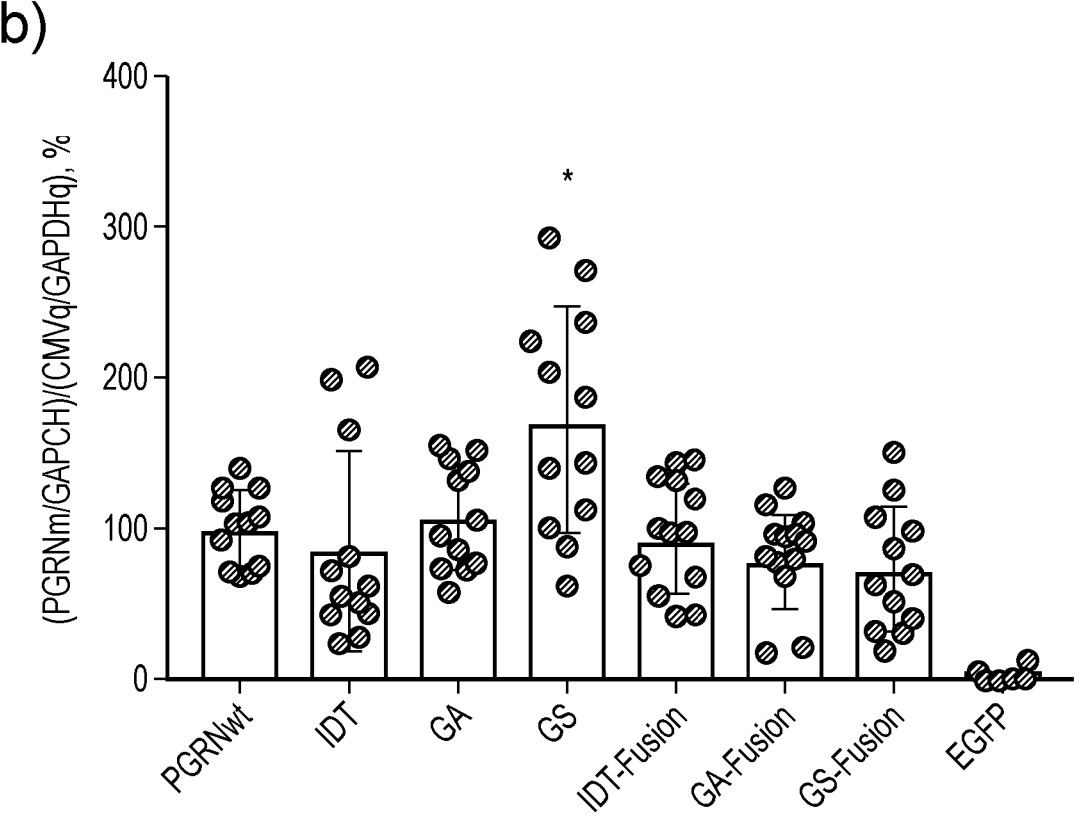
FIG. 3 a)
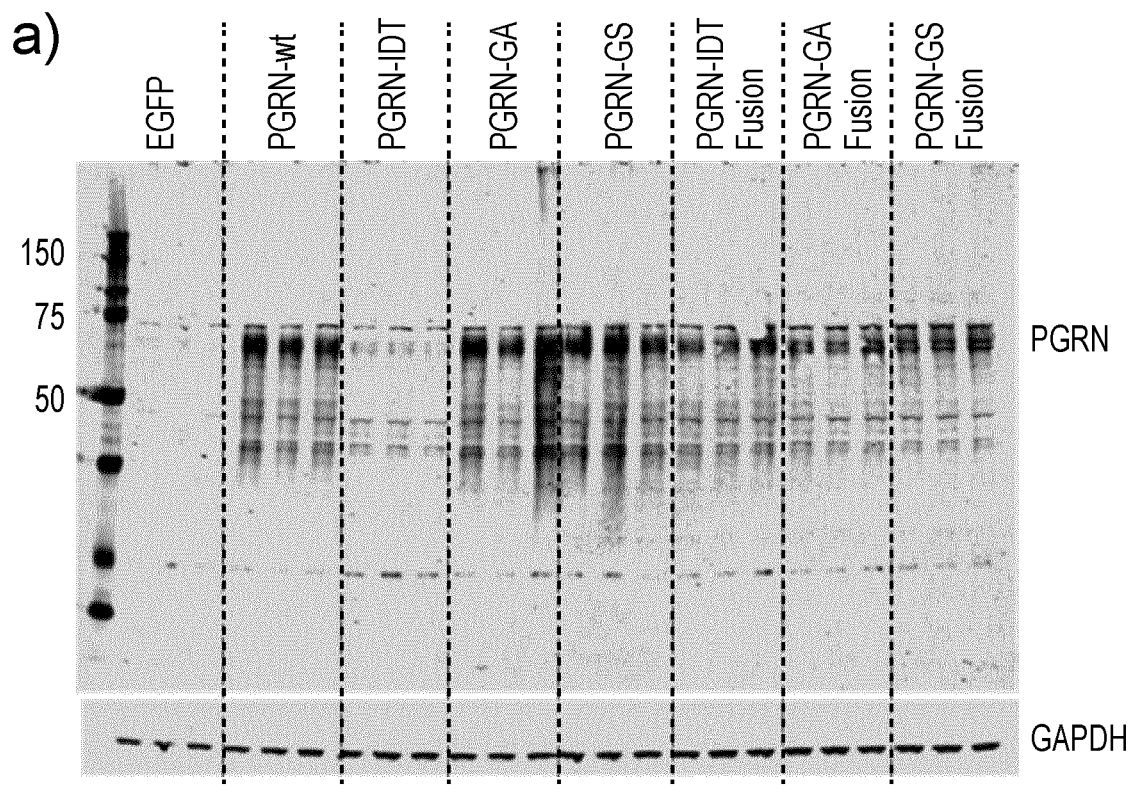
b)
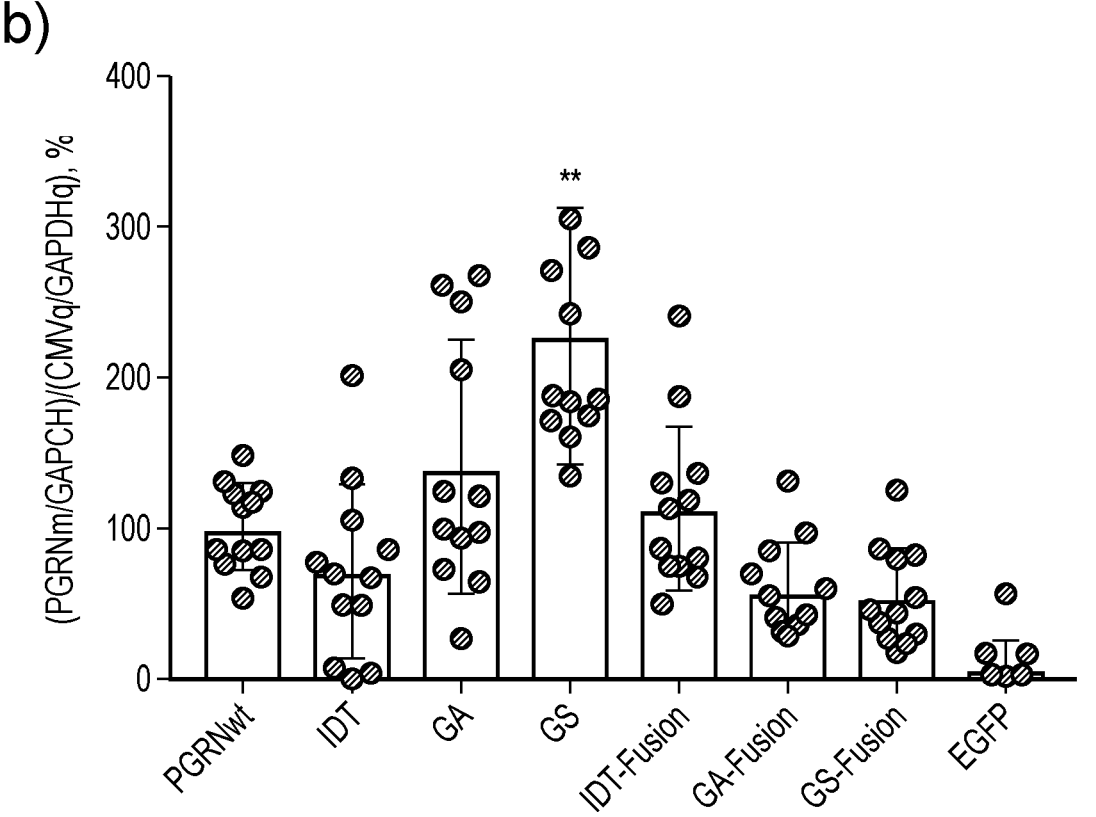
FIG. 4 a)
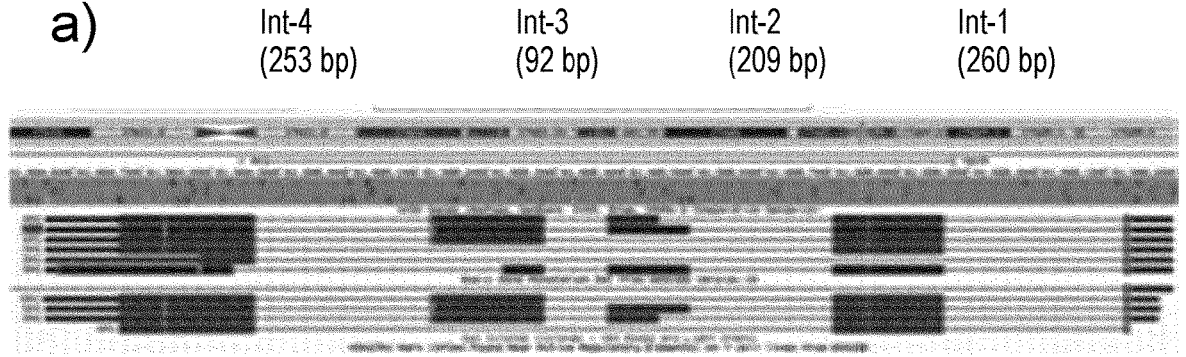
b)
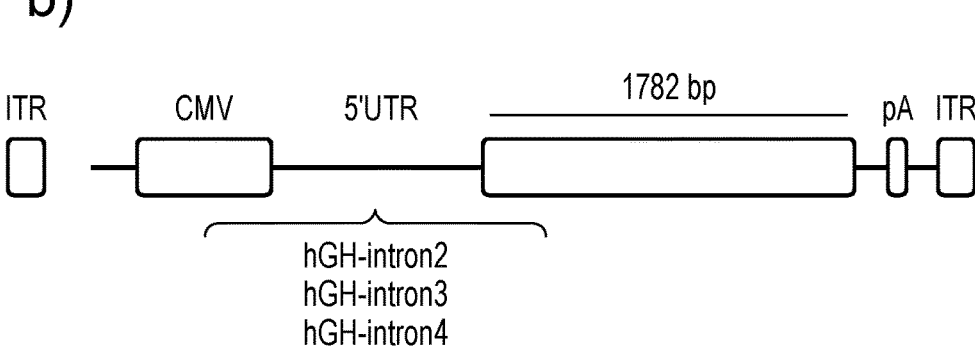
c)
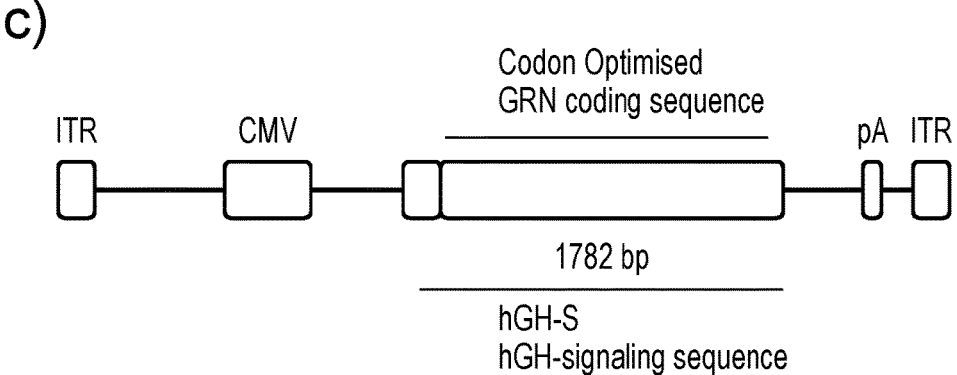
FIG. 5 a)
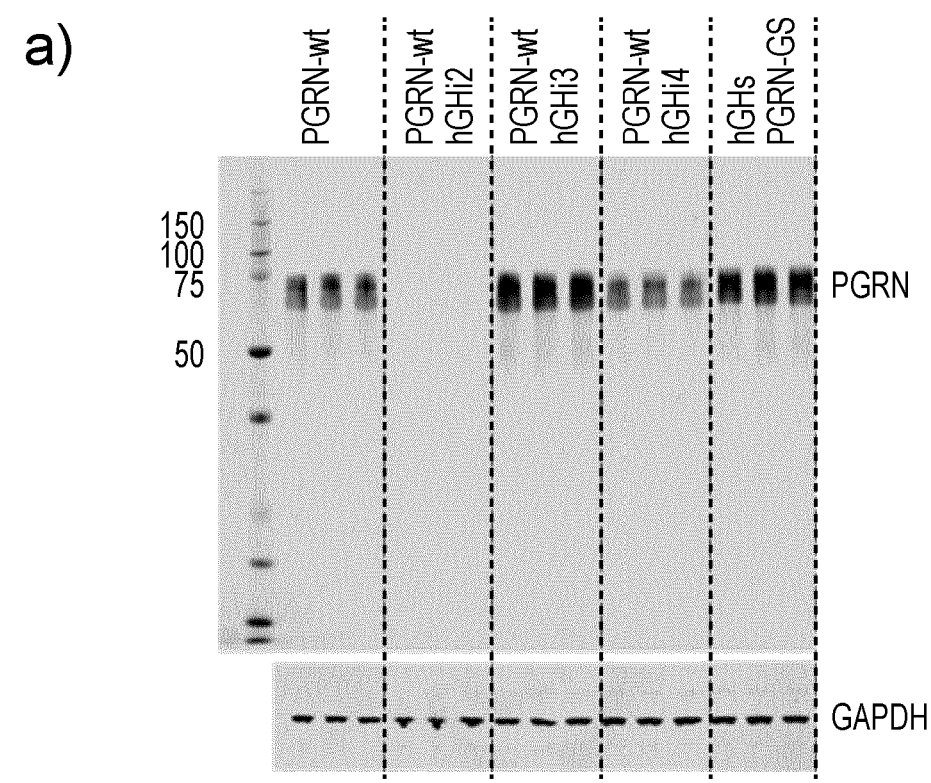
b)
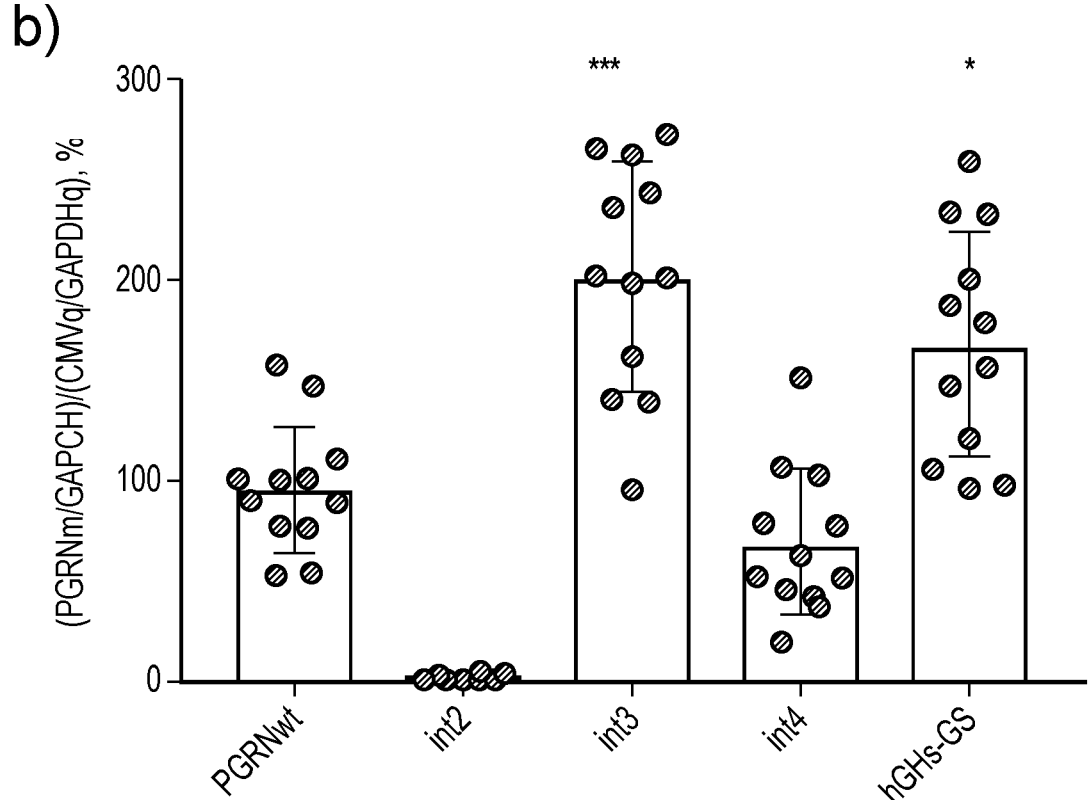
FIG. 6 a)
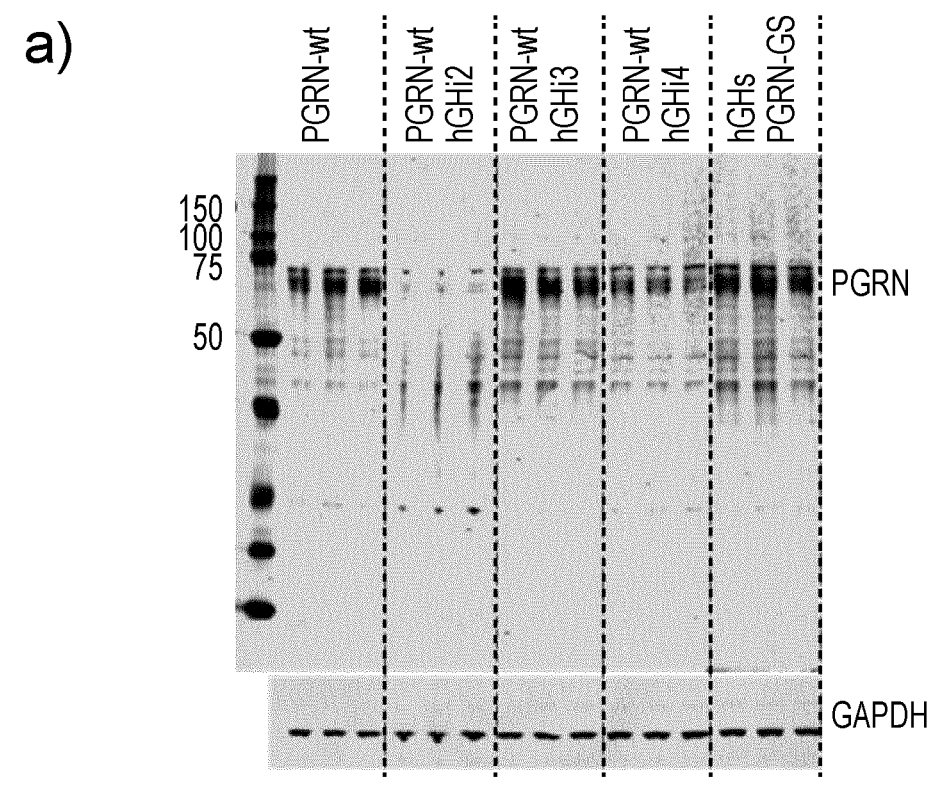
b)
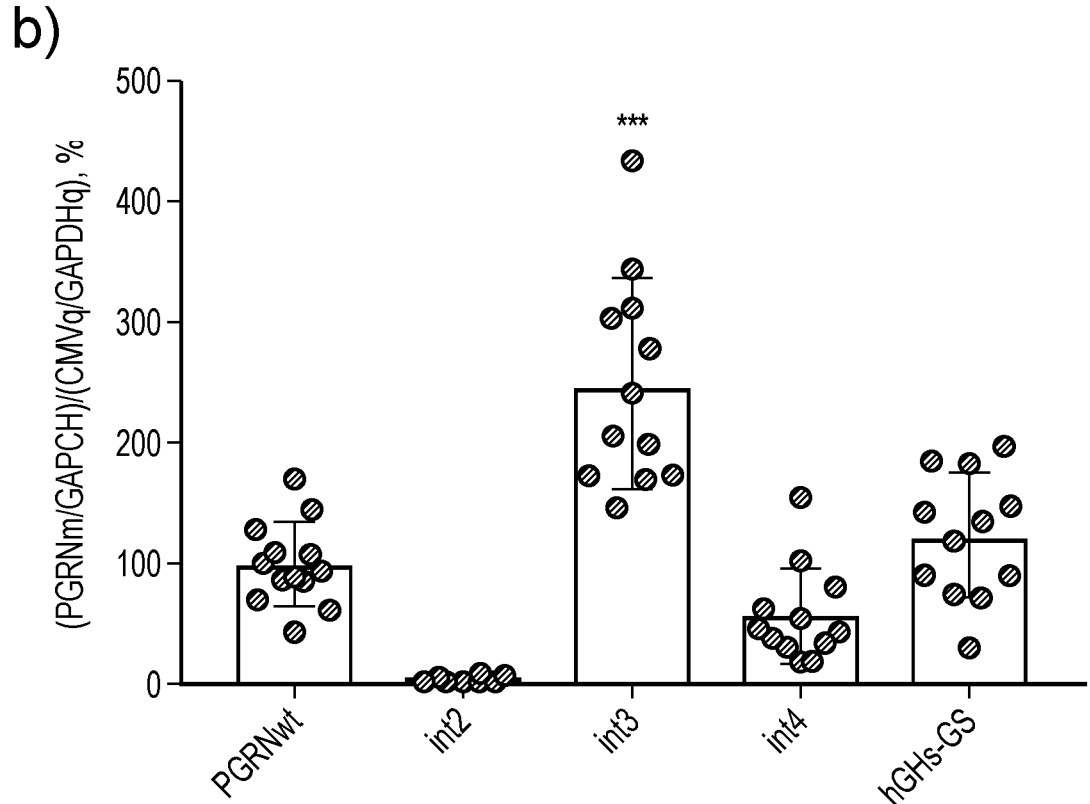
FIG. 7 a)
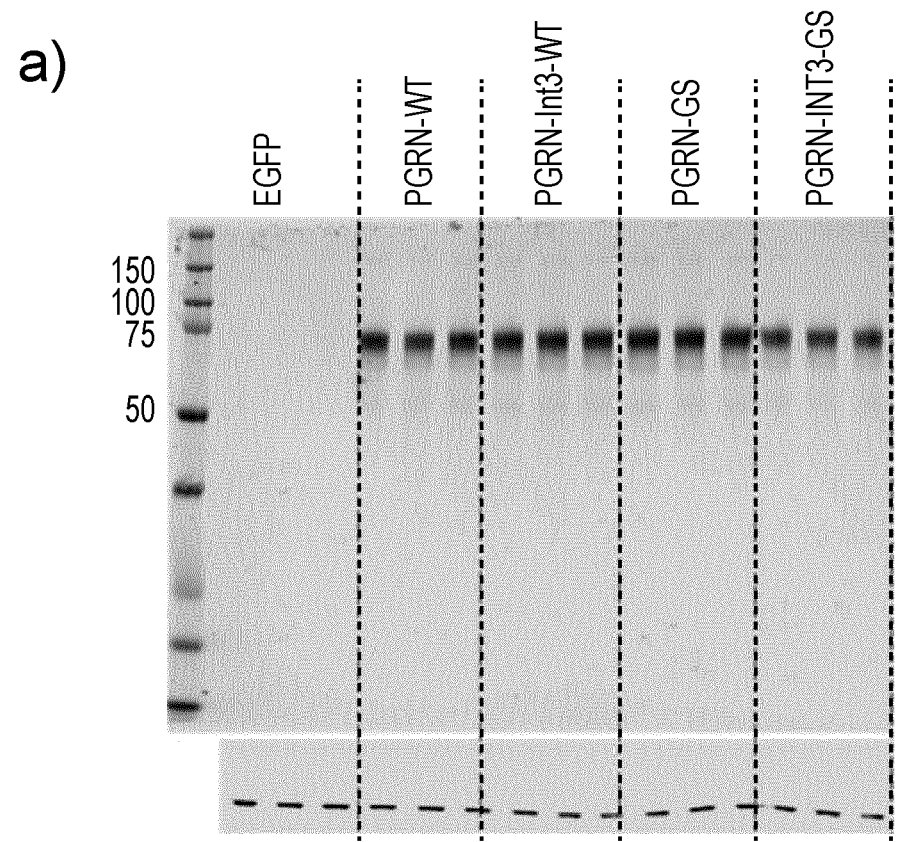
b)
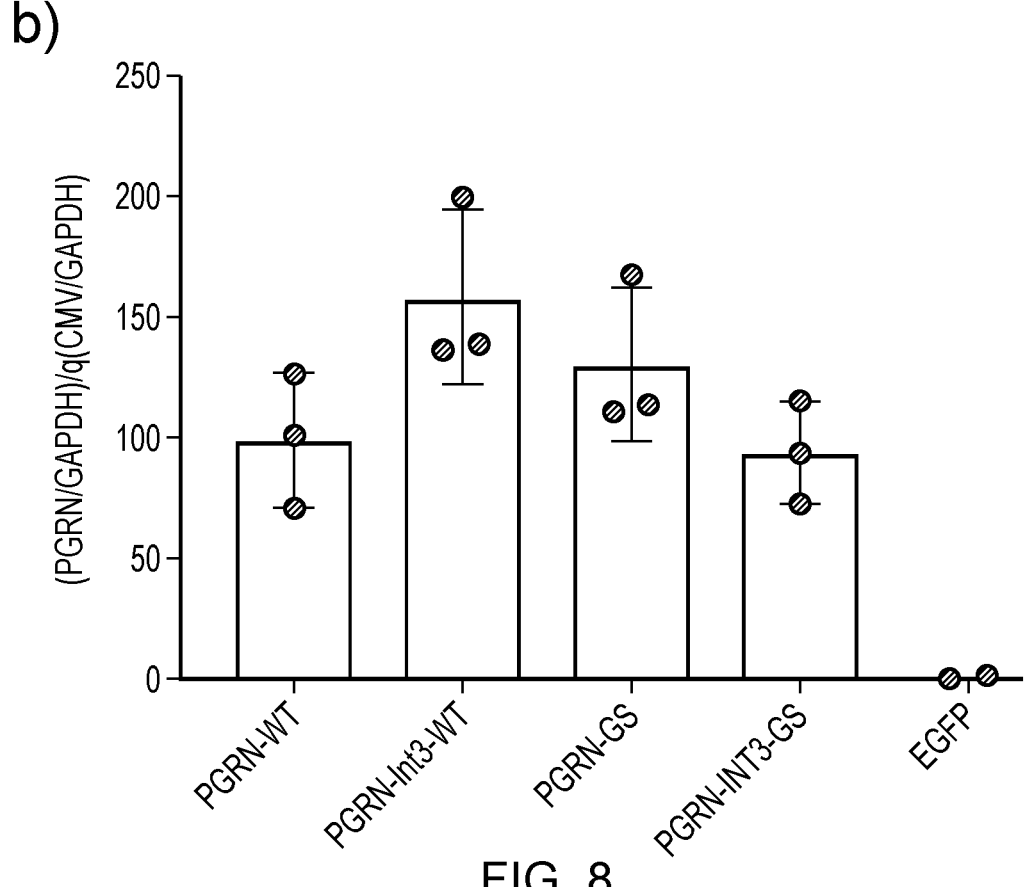
FIG. 8 a)
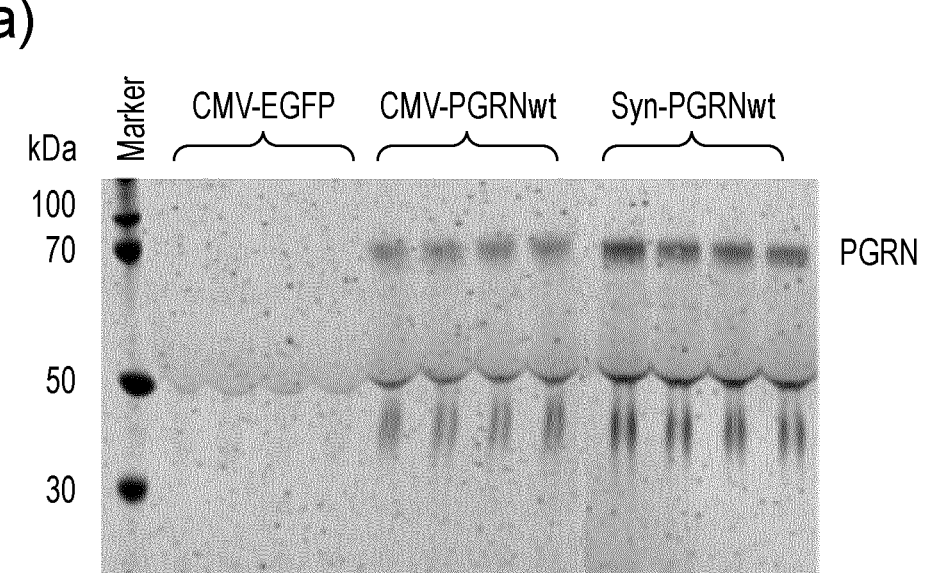
b)
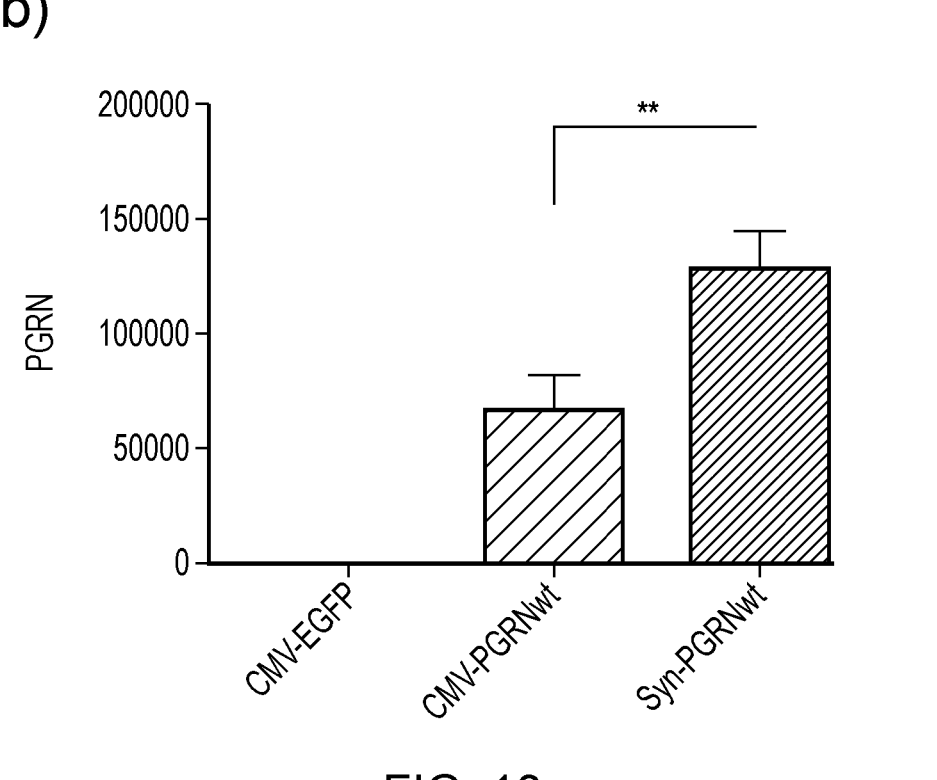
FIG. 10

A
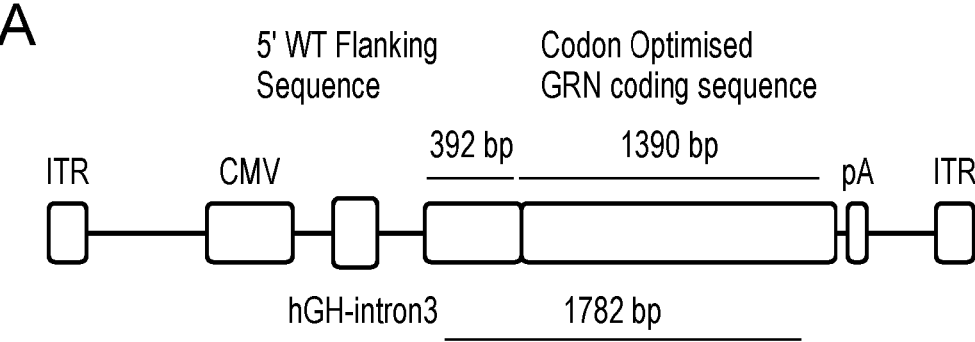
B
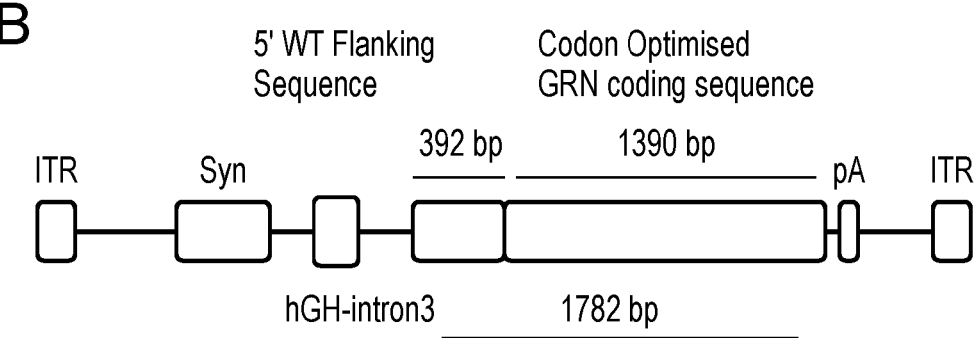
FIG. 14 a)
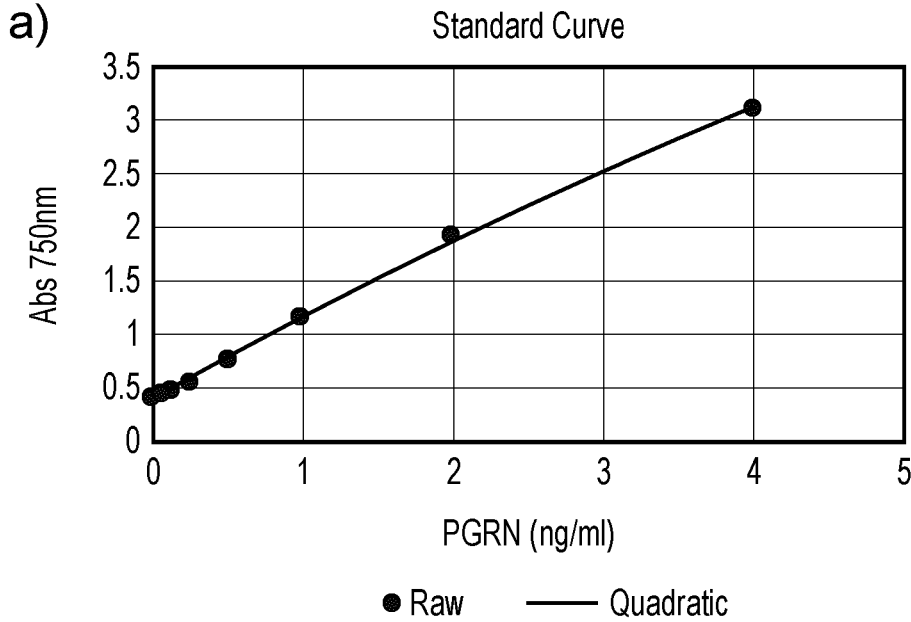
b)
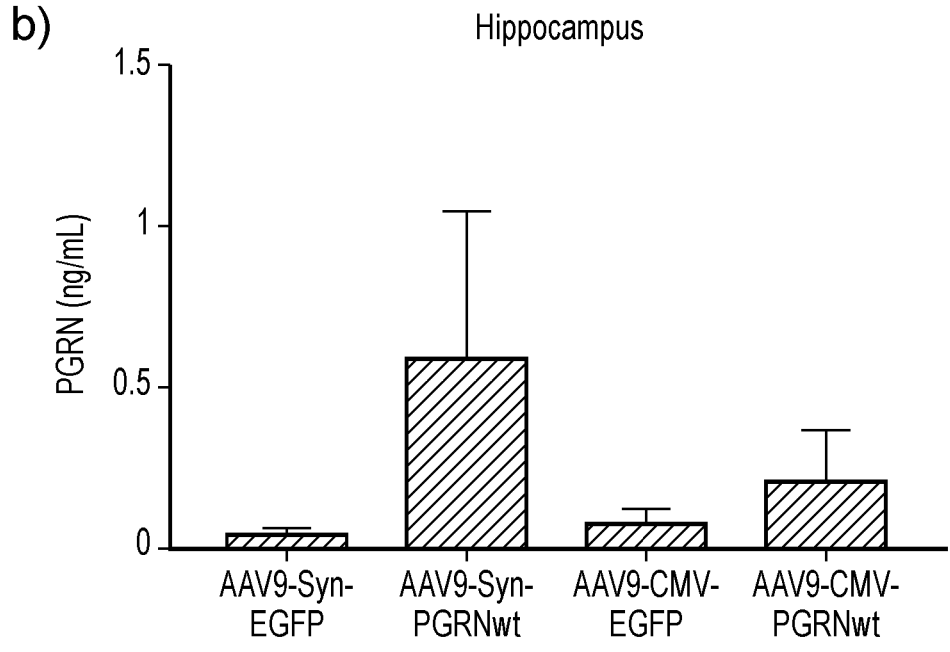
FIG. 16 a)

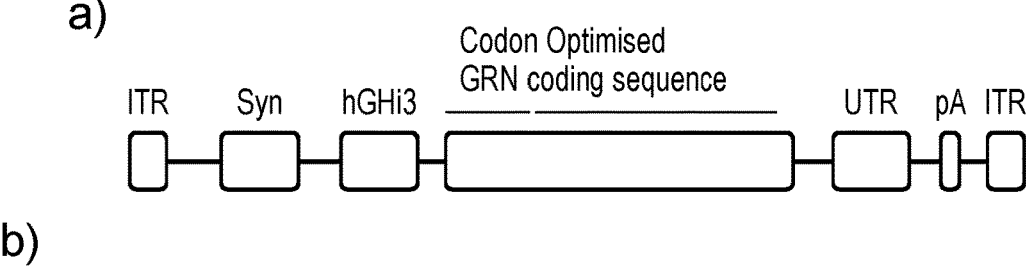

b)

Human PGRN-UTR sequence:

GGGACAGTACTGAAGACTCTGCAGCCCTCGGGACCCCACTCGGAGGGTGCCCTCTGC
TCAGGCCTCCCTAGCACCTCCCCCTAACCAAATTCTCCCTGGACCCCATTCTGAGCT
CCCCATCACCATGGGAGGTGGGGCCTCAATCTAAGGCCTTCCCTGTCAGAAGGGGGT
TGTGGCAAAAGCCACATTACAAGCTGCCATCCCCTCCCCGTTTCAGTGGACCCTGTG
GCCAGGTGCTTTTCCCTATCCACAGGGGTGTTTGTGTGTGTGCGCGTGTGCGTTTC

FIG. 17 a)

Standard Curve (Non-linear Fit)

AAV2 ITR    hGHi3    hPGRN-3'UTR    AAV2 ITR

PGRN-GS    f1 ori    KanR    ori hSyn promoter    bGH poly(A) signal

B)

ori

AAV2 ITR hSyn promoter hGHi3

KanR pAV-Syn-hGHi3-hPGRN-GS-UTR
5946 bp

PGRN-GS f1 ori bGH poly(A) signal

AAV2 ITR hPGRN-3'UTR

AAV VECTOR FOR NEURONAL EXPRESSION OF PROGRANULIN

FIELD OF THE INVENTION

The present invention relates to the field of recombinant viral vectors. In particular, the invention relates to recombinant viral vectors which are suitable for the delivery of therapeutic genes in vivo.

BACKGROUND TO THE INVENTION

Frontotemporal dementia (FTD) is the second most common form of dementia in people who present with symptoms <65 years of age. It is characterised by changes in behaviour, personality and language and is very distressing to the patient, their family and friends. Approximately 30% of patients with FTD have a family history of dementia and, of these ~20% carry loss of function (LoF) mutations in GRNgene encoding the protein progranulin. Children homozygous for GRN mutations develop the lysosomal storage disorder neuronal ceroid lipofuscinosis (NCL11) characterized by neurodegeneration and blindness (Rohrer J D et al., (2015b) *Lancet Neurol.* 14:253-262). Adults heterozygous for LoF mutations develop adult-onset FTD with lysosomal storage lesions and TDP-43 inclusions in cortical neurons in the frontal and temporal lobes. MRI scans of pre-symptomatic GRN mutation carriers show structural differences in the temporal and parietal lobes ~15 years before expected clinical onset (Rohrer et al supra).

There is no effective treatment that significantly alters disease progression for any form of FTD, amyotrophic lateral sclerosis (ALS) or any form of neurodegenerative disease at present. The only medication prescribed for FTD is designed to mitigate the impact of depression (anti-depressants) or problematic behaviours (major tranquilisers) and these often have significant harmful short and long-term side effects.

Progranulin (PGRN) is a secreted glycoprotein that has important trophic effects on neurons, inhibits inflammation and plays a key role in autophagy (Chitramuthu B P et al., (2017) *Brain.* 140(12):3081-3104). Progranulin is produced by microglia and neurons but is taken up by all cell types. Once it binds to its receptor sortilin on the cell membrane, it is imported by endosomes and delivered to lysosomes where it is degraded into multiple granulins (Holler C J et al., (2017) *eNeuro.* 18:4). One of these granulins acts as a chaperone for the protease cathepsin D to promote lysosomal acidification and effective proteolysis. Lysosomal defects inhibit autophagy and TDP-43 accumulates in nuclear and cytoplasmic inclusions.

GRN-\- mice show a subtle behavioural phenotype (reduced social dominance) and, despite developing lipofuscinosis, reactive gliosis and abnormal lysosomes, they do not develop TDP-43 proteinopathy or neuronal loss (Arrant A W et al., (2018) *J. Neurosci.* 38(9):2341-2358). Selective knockout of GRN from neurons (Petkau T L et al., (2017) *Neurobiol Dis.* 106:14-22) or partial knockout from microglia (Petkau T L et al., (2017) *J. Neuroinflammation.* 14(1): 225) in mice reduced PGRN levels by ~50% but does not result in a phenotype or detectable pathology. This indicates that both cell types can secrete sufficient progranulin to deliver tissue-wide cross-correction.

Despite the absence of a good animal model, previous studies using viral vectors to deliver PGRN have shown promise. The intraparenchymal infusion of the mouse GRN gene delivered by the Adeno-Associated Virus 1 (AAV1) to 12 month old GRN-\- mice reduced lipofuscinosis and inflammation, suggesting that progranulin supplementation could reverse aspects of pathology (Arrant A E et al., (2017) *Brain.* 140(5):1447-1465; Arrant A E et al., (2018) supra). However, another study using human GRN at ~33 fold higher doses delivered by AAV9 and AAV4 reported marked hippocampal degeneration with T Cell infiltrates in GRN$^{-/-}$ mice and non-transgenic mice after 3 months (Amado D A et al., doi: https://doi.org/10.1101/308692).

The remarkable success of a recent trial of AAV9-SMN in type 1 Spinal Muscular Atrophy (SMA) has spurred the search for gene therapies for neurological disorders. SMA is caused by homozygous deletions of the survival motor neuron gene (SMN). These children are born floppy and become progressively weaker such that they never sit, crawl, stand or speak as 95% are ventilated before the age of two. Of the 15 patients given a single injection of AAV9-SMN between 1 and 7 months of age, none required ventilation and 14/15 had a remarkable increase in muscle strength such that they could stand and walk unaided and all could speak (Mendell J R, et al., (2017) *N. Engl. J. Med.* 377(18):1713-1722).

However, high dose intravenous AAV9-SMN in non-human primates and mini-pigs has been reported to be toxic (Hinderer C et al., (2018) *Hum. Gene Ther.* 29:285-298) so careful consideration should be given to minimise vector dose in any clinical trial. In addition, AAV vector production is an extremely expensive process with current estimates being up to ~$1 m per patient.

Because GRN overexpression can double the survival of transgenic mice expressing a mutant form of TDP-43 that models amyotrophic lateral sclerosis (ALS) and FTD (Beel S et al., (2018) *Mol. Neurodegener.* 13(1):55), AAV-GRN therapy may be a successful therapy for ALS and for FTD due to TDP-43 accumulation that is not associated with GRN mutations. Clearance of amyloid β deposition in the brain has also been enhanced by the administration of lenti-virus delivering GRN to transgenic mouse models of Alzheimer's (Minami S S et al., (2014) *Nat. Med.* 20(10): 1157-64), and progranulin gene delivery has been shown to be neuroprotective in the MTPT toxin model of Parkinson's (Van Kampen J M et al., (2014) *PLoS One.* 9(5): e97032). Because GRN is able to enhance autophagy and reduce inflammation, AAV-GRN may also provide therapeutic benefit for many other neurodegenerative disorders in which misfolded proteins accumulate.

A number of research groups are already investigating a variety of approaches to find suitable treatments for FTD-GRN patients, including delivery of progranulin using AAV vectors. For example, Passage Bio has received significant funding to develop AAV-delivered therapeutics to treat rare monogenic CNS diseases, including FTD (https://www.passagebio.com/investors-and-media/news-and-events/press-releases/press-release-details/2019/Passage-Bio-Launches-with-1155-Million-Series-A-to-Develop-AAV-Delivered-Therapeutics-to-Treat-Rare-Monogenic-CNS-Diseases/default.aspx). WO 2017/151884 also describes the use of a vector comprising a nucleic acid encoding progranulin in which the vector transduces cells that contact the cerebrospinal fluid (CSF) to express the progranulin. In particular, the vector includes the AAV capsid protein and the progranulin nucleic acid is inserted between a pair of AAV inverted terminal repeats.

However, in view of the known toxicity of high doses of AAV vectors, there is a real need to optimise expression of the progranulin protein carried in such a vector so that administration of such a vector results in the return of brain progranulin levels close to physiological levels in subjects who carry loss of function (LoF) mutations in the GRN gene, as well as subjects who have decreased, suppressed or low levels of progranulin. Indeed, optimisation of therapeutic protein expression may be applied and extended to a number of diseases for which the cause is a genetic defect or failure of a physiological system to produce a protein below physiologically normal levels.

Accordingly, there is a need for improved AAV vectors showing increased expression of heterologous genes such as progranulin in the brain.

SUMMARY OF THE INVENTION

In one aspect, the present invention provides an adeno-associated virus (AAV) vector comprising a nucleic acid comprising a human growth hormone intron 3 (hGHi3) sequence operably coupled to a polynucleotide sequence encoding a polypeptide of interest.

In a further aspect, the present invention provides an adeno-associated virus (AAV) vector comprising a synapsin promoter sequence operably coupled to a polynucleotide sequence encoding a polypeptide of interest. Preferably the polypeptide of interest is progranulin.

In a further aspect, the present invention provides an adeno-associated virus (AAV) vector comprising a progranulin 3' untranslated region (UTR) sequence operably coupled to a polynucleotide sequence encoding a polypeptide of interest. Preferably the polypeptide of interest is progranulin.

In a further aspect, the present invention provides an adeno-associated virus (AAV) vector comprising a polynucleotide sequence encoding progranulin, wherein the polynucleotide sequence has at least 95% sequence identity to SEQ ID NO:4.

In one example, the hGHi3 sequence may comprise the sequence of SEQ ID NO:7 or a variant, fragment or homolog thereof. For instance, suitable variants may comprise a sequence having at least 85%, 90%, 95% or 99% sequence identity to SEQ ID NO:7, e.g. over at least 30, 50, 70, 80, 90 residues of, or over the full length of SEQ ID NO:7.

Preferably the polynucleotide sequence encodes a heterologous polypeptide or transgenic protein, e.g. a non-AAV protein. In some embodiments, the polynucleotide sequence may encode a mammalian polypeptide, e.g. a human polypeptide or protein. In one embodiment, the polynucleotide sequence may comprise the complete coding sequence for the polypeptide of interest or part of the coding sequence therefor. As an example, the coding sequence may be derived from GRN and code for progranulin (PGRN), e.g. human progranulin. It is preferred if the polynucleotide sequence comprises the complete coding sequence for PGRN.

Thus, the polynucleotide sequence preferably encodes an amino acid sequence as defined in SEQ ID NO:16, or a fragment, homolog or variant thereof. In a preferred embodiment, the encoded amino acid sequence may have at least 85%, 90%, 95% or 99% sequence identity to SEQ ID NO:16, e.g. over at least 50, 100, 200, 300, 500 residues of, or over the full length of SEQ ID NO:16.

In one embodiment, the polynucleotide sequence may comprise the wild-type coding sequence for human progranulin (SEQ ID NO:1), or a variant, fragment or homolog thereof.

In a preferred embodiment, the polynucleotide sequence may be codon-optimised, for example, optimised for expression in humans. In one preferred embodiment, the codon-optimised sequence has a codon adaptation index (CAI) for humans of at least 0.8, more preferably at least 0.9. Most preferably the codon-optimised sequence has a CAI for both humans and mouse of at least 0.9. Preferably the codon-optimised sequence has a GC content of 30 to 70%, most preferably 60 to 65%. In one embodiment, the codon-optimised sequence has at least 50%, 60%, 70%, 75%, or most preferably at least 80% sequence similarity or sequence identity to the wild-type progranulin sequence.

Codon-optimisation may introduce new or different regulatory elements that enhance protein production. Such regulatory elements may additionally restrict expression to particular tissues and/or organs, such as the brain. In one example, the codon-optimised sequence may comprise the sequence of SEQ ID NO:2, SEQ ID NO:3 or SEQ ID NO:4, or a variant, fragment or homolog thereof. In a particularly preferred embodiment, the codon-optimised sequence may comprise the sequence of SEQ ID NO:4, or a variant, fragment or homolog thereof, i.e. based on candidate III (PGRN-GS) described in the examples herein.

Suitable variants may comprise a sequence having at least 85%, 90%, 95% or 99% sequence identity to SEQ ID NO:1, SEQ ID NO:2, SEQ ID NO:3 or SEQ ID NO:4, e.g. over at least 100, 200, 300, 500, 1000 or 1500 residues of, or over the full length of SEQ ID NO:1, SEQ ID NO:2, SEQ ID NO:3 or SEQ ID NO:4. In a particularly preferred embodiment, polynucleotide sequence may comprise a sequence having at least 85%, 90%, 95% or 99% sequence identity to SEQ ID NO:4, e.g. over at least 100, 200, 300, 500, 1000 or 1500 residues of, or over the full length of SEQ ID NO:4.

In general, suitable fragments may comprise at least 20, 30, 50, 100, 200, 300, 500, 1000 or 1500 residues of any one of the polynucleotide or amino acid sequences described herein, e.g. at least 20, 30, 50, 100, 200, 300, 500, 1000 or 1500 residues of SEQ ID NO:1, SEQ ID NO:2, SEQ ID NO:3 SEQ ID NO:4, SEQ ID NO:7, SEQ ID NO:14, SEQ ID NO:15, SEQ ID NO:16 or SEQ ID NO:17.

In another embodiment, the AAV vector may further comprise an exonic splicing element (ESE). The ESE may be upstream of the polynucleotide coding sequence, for example, in a 5' flanking sequence. It will be appreciated that the ESE may be part of or inserted into a flanking sequence. Such a 5' flanking sequence may be a guide sequence, such as a 5' flanking sequence derived from a wild-type polynucleotide sequence. For example, the 5'flanking sequence may be a 5' guide sequence derived from the wild-type GRN gene. In such an example, the wild type GRN 5' guide sequence comprises about 300 to 500 base pairs, e.g. 350 to 450 or about 392 base pairs.

In a preferred embodiment, the AAV vector may further comprise a 3' untranslated region (UTR) from progranulin. The 3' UTR of PGRN may function as an exonic enhancing element to enhance and potentially regulate PGRN expression. The 3' UTR of PGRN may, for example, be located in the cassette or vector downstream of the polynucleotide coding sequence, i.e. in the 3' region. Preferably the cassette or vector comprises the 3' UTR of human PGRN, or a variant, fragment or homolog thereof. For instance the cassette or vector may comprise the sequence of SEQ ID NO:14, or a sequence having at least 85%, 90%, 95% or 99% sequence identity to SEQ ID NO:14, e.g. over at least 100, 200, 250 residues of, or over the full length of SEQ ID NO:14.

In a further embodiment, the polynucleotide sequence may include a signalling sequence (i.e. a sequence encoding a signalling peptide) derived from human growth hormone (hGH). The hGH signalling sequence may comprise the sequence of SEQ ID NO:9 or a variant or homolog thereof. In some embodiments, the signalling sequence may replace a signalling sequence present in the sequence encoding the polypeptide of interest. In a particular example, the hGH signalling sequence replaces residues 1 to 51 of GRN.

In a yet further embodiment, the AAV vector may further comprise a sequence that imparts tissue or cell-type specificity to the protein expression. For example, a neuron-specific promoter, such as a promoter derived from synapsin, may be included in the expression cassette. The promoter may, for example, comprise the sequence of SEQ ID NO:15, or a variant, fragment or homolog thereof. For instance the cassette or vector may comprise the sequence of SEQ ID NO:15, or a sequence having at least 85%, 90%, 95% or 99% sequence identity to SEQ ID NO:15, e.g. over at least 50, 100, 200, 300 or 400 residues of, or over the full length of SEQ ID NO:15.

In another embodiment, the present invention provides an AAV vector comprising a human synapsin promoter, hGHi3 and a progranulin 3' UTR operably coupled to a polynucleotide sequence encoding a polypeptide of interest. Preferably, the polynucleotide sequence may be codon-optimised, for example, optimised for expression in humans. Even more preferably the polypeptide of interest is progranulin. The AAV vector may, for example, comprise the sequence of SEQ ID NO:17, or a variant, fragment or homolog thereof. For instance, the AAV vector may comprise the sequence of SEQ ID NO:17, or a sequence having at least 85%, 90%, 95%, or 99% sequence identity to SEQ ID NO:17, e.g. over at least 100, 200, 300, 500, 1000, 1500, 2000, 2500, or 3000 residues of, or over the full length of SEQ ID NO:17.

In another example, the sequence may additionally or alternatively limit expression of the polypeptide of interest to either dividing or non-dividing cells, such as non-dividing neurons. In this way, any carcinogenic risk may be reduced.

Thus, in a specific example, the present invention provides an AAV vector cassette to deliver the GRN gene for the efficient expression and secretion of progranulin to supplement PGRN levels in the brains of subjects with ALS, FTD and NCL11 and related neurodegenerative disorders. Such subjects may have levels of progranulin below a normal physiological level, have GRN mutations or are either partially or wholly deficient in this protein.

While it will be appreciated that the present invention encompasses the use of any suitable serotype of AAV, serotype AAV9 is a preferred example.

In a second aspect, the present invention resides in i) a pharmaceutical composition or medicament comprising an AAV vector as described herein and ii) one or more pharmaceutically or physiologically acceptable carriers, excipients and/or diluents.

In one embodiment, the pharmaceutical composition or medicament may be formulated for administration or delivery directly or indirectly to the brain or a specific area of the brain, such as the frontal, temporal and/or parietal lobes.

In a third aspect, the pharmaceutical composition or medicament as described herein may be for use in the treatment of disease, preferably a neurological disease or disorder. Typically, the disease to be treated is a neurodegenerative disease. In particular embodiments, the neurological disorder comprises frontotemporal dementia (FTD), neuronal ceroid lipofuscinosis (CLN11), amyotrophic lateral sclerosis (ALS), Huntington's disease, Parkinson's disease or Alzheimer's disease.

The pharmaceutical composition or medicament may be used to treat any patient suffering from the disease, or a sub-group of patients thereof. In some embodiments, the pharmaceutical composition or medicament as described herein is used to treat (i) subjects who are heterozygous, homozygous or compound heterozygous for GRN mutations, (ii) subjects suffering from sporadic neurological disease and/or (iii) subjects having PGRN levels below a physiologically normal level. By "sporadic disease" it is typically meant subjects who are not known to have another family member affected or do not have a loss of function GRN mutation linked to the disease.

Expressed in another way, use of the pharmaceutical composition or medicament as described herein may be for the manufacture of a medicament for the treatment of a neurological disorder, e.g. for treating frontotemporal dementia (FTD-GRN) patients who are heterozygous for a GRN mutation or for treating neuronal ceroid lipofuscinosis (NCL11) patients who are homozygous or compound heterozygous for GRN mutations. The medicament may also be used for other neurological disorders in people who do not have PGRN levels below a physiologically normal level e.g. frontotemporal dementia (FTD) patients who do not have GRN mutation, amyotrophic lateral sclerosis (ALS), Huntington's disease, Parkinson's disease or Alzheimer's disease, and subjects suffering from other sporadic neurological diseases.

The pharmaceutical composition or medicament of the present invention may also be used in a method of treatment in which a therapeutically effective amount of a pharmaceutically or physiologically acceptable composition comprising an AAV vector as described herein may be administered to a subject in need thereof for the treatment of a neurological disorder, e.g. frontotemporal dementia (FTD), neuronal ceroid lipofuscinosis (NCL11), amyotrophic lateral sclerosis (ALS), Huntington's disease, Parkinson's disease or Alzheimer's disease, for example in subjects suffering from sporadic neurological disease and/or subjects having PGRN levels below a physiologically normal level. For example, the pharmaceutical composition or medicament of the invention may be administered as a gene therapy to FTD and ALS patients who have recently become symptomatic, thereby arresting the degenerative process. Such treatment may even rescue neurons that are dysfunctional but still alive. Even a modest improvement in dementia symptoms and prevention of progression would dramatically reduce the care burden on their family and the community.

It will be appreciated that the composition or medicament may be administered prophylactically to prevent or limit the onset of disease, particularly to subjects at greatest risk.

In a further aspect, the present invention provides a nucleic acid as described above, e.g. a nucleic acid (e.g. polynucleotide) comprising (i) a human growth hormone intron 3 (hGHi3) sequence (ii) a synapsin promoter sequence and/or (iii) a progranulin 3' untranslated region (UTR) sequence, operably coupled to a heterologous polynucleotide sequence encoding a polypeptide of interest (e.g. polypeptide other than human growth hormone). Preferably the polypeptide of interest comprises progranulin. The coding sequence for the polypeptide may be codon-optimized, e.g. as described herein.

In a further aspect, the present invention provides a nucleic acid sequence comprising a sequence having at least 85%, 90%, 95% or 99% sequence identity to SEQ ID NO:4, e.g. over at least 100, 200, 300, 500, 1000 or 1500 residues of, or over the full length of SEQ ID NO:4.

The nucleic acid sequence may further comprise one or more regulatory elements (such as promoter) or other elements as described above with reference to the AAV vector comprising such a nucleic acid. Thus in one embodiment the nucleic acid comprises a neuron-specific promoter (e.g. a synapsin promoter). The nucleic acid may e.g. comprise an expression cassette suitable for use in an AAV vector, and thus may e.g. comprise one or more AAV inverted terminal repeats.

BRIEF DESCRIPTION OF THE DRAWINGS

FIG. 1a: Twelve codon-optimised PGRN sequences were synthesized under the CMV promoter. HEK-293 cells were used for transfection (250 ng/2E+10 cells). 48 hours later the medium was collected and western blot analysis performed. FIG. 1b: The intensity of the PGRN expression was measured by ImageJ for each candidate. FIG. 1c: CAI score before and after the double codon optimisation (human and other species).

FIG. 2. Cloning strategy of hPGRN-fusion. FIG. 2a: Schematic diagram of candidates I, II, III of the codon optimised hPGRN by different algorithms. FIG. 2b: BamH1 and BstB1 were used to cut the 5' sequence of Wild-type human PGRN. The digested DNA fragments were replaced with codon optimised PGRN candidates to generate a fusion plasmid.

FIG. 3. Quantitation of secreted PGRN from codon optimised constructs in cell culture medium. FIG. 3a: PGRN codon optimised and fusion constructs were transfected into HEK-293 cells. After 48 hours the cell culture medium was sampled and levels of PGRN were assayed by western blot. FIG. 3b: Levels of secreted PGRN were measured by ImageJ for each candidate and the value was normalised initially to the number of cells (protein GAPDH) and subsequently to cassette copy number (qPCR of CMV/GAPDH). The results of three biological replicates and four independent experiments were plotted in the scatterplot and subjected to one-way ANOVA statistical analysis ($*<0.05$).

FIG. 4. Quantitation of expressed PGRN from codon optimised constructs in cell culture lysates. FIG. 4a: PGRN codon optimised and fusion constructs were transfected into HEK-293 cells. After 48 hours the cell cultures were lysed and levels of PGRN were assayed by western blot. FIG. 4b: Levels of expressed PGRN were measured by ImageJ for each candidate and the value was normalised initially to the number of cells (protein GAPDH) and subsequently to cassette copy number (qPCR of CMV/GAPDH). The results of three biological replicates and four independent experiments were plotted in the scatterplot and subjected to one-way ANOVA statistical analysis ($*<0.05$).

FIG. 5. Testing intron-mediated enhancement of human growth hormone on PGRN protein expression. FIG. 5a: Schematic diagram of the human growth hormone intronic sequence located in the genomic sequence. FIG. 5b: The hGH introns 1, 2 or 3 were cloned into the 5' UTR of human PGRN-wt. FIG. 5c: The human PGRN signalling sequence (18 amino acid peptide) was replaced with human growth hormone signalling sequence to test whether it could enhance the secretion of PGRN.

FIG. 6. Secretion of PGRN was enhanced by hGH intron 3 and signalling sequence of hGH. FIG. 6a: PGRN intronic and signalling peptide sequences were transfected into HEK-293 cells. After 48 hours the cell culture medium was sampled and levels of PGRN were assayed by western blot. FIG. 6b: Levels of secreted PGRN were measured by ImageJ for each candidate and the value was normalised initially to the number of cells (protein GAPDH) and subsequently to cassette copy number (qPCR of CMV/GAPDH). The results of three biological replicates and four independent experiments were plotted in the scatterplot and subjected to one-way ANOVA statistical analysis ($*<0.05$, $***<0.0005$).

FIG. 7. PGRN expression was enhanced by hGH intron3 but not by hGH signalling in cell lysates. FIG. 7a: PGRN intronic and signalling peptide sequences were transfected into HEK-293 cells. After 48 hours the cell cultures were lysed and levels of PGRN were assayed by western blot. FIG. 7b: Levels of expressed PGRN were measured by ImageJ for each candidate and the value was normalised initially to the number of cells (protein GAPDH) and subsequently to cassette copy number (qPCR of CMV/GAPDH). The results of three biological replicates and four independent experiments were plotted in the scatterplot and subjected to one-way ANOVA statistical analysis ($***<0.0001$).

FIG. 8a: The hGH intron 3 inserted PGRN-GS was transfected to HEK-293 cells. 48 hours later the medium was collected and used for western blot for GRN expression. FIG. 8b: The expression levels were quantified using image-J and image studio and the values were normalized initially to the number of cells (protein GAPDH) and subsequently to cassette copy number (qPCR of CMV/GAPDH). FIG. 8c: ESE element of PGRN wild type sequences and codon optimised PGRN-GW were analysed by ESE finder 2.0. SR protein binding score was plotted as a bar graph. Each colour represents different type of SR splicing proteins.

FIG. 9a: Schematic diagram of hGHi3 cloning for hGHi3-PGRN-Fusion constructs. FIG. 9b: AAV harbouring hGHi3-PGRN-GA were produced and transduced to 7 days old rat primary cortical neurons. After five days of incubation, medium was collected for western blot analysis of PGRN expression levels. FIG. 9c: Levels of expressed PGRN were measured by ImageJ for each candidate and the value was normalised initially to the number of cells (protein GAPDH) and subsequently to cassette copy number (qPCR of CMV/GAPDH). The results of three biological replicates and four independent experiments were plotted in the scatterplot and subjected to one-way ANOVA statistical analysis.

FIG. 10. Synapsin promoter increased PGRN secretion by rat cortical neurons. FIG. 10a: Wild type PGRN was cloned under CMV and synapsin promoters in an AAV shuttle vector. The plasmids were transfected to rat cortical neuron at day 7 for five days then the medium was sampled and processed for western blot analysis. FIG. 10b: The intensity of the PGRN expression was measured by imageJ.

FIG. 11a: Virus particles were produced using a neuron specific AAV9 capsid. Then AAV particles were transduced to rat primary cortical neuron at day 7 with 1E+6 virus particles for 5 days. The medium was used for western blot. FIG. 11b: PGRN protein levels were measured by ELISA assay (0.001).

FIG. 12a: AAV9-CMV-PGRN-WT and AAV9-Syn-PGRN-WT were administered by bilateral ICV injection (1E+12 GC/Kg). FIG. 12b: qPCR for human PGRN was performed on genomic DNA to determine tissue biodistribution.

FIG. 13a: A commercial ELISA kit (Adipogen) was used for the quantitative analysis of PGRN expression levels in the serum, CSF and cortex. FIG. 13b: Serum was diluted 1:300 and used for the ELISA (n=3). FIG. 13c: CSF was diluted 1:200 dilution and used for the ELISA (N=1). FIG. 13d: RIPA lysate of cortex was diluted 1:300 and then used for ELISA (N=3).

FIG. 14. Example of a PGRN vector suitable for use in gene therapy. FIG. 14a: Schematic diagram of a CMV promoter driven PGRN codon optimised construct composed of hGH3 intron 3 in the 5'UTR. FIG. 14b: Schematic diagram of a Synapsin promoter driven PGRN codon optimised construct composed of hGH3 intron 3 in the 5'UTR.

FIG. 18. AAV9 carrying Syn-PGRN-GS, Syn-hGHi3-PGRN-GS and Syn-hGHi3-PGRN-GS-UTR enhanced the PGRN expression in mouse cortex. AAV9 vectors carrying Syn-PGRN-GS, Syn-hGHi3-PGRN-GS and Syn-hGHi3-PGRN-GS-UTR were delivered by bilateral IT injection. The cell lysate of cortex tissues was subjected to PGRN ESLISA assay and western blot. a) Commercial ELISA kit (Adipogen) was use for the quantitative analysis of PGRN expression levels in the cortex. b) RIPA lysate of cortex was diluted 1:300 and then used for ELISA (N=3). c) RIPA lysate of cortex from low (6.2E+10) Middle (1.2E+11) and High (2.5E+11) were used for ELISA (N=3).

LIST OF SEQUENCES

Figure 1:
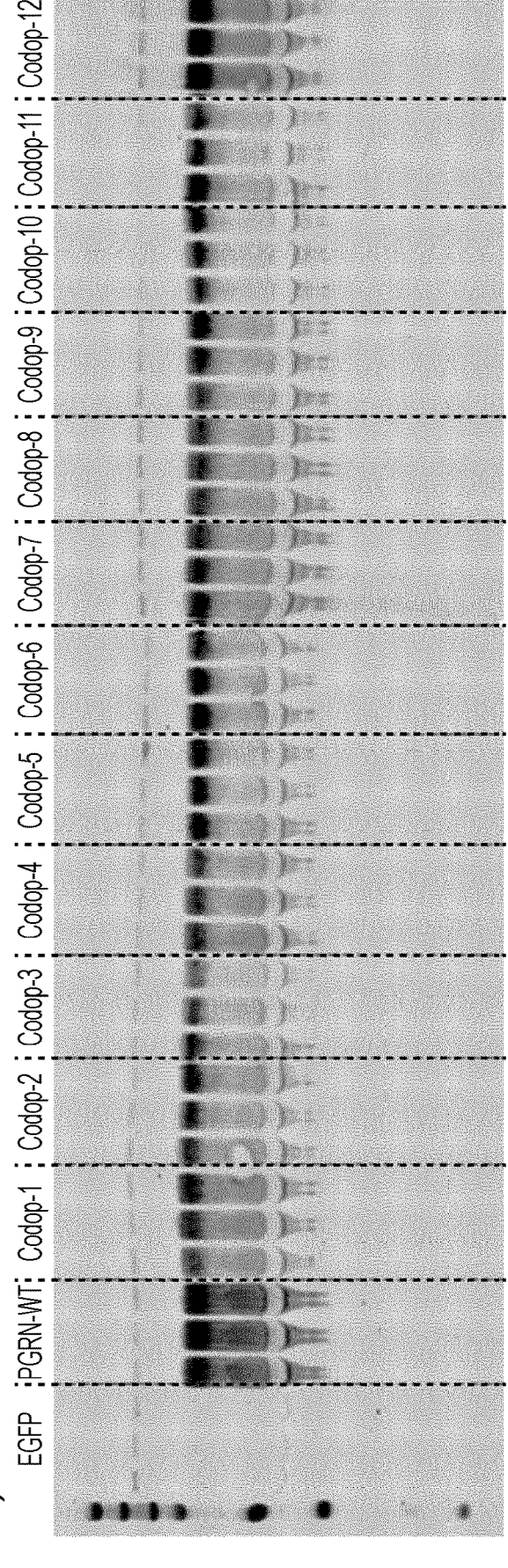
FIG. 1. Screening of secreted PGRN expression for codon-optimised candidates.
Figure 1:
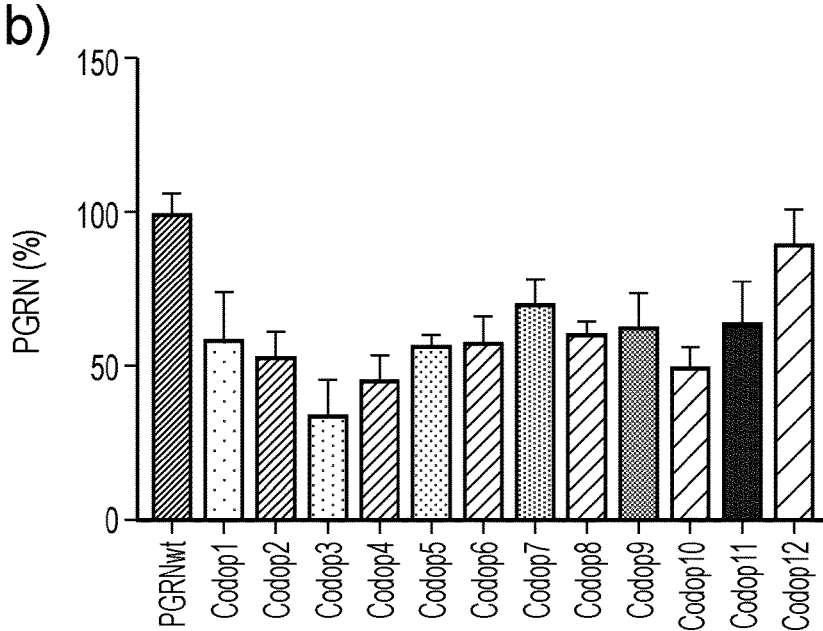

SEQ ID NO: 1—Human PGRN wild-type (PGRN-WT) DNA coding sequence;

SEQ ID NO:2—Candidate I (PGRN-IDT) artificial codon-optimised PGRN DNA coding sequence;

SEQ ID NO:3—Candidate II (PGRN-GA) artificial codon-optimised PGRN DNA coding sequence;

SEQ ID NO:4—Candidate III (PGRN-GS) artificial codon-optimised PGRN DNA coding sequence;

SEQ ID NO:5—human growth hormone intron 1 sequence;

SEQ ID NO:6—human growth hormone intron 2 sequence;

SEQ ID NO:7—human growth hormone intron 3 sequence;

SEQ ID NO:8—human growth hormone intron 4 sequence;

SEQ ID NO:9—generic DNA signalling sequence of human growth hormone;

SEQ ID NO:10—translated amino acid sequence for the generic signalling sequence of human growth hormone;

SEQ ID NO:11—5'ESE Flanking sequence RPL41;

SEQ ID NO:12—5'ESE Flanking sequence UCHL1;

SEQ ID NO:13—5'ESE Flanking sequence RPL38.

SEQ ID NO:14—Human PGRN 3' UTR sequence

SEQ ID NO:15—Synapsin promoter sequence

SEQ ID NO:16—Human PGRN amino acid sequence

SEQ ID NO: 17—Syn-hGHi3-PGRN-GS-UTR DNA cassette sequence (from ITR to ITR)

SEQ ID NO:18—bovine growth hormone (bGH) poly(A) signal

SEQ ID NO:19—5' AAV2 UTR sequence

SEQ ID NO:20—3' AAV2 UTR sequence

DETAILED DESCRIPTION OF THE INVENTION

In one embodiment, the present invention relates to an adeno-associated virus (AAV) vector comprising (i) a human growth hormone intron 3 (hGHi3) sequence (ii) a synapsin promoter sequence and/or (iii) a progranulin 3' untranslated region (UTR) sequence, operably coupled to a polynucleotide sequence encoding a polypeptide of interest.

The invention encompasses a specific embodiment in which the AAV vector cassette contains a codon-optimised PGRN gene that significantly increases the production and secretion of the progranulin protein. PGRN secretion may be further increased by placing the sequence under the 5' regulatory control of hGH intron 3. Use of the neuronal specific promoter, synapsin, restricts progranulin expression to neurons in vitro and in vivo, thereby reducing the risk of peripheral organ toxicity and carcinogenesis. The 3' UTR from PGRN may also be included in the cassette in order to further enhance and regulate PGRN expression.

It has been known since the late 1970s that intron-containing and intronless versions of otherwise identical genes can exhibit dramatically different expression profiles. hGHi3 is an intronic splicing element (ISE). However the specific effect of hGHi3 in increasing transgene expression/secretion in AAV vectors was not previously known. Moreover the inventors have found hGH introns 2 and 4 to have the opposite effect. Accordingly the increase in expression/secretion of transgenes from AAV vectors comprising a hGHi3 sequence is a surprising and advantageous result.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The term also encompasses "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of said members, or to any two or more of said members, such as, e.g., any ≥3, ≥4, ≥5, ≥6, or ≥7 etc. of said members, and up to all said members.

The term "nucleic acid" or "polynucleotide" refers to a (e.g. polymeric) form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

The terms "polypeptide," "peptide," and "protein" are used interchangeably herein to refer to polymers of amino acids of any length. The terms also encompass an amino acid polymer that has been modified; for example, disulphide bond formation, glycosylation, lipidation, phosphorylation, or conjugation with a labelling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wisc., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970)

Of interest is the BestFit program using the local homology algorithm of Smith and Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wisc., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

Mismatch Penalty: 1.00;
Gap Penalty: 1.00;
Gap Size Penalty: 0.33; and
Joining Penalty: 30.0.

The present disclosure provides a (recombinant) adeno-associated virus (AAV) vector. "AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes, for example, AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), AAV type 10 (AAV-10, including AAVrh10), AAV type 12 (AAV-12), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, and so on.

The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC-002077 (AAV-1), AF063497 (AAV-1), NC-001401 (AAV-2), AF043303 (AAV-2), NC-001729 (AAV-3), NC-001829 (AAV-4), U89790 (AAV-4), NC-006152 (AAV-5), AF513851 (AAV-7), AF513852 (AAV-8), and NC-006261 (AAV-8); the disclosures of which are incorporated by reference herein. See also, e.g., Srivistava et al. (1983) J. Virology 45:555; Chiorini et al. (1998) J. Virology 71:6823; Chiorini et al. (1999) J. Virology 73:1309; Bantel-Schaal et al. (1999) J. Virology 73:939; Xiao et al. (1999) J. Virology 73:3994; Muramatsu et al. (1996) Virology 221:208; Shade et al., (1986) J. Virol. 58:921; Gao et al. (2002) Proc. Nat. Acad. Sci. USA 99: 11854; Moris et al. (2004) Virology 33:375-383; international patent publications WO 00/28061, WO 99/61601, WO 98/11244; and U.S. Pat. No. 6,156,303.

The AAV vectors described herein are typically recombinant AAV vectors (rAAV). An "rAAV vector" as used herein refers to an AAV vector comprising a polynucleotide sequence not of AAV origin (i.e., a polynucleotide heterologous to AAV), typically a sequence of interest for the genetic transformation of a cell. In some embodiments, the heterologous polynucleotide may be flanked by at least one, and sometimes by two, AAV inverted terminal repeat sequences (ITRs). Preferably the ITRs are derived from AAV serotype 2, i.e. the rAAV vector comprises AAV2 ITRs. In some embodiments, the vector comprises one or both of the following AAV2 ITR sequences, or homologs or variants thereof:

SEQ ID NO: 19:
CCTGCAGGCAGCTGCGCGCTCGCTCGCTCACTGAGGCCGCCCGGGCGTCG

GGCGACCTTTGGTCGCCCGGCCTCAGTGAGCGAGCGAGCGCGCAGAGAGG

GAGTGGCCAACTCCATCACTAGGGGTTCCT

SEQ ID NO: 20:
AGGAACCCCTAGTGATGGAGTTGGCCACTCCCTCTCTGCGCGCTCGCTCG

CTCACTGAGGCCGGGCGACCAAAGGTCGCCCGACGCCCGGGCTTTGCCCG

GGCGGCCTCAGTGAGCGAGCGAGCGCGCAGCTGCCTGCAGG

Further suitable AAV ITR sequences are discussed in e.g. Wilmott et al. (2019), Human Gene Therapy Methods Vol. 30, No. 6:206-213 and are available from publicly-accessible databases.

The term rAAV vector encompasses both rAAV vector particles and rAAV vector plasmids. An rAAV vector may either be single-stranded (ssAAV) or self-complementary (scAAV). A suitable cloning vector comprising further sequence elements that may used in the vectors of the present invention is disclosed is RS540-AAV-ErbB-RASER1C-OFPBidBH3, disclosed in GenBank accession no. MK801287.1.

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Recombinant," as used herein means that the vector, polynucleotide, polypeptide or cell is the product of various combinations of cloning, restriction or ligation steps (e.g. relating to a polynucleotide or polypeptide comprised therein), and/or other procedures that result in a construct that is distinct from a product found in nature. A recombinant virus or vector is a viral particle comprising a recombinant polynucleotide. The terms respectively include replicates of the original polynucleotide construct and progeny of the original virus construct.

In embodiments of the present invention, the AAV vector comprises a nucleic acid sequence encoding a gene product, e.g. a heterologous nucleotide sequence encoding a heterologous polypeptide. A "gene" refers to a polynucleotide containing at least one open reading frame that is capable of encoding a particular protein after being transcribed and translated. A "gene product" is a molecule resulting from expression of a particular gene. Gene products include, e.g., a polypeptide, an aptamer, an interfering RNA, an mRNA, and the like.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

In one embodiment, the gene product (polypeptide of interest) is a therapeutic protein. A "therapeutic" peptide or protein is a peptide or protein that may alleviate or reduce symptoms that result from an absence or defect in a protein in a cell or subject. Alternatively, a "therapeutic" peptide or protein is one that otherwise confers a benefit to a subject, e.g., anti-degenerative effects.

Where the gene product is a polypeptide, the polypeptide is generally a polypeptide that enhances function of a cell, for example a cell present in neuronal tissue, e.g., a neuron, a glial cell, or a photoreceptor cell. Exemplary polypeptides include neuroprotective polypeptides (e.g., GDNF, CNTF, NT4, NGF, and NTN); anti-angiogenic polypeptides (e.g., a soluble vascular endothelial growth factor (VEGF) receptor; a VEGF-binding antibody; a VEGF-binding antibody fragment (e.g., a single chain anti-VEGF antibody); endostatin;

tumstatin; angiostatin; a soluble Fit polypeptide (Lai et al. (2005) Mol. Ther. 12:659); an Fc fusion protein comprising a soluble Fit polypeptide (see, e.g., Pechan et al. (2009) Gene Ther. 16: 10); pigment epithelium-derived factor (PEDF); a soluble Tie-2 receptor; etc.); tissue inhibitor of metalloproteinases-3 (TIMP-3); a light-responsive opsin, e.g., a rhodopsin; anti-apoptotic polypeptides (e.g., Bcl-2, Bcl-Xl); and the like. Suitable polypeptides include, but are not limited to, glial derived neurotrophic factor (GDNF); fibroblast growth factor 2; neurturin (NTN); ciliary neuro- trophic factor (CNTF); nerve growth factor (NGF); neuro- trophin-4 (NT4); brain derived neurotrophic factor (BDNF); epidermal growth factor; rhodopsin; X-linked inhibitor of apoptosis; and Sonic hedgehog. Suitable polypeptides are disclosed, for example, in WO 2012/145601. However in a preferred embodiment, the encoded polypeptide comprises progranulin.

In embodiments of the present invention, the polynucle- otide sequence is operably coupled to (i) a human growth hormone intron 3 (hGHi3) sequence (ii) a synapsin promoter sequence and/or (iii) a progranulin 3' untranslated region (UTR) sequence. In some embodiments, the polynucleotide sequence encoding a polypeptide is operably linked to a promoter, e.g. a constitutive promoter or an inducible pro- moter. In some instances, the nucleotide sequence encoding the polypeptide of interest is operably linked to a tissue specific or cell type specific regulatory element.

For example, in some instances, a nucleotide sequence encoding a gene product of interest is operably linked to a neuron-specific regulatory element (e.g., a neuron-specific promoter), e.g., a regulatory element that confers selective expression of the operably linked gene in a neuron Suitable neuronal-specific promoters include neuron-specific enolase (NSE) promoter, Andersen et al. Cell. Mol. Neurobiol., 13:503-15 (1993; neurofilament light-chain gene promoter, Piccioli et al., Proc. Natl. Acad. Sci. USA, 88:561 1-5 (1991); and the neuron-specific vgf gene promoter, Piccioli et al., Neuron, 15:373-84 (1995)]; among others. However the neuron-specific promoter is preferably a synapsin pro- moter.

A "control element" or "control sequence" is a nucleotide sequence involved in an interaction of molecules that con- tributes to the functional regulation of a polynucleotide, including replication, duplication, transcription, splicing, translation, or degradation of the polynucleotide. The regu- lation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expres- sion of jellyfish GFP in vertebrates. In addition, one pro- moter element can increase an amount of recombinant products expressed for multiple DNA sequences attached in tandem. Hence, one promoter element can enhance the expression of one or more recombinant products. Multiple promoter elements are well-known to persons of ordinary skill in the art.

The term "enhancers" or "enhancer" as used herein can refer to a DNA sequence that is located adjacent to the DNA sequence that encodes a recombinant product. Enhancer elements are typically located upstream of a promoter ele- ment or can be located downstream of or within a coding DNA sequence (e.g., a DNA sequence transcribed or trans- lated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordi- nary skill in the art.

In some embodiments, the AAV vector may further com- prise a polyadenylation signal. For instance a poly(A) signal may be present typically at the 3' end of the cassette comprising the polynucleotide encoding a polypeptide of interest. In one embodiment, a poly(A) signal is present downstream of a progranulin 3' untranslated region, i.e. between the 3' UTR sequence and one of the ITRs flanking the cassette. In one embodiment, the poly(A) sequence comprises or consists of a bovine growth hormone (bGH) poly(A) signal. Suitable polyadenylation signal (including bGH poly(A)) are known and are described in e.g. Choi et al. Molecular Brain 2014, 7:17; Goodwin E C, J Biol Chem. 1992; 267:16330-16334 and U.S. Pat. No. 5,122,458. In one embodiment, the bGH poly(A) signal comprises the sequence of SEQ ID NO:18, or a homolog or variant thereof:

```
                                    SEQ ID NO: 18
GTCCTTTCCTAATAAAATGAGGAAATTGCATCGCATTGTCTGAGTAGGTG

TC
```

The present disclosure provides a pharmaceutical com- position or medicament comprising: a) an AAV vector, as described herein; and b) a pharmaceutically acceptable carrier, diluent, excipient, or buffer. In some embodiments, the pharmaceutically acceptable carrier, diluent, excipient, or buffer may be suitable for use in a human.

By "pharmaceutically acceptable" it is meant a material that is not biologically or otherwise undesirable, e.g., the material may be administered to a subject without causing any undesirable biological effects. Thus, such a pharmaceu- tical composition may be used, for example, in transfection of a cell ex vivo or in administering a viral particle or cell directly to a subject.

Such excipients, carriers, diluents, and buffers include any pharmaceutical agent that can be administered without undue toxicity. Pharmaceutically acceptable excipients include, but are not limited to, liquids such as water, saline, glycerol and ethanol.

The term "one or more physiologically or pharmaceutically acceptable carriers, excipients and/or diluents" as used herein is intended to include any and all solvents, dispersion media, coatings, antibacterial and antifungal agents, isotonic and absorption delaying agents, and the like, compatible with administration to humans or other vertebrate hosts. Typically, a pharmaceutically acceptable diluent, excipient, and/or carrier is a diluent, excipient, and/or carrier approved by a regulatory agency of a Federal, a state government, or other regulatory agency, or listed in the US and/or European Pharmacopeia or other generally recognised pharmacopeia for use in animals, including humans as well as non-human mammals. The term diluent, excipient, and/or "carrier" refers to a diluent, adjuvant, excipient, or vehicle with which the pharmaceutical composition is administered. Such pharmaceutical diluent, excipient, and/or carriers may be sterile liquids, such as water and oils, including those of petroleum, animal, vegetable or synthetic origin. Water, saline solutions and aqueous dextrose and glycerol solutions may be employed as liquid diluents, excipients, and/or carriers, particularly for injectable solutions. Suitable pharmaceutical diluents and/or excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, may also contain minor amounts of wetting, bulking, emulsifying agents, or pH buffering agents. These compositions may take the form of solutions, suspensions, emulsion, sustained release formulations and the like. Examples of suitable pharmaceutical diluent, excipient, and/or carriers are described in "Remington's Pharmaceutical Sciences" by E. W. Martin. The formulation should suit the mode of administration. The appropriate diluent, excipient, and/or carrier will be evident to those skilled in the art and will depend in large part upon the route of administration.

Pharmaceutically acceptable salts may be included therein, for example, mineral acid salts such as hydrochlorides, hydrobromides, phosphates, sulphates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7(th) ed., Lippincott, Williams, & Wilkins; and Handbook of Pharmaceutical Excipients (2000) A. H. Kibbe et al., eds., 3 rd ed. Amer. Pharmaceutical Assoc.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid are used in the preparation of injectables. The injectable formulations may be sterilised, for example, by filtration through a bacteria-retaining filter, or by incorporating sterilising agents in the form of sterile solid compositions which may be dissolved or dispersed in sterile water or other sterile injectable medium prior to use.

Solid dosage forms for oral administration include capsules, tablets, pills, powders, and granules. In such solid dosage forms, the encapsulated or unencapsulated composition is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulphate, and mixtures thereof. In the case of capsules, tablets, and pills, the dosage form may also comprise buffering agents.

Medicaments described herein may be provided as a kit which comprises at least one container and a package insert. The container contains at least one dose of a medicament comprising a composition as described herein. The package insert, or label, comprises instructions for treating a patient using the medicaments as described herein. The kit may further comprise other materials that may be useful in administering the medicaments, such as diluents, filters, IV bags and lines, needles and syringes.

The methods of the present invention provide a means for delivering nucleic acid sequences into a host tissue or cell. The vectors and other reagents, methods and pharmaceutical formulations of the present invention are additionally useful in a method of administering a protein or peptide to a subject in need thereof, as a method of treatment or otherwise. In this manner, the protein or peptide may thus be produced in vivo in the subject. The subject may be in need of the protein or peptide as a method of treatment or otherwise because the subject has a deficiency of the protein or peptide, as explained further below.

As used herein, the terms "treatment," "treating," and the like, refer to obtaining a desired pharmacologic and/or physiologic effect. The effect may be prophylactic in terms of completely or partially preventing or reversing a disease or symptom thereof and/or may be therapeutic in terms of a partial or complete cure for a disease and/or adverse effect attributable to the disease. "Treatment" as used herein covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

In general, the present invention may be employed to deliver any foreign nucleic acid with a biological effect to treat or ameliorate the symptoms associated with any disorder related to gene expression in any organ, tissue or cell, especially those associated with e.g. the brain.

Gene transfer has substantial potential use in understanding and providing therapy for disease states. There are a number of inherited diseases in which defective genes are known and have been cloned. In some cases, the function of these cloned genes is known. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus, the methods of the present invention permit the treatment of genetic diseases. As used herein, a disease state is treated by partially or wholly remedying the deficiency or imbalance that causes the disease or makes it more severe. The use of site-specific integration of nucleic sequences to cause mutations or to correct defects is also possible.

In one aspect the present invention provides a method of delivering a gene product to a tissue or cell (e.g. a neuronal tissue or cell) in a subject, the method comprising administering to the subject an AAV vector as described above. The gene product may be a polypeptide e.g. as described above. The cell may, for example, be a blood cell, stem cell, bone marrow (e.g. hematopoietic) cell, liver cell, cancer cell, vascular cell, pancreatic cell, neural cell, glial cell, epithelial or endothelial cell, dendritic cell, fibroblast, lung cell, muscle cell, cardiac cell, intestinal cell or renal cell. Similarly the tissue may, for example, be selected from blood, bone marrow, muscle tissue (e.g. skeletal muscle, cardiac muscle or smooth muscle including vascular smooth muscle), central or peripheral nervous system tissue (e.g. brain, neuronal tissue or retinal tissue), pancreatic tissue, liver tissue, kidney tissue, lung tissue, intestinal tissue or heart tissue.

Delivering a gene product to a neuronal tissue or cell may provide for treatment of a neurological disorder. The gene product may be delivered to various cell types present in neuronal tissue, e.g. neurons or glial cells (e.g. astrocytes, oligodendrocytes and so on).

The present disclosure provides a method of treating a disease (e.g. a neurological disease), the method comprising administering to an individual in need thereof an effective amount of an AAV vector as described above. A subject AAV vector may be administered via intracranial injection, intracerebral injection, intraocular injection, intravenous injection or by any other convenient mode or route of administration.

Further exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspensions in liquid prior to injection, or as emulsions. Alternatively, one may administer the virus in a local rather than systemic manner, for example in a depot or sustained-release formation.

Recombinant virus vectors are preferably administered to the subject in an amount that is sufficient to result in infection (or transduction) and expression of the heterologous nucleic acid sequence in cells (e.g. neuronal cells) of the subject. Preferably the target cells are neural cells (including cells of the central and peripheral nervous systems, in particular, brain cells).

Preferably the vector is administered in a therapeutically effective amount. A "therapeutically-effective" amount as used herein is an amount of that is sufficient to alleviate (e.g., mitigate, decrease, reduce) at least one of the symptoms or causes associated with a disease state. Alternatively stated, a "therapeutically-effective" amount is an amount that is sufficient to provide some improvement in the condition of the subject. A "therapeutically effective amount" will fall in a relatively broad range that may be determined through experimentation and/or clinical trials. For example, for in vivo injection, a therapeutically effective dose may be on the order of from about $10^6$ to about $10^{15}$ of AAV virions, e.g., from about $10^8$ to $10^{12}$ AAV virions. For in vitro transduction, an effective amount of AAV virions to be delivered to cells will be on the order of from about $10^8$ to about $10^{13}$ of the AAV virions. Other effective dosages may be readily established by one of ordinary skill in the art through routine trials establishing dose response curves. As will be appreciated by those of ordinary skill in this art, the effective amount of a composition or medicament comprising an AAV vector as described herein may vary depending on such factors as the desired biological endpoint, the drug to be delivered, the target tissue, the route of administration, etc. Additional factors which may be taken into account include disease severity; age, weight and gender of the patient being treated; diet, time and frequency of administration; drug combinations; reaction sensitivities; and tolerance/response to therapy.

In some embodiments, more than one administration (e.g., two, three, four or more administrations) may be employed to achieve the desired level of gene expression over a period of various intervals, e.g., daily, weekly, monthly, yearly, etc.

The present invention finds use in both veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are the most preferred. Human subjects include foetal, neonatal, infant, juvenile and adult subjects.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The following examples are provided to illustrate certain embodiments of the invention. It is not intended to limit the invention in any way.

EXAMPLES

Example 1. Increasing Efficiency of PGRN Translation by Codon Optimisation Algorithms The rate of protein translation from RNA transcripts may be improved by changing codons to use those that are optimal for a particular species and can increase gene expression in specific cell types. By optimising protein production from each transcript, the amount of viral vector used is less, reducing the risk of toxicity and cost. The optimisation of wild-type PGRN transcript was modelled using three open source programmes (IDT, Geneart and Genscript: see details in materials and methods). A rare-codon analysis tool was used to validate the codon adaptation index (CAI; https://www.genscript.com/tools/rare-codon-analysis). A CAI of 1.0 is considered ideal while a CAI of >0.8 is rated as good for expression in the desired expression organism. The lower the number, the higher the chance that the gene will be expressed poorly.

1.1 Codon Optimisation Design

The coding sequence of GRN (NM 002087.3) was redesigned using commercially available codon optimisation algorithms (TDT®, https://eu.idtdna.com/CodonOpt), (GeneArt®, https://www.thermofisher.com/order/geneartgenes/projectmgmt) and (GenScript®, https://www.genscript.com/tools/rare-codon-analysis)). The codon adaptation index (CAI, GeneScript) was utilised to rank the modified GRN sequences. A CAI of >0.8 is rated suitable for expression in the desired organism and the sequences and CAIS generated using the different algorithms are illustrated in FIGS. 1a and 1b. To develop the best codon optimised PGRN, algorithms for human and other species were applied (FIG. 1c). 14 novel constructs were designed and synthesised. The consensus Kozak sequence (GCCACC) was inserted before the ATG start codon and manufactured by IDT, GeneArt and GenScript respectively and named PGRN-IDT, PGRN-GA and PGRN-GS.

1.1.1 PGRN Codon Optimisation

To identify the optimal codon optimised PGRN sequence, dual codon optimisation was applied using a GenScript algorithm (https://www.genscript.com/codon optpr.html) service to ensure the codon optimised sequence was viable in animal models as well as in human cell lines and humans: the codon optimisation of PGRN for human might not be compatible for other species such as a mouse or large animal (sheep or monkey). Therefore, twelve dual-codon optimised human PGRN transgenes were designed which significantly improved CAI scores for both human and other species (see FIG. 1c). However, PGRN expression and secretion levels tested by western blot did not dramatically improve PGRN protein expression, except for one which was optimised for human and mouse (codop12, PGRN-GS; FIGS. 1a and 1b). Therefore, additional algorithms for human PGRN were applied to create PGRN-IDT and PGRN-GA. All three constructs (PGRN-GS, PGRN-GA and PGRN-IDT) were then tested for optimal expression levels.

1.1.2 Sequences of Codon-Optimised PGRN Designed using Three Different Algorithms a) Human PGRN wild-type (PGRN-WT) DNA coding sequence (coding sequence (CDS) length: 1782 bp) [SEQ ID NO:1]:

(SEQ ID NO: 1)
```
ATGTGGACCCTGGTGAGCTGGGTGGCCTTAACAGCAGGGCTGGTGGCTGG

AACGCGGTGCCCAGATGGTCAGTTCTGCCCTGTGGCCTGCTGCCTGGACC

CCGGAGGAGCCAGCTACAGCTGCTGCCGTCCCCTTCTGGACAAATGGCCC

ACAACACTGAGCAGGCATCTGGGTGGCCCCTGCCAGGTTGATGCCCACTG

CTCTGCCGGCCACTCCTGCATCTTTACCGTCTCAGGGACTTCCAGTTGCT

GCCCCTTCCCAGAGGCCGTGGCATGCGGGGATGGCCATCACTGCTGCCCA

CGGGGCTTCCACTGCAGTGCAGACGGGCGATCCTGCTTCCAAAGATCAGG

TAACAACTCCGTGGGTGCCATCCAGTGCCCTGATAGTCAGTTCGAATGCC

CGGACTTCTCCACGTGCTGTGTTATGGTCGATGGCTCCTGGGGGTGCTGC

CCCATGCCCCAGGCTTCCTGCTGTGAAGACAGGGTGCACTGCTGTCCGCA

CGGTGCCTTCTGCGACCTGGTTCACACCCGCTGCATCACACCCACGGGCA

CCCACCCCCTGGCAAAGAAGCTCCCTGCCCAGAGGACTAACAGGGCAGTG

GCCTTGTCCAGCTCGGTCATGTGTCCGGACGCACGGTCCCGGTGCCCTGA

TGGTTCTACCTGCTGTGAGCTGCCCAGTGGGAAGTATGGCTGCTGCCCAA

TGCCCAACGCCACCTGCTGCTCCGATCACCTGCACTGCTGCCCCCAAGAC

ACTGTGTGTGACCTGATCCAGAGTAAGTGCCTCTCCAAGGAGAACGCTAC

CACGGACCTCCTCACTAAGCTGCCTGCGCACACAGTGGGGGATGTGAAAT

GTGACATGGAGGTGAGCTGCCCAGATGGCTATACCTGCTGCCGTCTACAG

TCGGGGGCCTGGGGCTGCTGCCCTTTTACCCAGGCTGTGTGCTGTGAGGA

CCACATACACTGCTGTCCCGCGGGGTTTACGTGTGACACGCAGAAGGGTA

CCTGTGAACAGGGGCCCCACCAGGTGCCCTGGATGGAGAAGGCCCCAGCT

CACCTCAGCCTGCCAGACCCACAAGCCTTGAAGAGAGATGTCCCCTGTGA

TAATGTCAGCAGCTGTCCCTCCTCCGATACCTGCTGCCAACTCACGTCTG

GGGAGTGGGGCTGCTGTCCAATCCCAGAGGCTGTCTGCTGCTCGGACCAC

CAGCACTGCTGCCCCCAGGGCTACACGTGTGTAGCTGAGGGGCAGTGTCA

GCGAGGAAGCGAGATCGTGGCTGGACTGGAGAAGATGCCTGCCCGCCGGG

CTTCCTTATCCCACCCCAGAGACATCGGCTGTGACCAGCACACCAGCTGC

CCGGTGGGGCAGACCTGCTGCCCGAGCCTGGGTGGGAGCTGGGCCTGCTG

CCAGTTGCCCCATGCTGTGTGCTGCGAGGATCGCCAGCACTGCTGCCCGG

CTGGCTACACCTGCAACGTGAAGGCTCGATCCTGCGAGAAGGAAGTGGTC

TCTGCCCAGCCTGCCACCTTCCTGGCCCGTAGCCCTCACGTGGGTGTGAA

GGACGTGGAGTGTGGGGAAGGACACTTCTGCCATGATAACCAGACCTGCT

GCCGAGACAACCGACAGGGCTGGGCCTGCTGTCCCTACCGCCAGGGCGTC

TGTTGTGCTGATCGGCGCCACTGCTGTCCTGCTGGCTTCCGCTGCGCAGC

CAGGGGTACCAAGTGTTTGCGCAGGGAGGCCCCGCGCTGGGACGCCCCTT

TGAGGGACCCAGCCTTGAGACAGCTGCTGTGA
```

The Codon Adaptation Index (CAI) of wild-type human PGRN is 0.83 and GC content is 63.22%. The ideal percentage range of GC content is between 30% and 70%.

b) Candidate I (PGRN-IDT) artificial codon-optimised PGRN DNA coding sequence (CDS length: 1782 bp) [SEQ ID NO:2]:

ATGTGGACTCTCGTGAGTTGGGTCGCCCTTACTGCTGGACTTGTGGCTGG

CACAAGGTGCCCGGACGGGCAGTTCTGCCCTGTGGCATGTTGCCTTGATC

CCGGTGGCGCAAGCTACTCATGCTGTAGGCCACTGCTGGACAAATGGCCT

ACAACCCTCTCACGACACCTCGGCGGCCCATGTCAAGTAGATGCACATTG

TTCCGCCGGTCATAGCTGTATTTTCACCGTAAGTGGCACCAGCTCTTGTT

GCCCCTTCCCTGAGGCCGTTGCGTGTGGTGATGGACACCATTGTTGCCCC

AGGGGCTTTCACTGCTCCGCTGATGGGCGATCTTGCTTTCAGCGGAGTGG

TAACAACTCCGTTGGAGCTATTCAGTGCCCTGACTCCCAATTCGAATGTC

CGGATTTCTCAACGTGTTGTGTGATGGTTGACGGCTCTTGGGGTTGCTGC

CCAATGCCTCAGGCAAGTTGTTGCGAGGACCGAGTCCATTGTTGTCCACA

TGGTGCTTTCTGCGATCTCGTCCACACCCGATGCATTACACCAACAGGGA

CGCACCCGTTGGCAAAGAAACTCCCTGCGCAAAGAACTAATCGCGCAGTT

GCGCTTTCTAGCAGCGTTATGTGCCCGGATGCGCGGAGTCGCTGTCCTGA

TGGTTCAACTTGTTGCGAACTCCCGTCAGGCAAATACGGATGCTGCCCTA

TGCCAAATGCGACATGTTGCTCAGACCATCTTCATTGTTGTCCCCAGGAT

ACCGTATGTGACTTGATTCAGAGCAAGTGTTTGTCCAAAGAGAACGCGAC

CACGGATCTTCTCACCAAGCTCCCGGCACACACGGTCGGCGATGTGAAAT

GTGACATGGAGGTCTCCTGCCCAGATGGCTACACGTGCTGTCGGTTGCAG

TCAGGGGCCTGGGGCTGTTGTCCATTCACCCAGGCTGTTTGCTGTGAAGA

TCATATCCATTGTTGTCCAGCGGGATTTACGTGTGACACTCAAAAAGGCA

CATGCGAGCAAGGACCACACCAGGTTCCTTGGATGGAGAAGGCCCCAGCT

CATCTGTCTCTTCCTGATCCCCAGGCGCTCAAGAGAGACGTTCCTTGCGA

CAACGTTTCCTCATGTCCCTCATCTGACACATGCTGTCAGTTGACGAGCG

GTGAGTGGGGATGCTGTCCAATCCCTGAGGCTGTCTGCTGCTCAGATCAC

CAACATTGCTGCCCACAGGGCTATACATGCGTCGCGGAAGGGCAATGCCA

ACGGGGGAGTGAAATAGTCGCCGGCCTgGAGAAAATGCCCGCGCGCAGGG

CTTCATTGTCTCATCCcCGAGACATTGGCTGCGACCAGCATACGTCCTGC

CCTGTAGGCCAAACTTGTTGCCCCTCCCTGGGTGGATCTTGGGCATGTTG

TCAGCTTCCCCATGCTGTGTGTTGTGAGGATCGACAACATTGTTGCCCTG

CCGGGTACACTTGCAATGTAAAGGCCAGGAGCTGCGAGAAGGAAGTAGTT

TCAGCACAGCCCGCTACGTTTTTGGCTAGGTCACCACACGTCGGGGTAAA

AGACGTTGAGTGCGGCGAGGGTCATTTCTGCCACGATAACCAGACCTGTT

GCAGAGATAATAGACAAGGGTGGGCGTGCTGTCCCTATCGACAAGGAGTG

TGCTGTGCCGATCGGCGCCATTGCTGCCCGGCGGGATTCCGATGCGCAGC

AAGAGGCACTAAATGTTTGCGCCGAGAGGCCCCACGCTGGGATGCCCCGC

TCCGGGACCCCGCTCTTCGGCAGTTGCTGTGA

The CAI of codon-optimised candidate I (PGRN-IDT) is 0.73 and the GC content is 59.33%. This codon-optimised sequence is 76.11% homologous to wildtype.

c) Candidate II (PGRN-GA) artificial codon-optimised PGRN DNA coding sequence (CDS length: 1782 bp) [SEQ ID NO:3]:

ATGTGGACACTGGTGTCTTGGGTTGCCCTGACAGCTGGACTGGTGGCCGG

AACCAGATGTCCTGATGGCCAGTTTTGCCCCGTGGCCTGTTGTCTTGATC

CTGGCGGAGCCAGCTACAGCTGCTGCAGACCTCTGCTGGATAAGTGGCCC

ACCACACTGAGCAGACACCTCGGAGGACCTTGTCAGGTGGACGCCCACTG

TTCTGCCGGCCACAGCTGTATCTTTACCGTGTCTGGCACCTCCAGCTGCT

GTCCATTTCCTGAGGCTGTGGCCTGCGGAGATGGCCACCACTGTTGTCCT

AGAGGCTTCCACTGTAGCGCCGACGGCAGAAGCTGCTTTCAGAGAAGCGG

CAACAATAGCGTGGGCGCCATCCAGTGTCCTGACTCTCAGTTCGAATGCC

CCGACTTCAGCACCTGTTGCGTGATGGTGGATGGCAGCTGGGGCTGTTGT

CCAATGCCTCAGGCTTCCTGCTGCGAGGACAGAGTGCACTGTTGCCCTCA

CGGCGCCTTTTGCGATCTGGTGCACACCCGGTGCATCACCCCAACAGGCA

CACATCCTCTGGCCAAGAAGCTGCCTGCTCAGCGGACCAATAGAGCCGTG

GCTCTGAGCAGCAGCGTGATGTGCCCTGACGCCAGATCTAGATGCCCCGA

TGGCTCCACATGTTGCGAACTGCCCAGCGGCAAATACGGCTGCTGCCCCA

TGCCTAACGCCACATGCTGTAGCGACCATCTTCACTGCTGCCCACAAGAT

ACCGTGTGCGACCTGATCCAGAGCAAGTGCCTGAGCAAAGAGAACGCCAC

CACCGACCTGCTGACCAAACTGCCAGCTCACACCGTGGGCGACGTGAAGT

GCGACATGGAAGTGTCTTGCCCCGACGGCTATACCTGCTGTAGACTGCAA

TCTGGCGCCTGGGGATGCTGCCCTTTTACACAGGCTGTGTGTTGCGAGGA

CCACATCCATTGCTGCCCTGCCGGCTTCACCTGTGACACACAGAAAGGCA

CATGCGAGCAGGGCCCTCATCAGGTGCCATGGATGGAAAAAGCCCCTGCT

CACCTGAGCCTGCCTGATCCTCAAGCTCTGAAGAGGGACGTGCCCTGCGA

CAATGTGTCTAGCTGCCCCTAGCAGCGACACATGCTGCCAGCTGACATCTG

GCGAATGGGGCTGCTGTCCTATACCAGAGGCCGTGTGTTGTAGCGATCAC

CAGCACTGCTGTCCCCAAGGCTACACCTGTGTGGCCGAAGGCCAATGTCA

ACGGGGCTCTGAAATCGTGGCCGGCCTGGAAAAAATGCCCGCCAGAAGGG

CCTCTCTGTCTCACCCTAGAGACATCGGCTGCGACCAGCACACATCTTGT

CCTGTGGGCCAGACCTGTTGTCCCTCTCTTGGTGGATCTTGGGCCTGCTG

TCAGCTGCCTCATGCCGTGTGCTGCGAAGATAGACAACATTGCTGTCCCG

CTGGCTACACATGCAACGTGAAGGCCAGATCCTGCGAGAAAGAAGTGGTG

TCTGCCCAGCCTGCCACCTTCCTGGCTAGAAGTCCTCACGTGGGCGTGAA

GGATGTGGAATGTGGCGAGGGCCACTTCTGCCACGACAATCAGACATGCT

GCAGAGACAACCGGCAAGGCTGGGCTTGCTGCCCATATAGACAGGGCGTG

TGCTGTGCCGACAGAAGGCACTGTTGTCCAGCCGGCTTTAGATGTGCCGC

CAGGGGCACAAAGTGTCTGAGAAGAGAAGCCCCTAGATGGGACGCCCCTC

TGAGAGATCCTGCTCTGAGACAGCTGCTCTGA

The CAI of codon-optimised candidate II (PGRN-GA) is 0.9 and the GC content is 56.23%. The codon-optimized sequence is 78.81% homologous to wildtype.

d) Candidate III (PGRN-GS) artificial codon-optimised PGRN DNA coding sequence (CDS length: 1782 bp) [SEQ ID NO:4]:

```
ATGTGGACTCTGGTCTCCTGGGTCGCTCTGACCGCTGGCCTGGTCGCTGG

GACAAGATGCCCCGATGGACAGTTTTGCCCCGTCGCTTGCTGTCTGGACC

CAGGAGGAGCCAGCTACTCCTGCTGTCGGCCACTGCTGGATAAGTGGCCC

ACCACACTGTCCCGCCACCTGGGAGGACCATGCCAGGTGGACGCACACTG

TTCCGCCGGACACTCTTGCATCTTCACAGTGTCTGGCACCAGCTCCTGCT

GTCCATTTCCTGAGGCAGTGGCATGCGGCGACGGACACCACTGCTGTCCC

AGGGGCTTCCACTGTAGCGCCGATGGCAGGTCCTGCTTTCAGAGAAGCGG

CAACAATTCCGTGGGCGCCATCCAGTGTCCTGACAGCCAGTTCGAATGCC

CAGATTTTTCCACCTGCTGCGTGATGGTGGACGGCTCTTGGGGCTGCTGT

CCAATGCCACAGGCCAGCTGCTGTGAGGACAGGGTGCACTGCTGTCCTCA

CGGAGCCTTCTGTGATCTGGTGCACACACGCTGCATCACCCCCACAGGCA

CCCACCCTCTGGCCAAGAAGCTGCCAGCACAGAGGACCAACAGGGCAGTG

GCCCTGAGCAGCAGCGTGATGTGCCCCGACGCCAGGTCTAGATGCCCTGA

TGGCAGCACCTGCTGTGAGCTGCCAAGCGGCAAGTACGGCTGCTGTCCTA

TGCCAAACGCCACATGCTGTTCCGACCACCTGCACTGCTGTCCTCAGGAC

ACCGTGTGCGATCTGATCCAGTCTAAGTGCCTGAGCAAGGAGAATGCCAC

CACAGACCTGCTGACAAAGCTGCCTGCCCACACCGTGGGCGACGTGAAGT

GTGATATGGAGGTGTCCTGCCCAGATGGCTATACATGCTGTAGGCTGCAG

TCTGGAGCATGGGGATGCTGTCCCTTCACCCAGGCCGTGTGCTGTGAGGA

CCACATCCACTGCTGTCCTGCCGGCTTTACATGTGATACCCAGAAGGGCA

CATGCGAGCAGGGCCCTCACCAGGTGCCATGGATGGAGAAGGCACCAGCA

CACCTGTCCCTGCCCGACCCTCAGGCCCTGAAGAGAGACGTGCCTTGTGA

TAACGTGTCTAGCTGCCCATCCTCTGATACATGCTGTCAGCTGACCTCTG

GCGAGTGGGGCTGCTGTCCAATCCCCGAGGCCGTGTGCTGTAGCGACCAC

CAGCACTGCTGTCCTCAGGGCTATACCTGCGTGGCAGAGGGACAGTGCCA

GAGGGGCTCCGAGATCGTGGCAGGCCTGGAGAAGATGCCAGCCAGGAGAG

CCTCTCTGAGCCACCCCAGAGACATCGGCTGTGATCAGCACACAAGCTGC

CCAGTGGGACAGACCTGCTGTCCATCCCTGGGAGGCTCTTGGGCATGCTG

TCAGCTGCCTCACGCCGTGTGCTGTGAGGATAGGCAGCACTGCTGTCCAG

CCGGCTACACATGCAATGTGAAGGCCAGATCCTGCGAGAAGGAGGTGGTG

TCTGCCCAGCCAGCCACCTTCCTGGCACGCAGCCCTCACGTGGGCGTGAA

GGACGTGGAGTGTGGCGAGGGCCACTTTTGCCACGACAACCAGACATGCT

GTAGGGATAATAGACAGGGCTGGGCCTGCTGTCCATATAGGCAGGGCGTG

TGCTGTGCAGATCGGCGCCACTGCTGTCCAGCAGGCTTTCGGTGCGCAGC

CAGGGGCACCAAGTGCCTGCGCAGAGAAGCCCCCCGGTGGGACGCCCCCC

TGCGAGACCCCGCCCTGAGACAGCTGCTGTGA
```

The CAI of codon-optimised candidate III (PGRN-GS) is 0.92 in human and 0.94 in mouse. The GC content of candidate 3 is 63.23%. The codon-optimised sequence is 81.34% homologous to wildtype.

A schematic diagram of candidates I, II, III of the codon optimised hPGRN by different company algorithms is shown in FIG. 2a.

Each of candidates I to III and the wild type coding sequence (SEQ ID NO:s 1 to 4) encodes the amino acid sequence of progranulin (SEQ ID NO:16):

```
MWTLVSWVALTAGLVAGTRCPDGQFCPVACCLDPGGASYSCCRPLLDKWP

TTLSRHLGGPCQVDAHCSAGHSCIFTVSGTSSCCPFPEAVACGDGHHCCP

RGFHCSADGRSCFQRSGNNSVGAIQCPDSQFECPDFSTCCVMVDGSWGCC

PMPQASCCEDRVHCCPHGAFCDLVHTRCITPTGTHPLAKKLPAQRTNRAV

ALSSSVMCPDARSRCPDGSTCCELPSGKYGCCPMPNATCCSDHLHCCPQD

TVCDLIQSKCLSKENATTDLLTKLPAHTVGDVKCDMEVSCPDGYTCCRLQ

SGAWGCCPFTQAVCCEDHIHCCPAGFTCDTQKGTCEQGPHQVPWMEKAPA

HLSLPDPQALKRDVPCDNVSSCPSSDTCCQLTSGEWGCCPIPEAVCCSDH

QHCCPQGYTCVAEGQCQRGSEIVAGLEKMPARRASLSHPRDIGCDQHTSC

PVGQTCCPSLGGSWACCQLPHAVCCEDRQHCCPAGYTCNVKARSCEKEVV

SAQPATFLARSPHVGVKDVECGEGHFCHDNQTCCRDNRQGWACCPYRQGV

CCADRRHCCPAGFRCAARGTKCLRREAPRWDAPLRDPALRQLL
```

1.2. Generation of PGRN-Fusion Candidates

Because PGRN is a secretory protein, the 5' guide sequence is important for secretion signalling. It was hypothesised that the RNA sequence might have a critical role in guiding the mRNA to the Endoplasmic Reticulum for translation. Therefore, the 5' region of the codon-optimised sequence was replaced with the wild-type 5' GRN sequence (392 bp) upstream of the codon-optimised protein coding sequence using the Bamh1 and BstB1 restrictions sites. This generated pAAV-CMV-PGRN-IDT-Fusion, pAAV-CMV-PGRN-GA-Fusion, and pAAV-CMV-PGRN-GS-Fusion.

FIG. 2b) is a schematic diagram of a fusion plasmid for the three codon optimised candidates in which the 5' sequence from the codon-optimised sequence has been replaced with the 5' sequence from wild-type human PGRN.

1.3. Full Characterisation of Codon-Optimised and PGRN Fusion Candidates

The expression levels of codon-optimised PGRN were compared to wild-type human PGRN. Levels of secreted PGRN were directly measured in the cell culture medium and cellular lysates and normalised to cell count as a ratio to the house keeping protein GAPDH. To directly compare the relative efficiency of PGRN production per PGRN cassette, the copy number of vector genomes per cell was quantified by quantitative qPCR of CMV as a ratio of the same house-keeping gene GAPDH (CMV/GAPDH), which represents effective HEK-293 cell transduction. This was used as the denominator to normalise and accurately quantify the levels of PGRN per cassette.

A human kidney cell line (HEK-293) line was maintained at 37° C. in a humidified chamber with $CO_2$ (5%) and kept in Dulbecco's Modified Medium (DMEM, Thermo Scientific) supplied with 10% Fetal Bovine Serum and 1% penicillin-streptomycin. The cells were passaged every third day.

HEK-293 cells were transfected at 80% confluency in a 24 well plate for Western blot using lipofectamine 2000 (Life Technologies) according to manufacturer's protocol. A total of 250 ng of DNA was transfected or co-transfected in 40,000 cells. pAAV-CMV-EGFP or pAAV-Syn-EGFP were used as transfection efficiency controls. To check the secretion levels of PGRN, the medium was changed to non-serum containing medium which is supplemented with insulin transferrin selenium (ITS) the following day. 48 hours later, the medium was collected and immediately used for western blot analysis. The cells were lysed with mild lysis buffer (NP40) then centrifuged at 10,000×g for 10 min. The supernatant of transfected wells is collected to be used in PGRN ELISAs, and the pellets are stored in −80 C for genomic DNA extraction.

Protein samples were loaded on pre-cast NuPage® Novex™ 10% Bis-Tris Midi gels with MOPS SDS running buffer (Thermo Fisher) and run at constant 100V. Gels were briefly soaked in NuPage Transfer Buffer (Thermo Fisher) before transferring the protein using an iBlot 2™ (Thermo Fisher). Blocking reagent (Roche, 10%) containing Phosphate-buffered saline (PBS) was used to block the protein membranes for an hour. Afterwards, the membrane was incubated in primary antibody diluted in 5% blocking buffer overnight at 4° C. After washing three times with Tris buffered saline with Tween 20 (TBS-T), membranes were incubated with secondary antibodies for an hour. After three washes, membranes were scanned on Odyssey® CLx infrared imaging system (Li-Cor® Biosciences). The intensities of each band of proteins was measured using ImageJ and ImageStudio™-light. Primary antibodies used for western blotting detection were GRN (Abcam, ab191211) and GAPDH (Abcam, ab82485). Secondary antibodies used for western blotting detection were goat anti-mouse IgG (H+L) DyLight® 680/800 conjugate (Thermo Fisher, 25518, SA535521, 1:5,000) and goat anti-rabbit (H+L) DyLight 680/800 conjugate (Thermo Fisher, 35568, SA535571, 1:5, 000).

Western blots of PGRN in the medium showed that the low CAI candidate I (IDT) exhibited significantly decreased expression (see FIG. 3a). However, PGRN expression and secretion of the high CAI candidates II (GA) and III (GS) were equivalent to, or higher than, wild-type PGRN. Three biological replicates were tested and performed in four independent experiments. PGRN-GS significantly increased PGRN expression by 72% compared to wild-type (p=0.0327).

Several "fusion constructs" were also tested. These fusion constructs retained the wild-type genomic signalling sequence and flanking region until the BstB1restriction site fused with codon-optimised PGRN sequence (see FIG. 2b, in yellow). Unfortunately, PGRN protein secretion by PGRN-Fusion cassettes was similar to or lower than wild-type PGRN (see FIGS. 3a and 3b). The initial conclusion was that the 392 bp 5' generic flanking DNA sequence of wild-type PGRN did not significantly improve codon optimised PGRN secretion under the CMV promoter alone. However, subsequent results have shown that expression of the fusion constructs was enhanced when combined with a 5' intronic enhancing sequence (see below).

Western blots of HEK cell lysates showed similar results to secreted PGRN as the codon optimised PGRN-GA and GS improved PGRN expression by 39.55% (not significant) and 127.7% (p=0.0014) respectively. However, PGRN-IDT and other "fusion" constructs again failed to increase PGRN expression (see FIGS. 4a and 4b).

Example 2. Developing an Intronic Enhancing Element to Increase PGRN Expression To further increase PGRN expression and secretion, the addition of introns in the 5' sequence of PGRN was explored to see whether gene expression could be enhanced. Introns can increase transcript levels by affecting the rate of transcription, nuclear export, transcript stability or efficiency of mRNA translation, a phenomenon termed intron-mediated enhancement (IME) (Shaul O. Int J Biochem Cell Biol. 2017 October; 91(Pt B):145-155). A search was carried out for intron sequences smaller than 300 bp that could be uses to test for intron-mediated enhancement. Introns within the human growth hormone (hGH) gene were selected as suitable candidates (see FIG. 5a).

The wild-type GRN sequences were gene synthesised and cloned into pAAV plasmid (Addgene; 99280) using the BamH1 and Xho1 restriction sites. These constructs were used as master vectors (pAAV-CMV-PGRNwt) to sub-clone the previously codon optimised constructs. The human synapsin promoter sequence is replaced from Addgene vector (58881) using the Pci1 and Bamh1 restriction sites for pAAV-Syn-PGRNwt.

The polynucleotide sequence of the synapsin promoter is shown in (SEQ ID NO:15):

```
AGTGCAAGTGGGTTTTAGGACCAGGATGAGGCGGGGTGGGGGTGCCTACC

TGACGACCGACCCCGACCCACTGGACAAGCACCCAACCCCCATTCCCCAA

ATTGCGCATCCCCTATCAGAGAGGGGGAGGGGAAACAGGATGCGGCGAGG

GCGTGCGCACTGCCAGCTTCAGCACCGCGGACAGTGCCTTCGCCCCCCGC

CTGGCGGCGCGCGCCACCGCCGCCTCAGCACTGAAGGCGCGCTGACGTCA

CTCGCCGGTCCCCCGCAAACTCCCCTTCCCGGCCACCTTGGTCGCGTCCG

CGCCGCCGCCGGCCCAGCCGGACCGCACCACGCGAGGCGCGAGATAGGGG

GGCACGGGCGCGACCATCTGCGCTGCGGCGCCGGCGACTCAGCGCTGCCT

CAGTCTGCGGTGGGCAGCGGAGGAGTCGTGTCGTGCCTGAGAGCGCAG
```

The intronic sequence of human growth hormone (hGH1) was used to improve PGRN expression. hGH1 is composed of four introns which were synthesised by GenScript and cloned into pAAV-CMV-PGRN plasmids using the BamH1 and Age1 restriction sites to generate pAAV-CMV-hGHi1-PGRN, pAAV-CMV-hGHi2-PGRN, pAAV-CMV-hGHi3-PGRN and pAAV-CMV-hGHi4-PGRN. Structural elements are important for intron-mediated enhancement (IME). Therefore, the wild-type PGRN coding sequence was analysed by exonic splice enhancer (ESE)-finder (ESE 3.0, http://krainer01.cshl.edu/cgi-bin/tools/ESE3/esefinder.cgi) and the high frequency of ESE predicted on GRN. To enhance PGRN expression further, the hGHi3 intron was introduced into fusion constructs which preserve the 5' ESE element of wild-type PGRN to generate pAAV-CMV-hGHi3-PGRN-GA-Fusion, and pAAV-CMV-hGHi3-PGRN-GS-Fusion. The Bamh1 and Age1 restriction sites were used to generate the neuron-specific expression construct pAAV-Syn-hGHi3-PGRN-GA-Fusion and pAAV-Syn-hGHi3-PGRN-GS.

SEQ ID NO:5 is the sequence of the human growth hormone intron 1 (261 bp):

```
                                          (SEQ ID NO: 5)
GTAAGCGCCCCTAAAATCCCTTTGGGCACAATGTGTCCTGAGGGGAGAGG

CAGCGACCTGTAGATGGGACGGGGGCACTAACCCTCAGGTTTGGGGCTTC

TGAATGTGAGTATCGCCATGTAAGCCCAGTATTTGGCCAATCTCAGAAAG

CTCCTGGTCCCTGGAGGGATGGAGAGAGAAAAACAAACAGCTCCTGGAGC

AGGGAGAGTGCTGGCCTCTTGCTCTCCGGCTCCCTCTGTTGCCCTCTGGT

TTCTCCCCAG
```

SEQ ID NO:6 is the sequence of the human growth hormone intron 2 (209 bp):

```
                                    (SEQ ID NO: 6)
GTAAGCTCTTGGGGAATGGGTGCGCATCAGGGGTGGCAGGAAGGGGTGAC

TTTCCCCCGCTGGGAAATAAGAGGAGGAGACTAAGGAGCTCAGGGTTTTT

CCCGAAGCGAAAATGCAGGCAGATGAGCACACGCTGAGTGAGGTTCCCAG

AAAAGTAACAATGGGAGCTGGTCTCCAGCGTAGACCTTGGTGGGCGGTCC

TTCTCCTAG
```

SEQ ID NO:7 is the sequence of the human growth hormone intron 3 (92 bp):

```
                                    (SEQ ID NO: 7)
GTGAGTGGATGCCTTCTCCCCAGGCGGGGATGGGGGAGACCTGTAGTCAG

AGCCCCCGGGCAGCACAGCCAATGCCCGTCCTTCCCCTGCAG
```

SEQ ID NO:8 is the sequence of the human growth hormone intron 4 (253 bp):

```
                                    (SEQ ID NO: 8)
GTGAGGGTGGCGCCAGGGGTCCCCAATCCTGGAGCCCCACTGACTTTGAG

AGCTGTGTTAGAGAAACACTGCTGCCCTCTTTTTAGCAGTCAGGCCCTGA

CCCAAGAGAACTCACCTTATTCTTCATTTCCCCTCGTGAATCCTCCAGGC

CTTTCTCTACACCCTGAAGGGGAGGGAGGAAAATGAATGAATGAGAAAGG

GAGGGAACAGTACCCAAGCGCTTGGCCTCTCCTTCTCTTCCTTCACTTTG

CAG
```

The region flanked by the restriction sites Bamh1 and BstB1 (1-392 bp) in pAAV-CMV-PGRNwt and pAAV-CMV-PGRN-GS was used for signalling sequence replacement. The N-terminal region (1-51 bp) of PGRN signalling sequence was substituted with 78 bp of hGH1 for gene synthesis. These were sub-cloned into pAAV-CMV-PGRNwt and pAAV-CMV-PGRN-GS using the Bamh1 and BstB1restriction sites to generate pAAV-CMV-hGHs-PGRNwt and pAAV-CMV-hGHs-PGRN-GS.

SEQ ID NO:9 is the generic DNA signalling sequence of the human growth hormone which replaced the PGRN signalling sequence:

```
                                    (SEQ ID NO: 9)
ATG GCT ACA GGC TCC CGG ACG TCC CTG CTC CTG GCT TTT

GGC CTG CTC TGC CTG CCC TGG CTT CAA GAG GGC AGT GCC
```

SEQ ID NO:10 is a translated amino acid sequence for the generic signalling sequence of the human growth hormone:

MATGSRTSLLLAFGLLCLPWLQEGSA (SEQ ID NO:10)

To test the effect on PGRN expression, hGH introns 2, 3 and 4 sequences were cloned into the 5' UTR region of PGRN-WT (see FIG. 5b). In addition, the wild-type signalling sequence of PGRN was substituted with the hGH signalling sequence (see FIG. 5c).

2.1 Addition of an Intronic Enhancer Element

The efficiency of each hGH intron on PGRN expression and secretion was assessed by western blot (see above for method), which demonstrated that intron 3 greatly increased secreted PGRN (105%, p=0.0004), while intron 4 decreased secretion and intron 2 abolished it (see FIGS. 6a and 6b). Moreover, as shown in FIGS. 6a and 6b, replacing wild-type PGRN signalling peptide with the hGH signalling peptide also showed a significant increase in secreted PGRN (71%, p=0.0088).

The levels of PGRN expression, measured in HEK-293 cell lysates, confirmed that intron 3 significantly increased PGRN expression (148%, p=0.0009) (see FIGS. 7a and 7b), while intron 4 decreased PGRN expression of PGRN by 40% and intron 2 abolished it. As shown in FIGS. 7a and 7b, substituting the wild-type with the hGH signalling sequence increased PGRN expression by 23% which was not significant.

These results suggest that the intron 3 enhances PGRN translation which in turn increased PGRN secretion into the medium. Substituting the signalling peptide for hGH modestly increased PGRN secretion but not expression.

Example 3. Combining Intronic and Exonic Enhancing Elements

To test the intron-mediated enhancement of hGHi3 on codon-optimised PGRN-GS, the hGHi3 element was sub-cloned in the 5' position of PGRN-GS.

Figure 8:
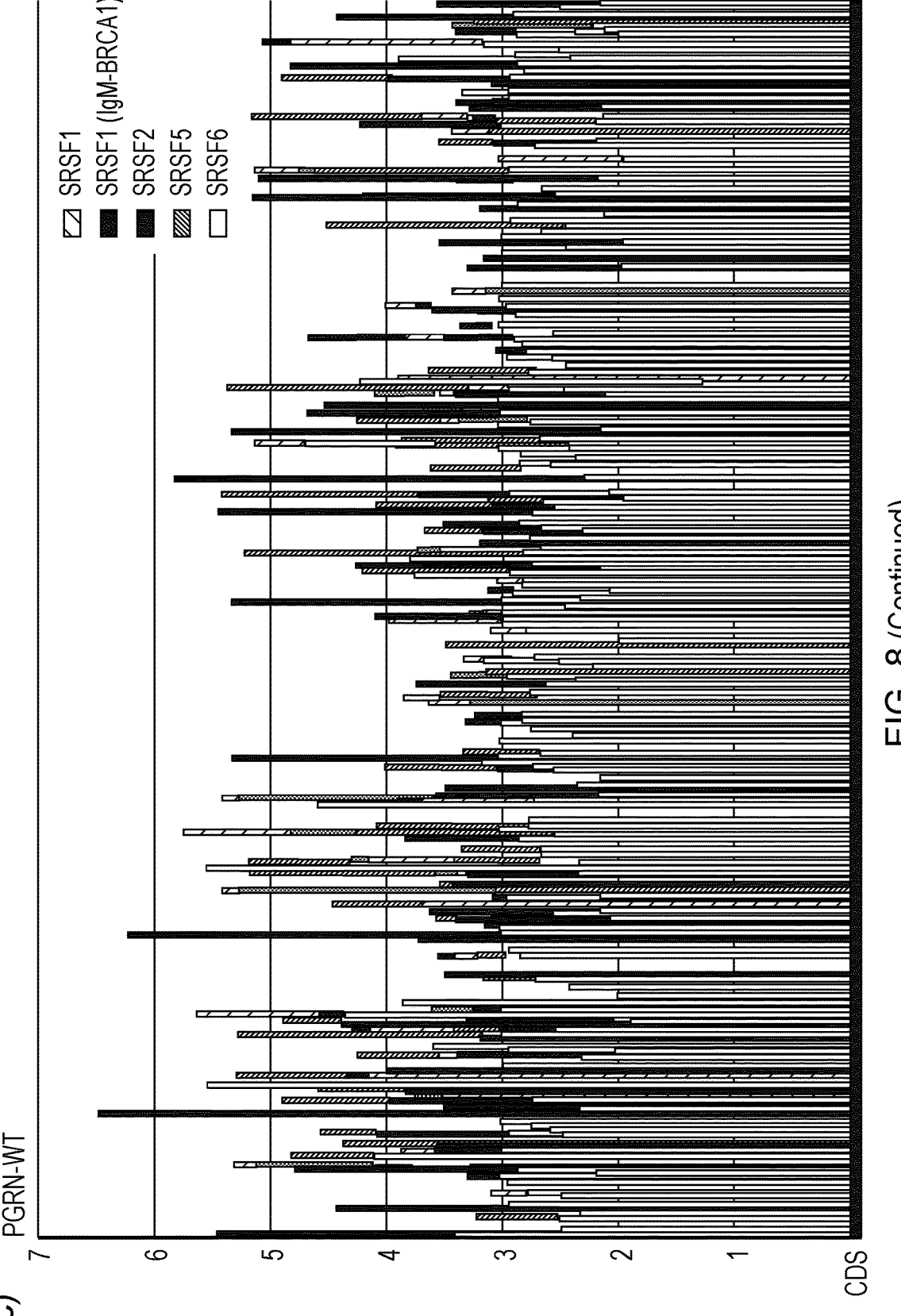
FIG. 8. hGHi3 did not enhance the GRN expression from codon optimised PGRN-GS.
Figure 8:
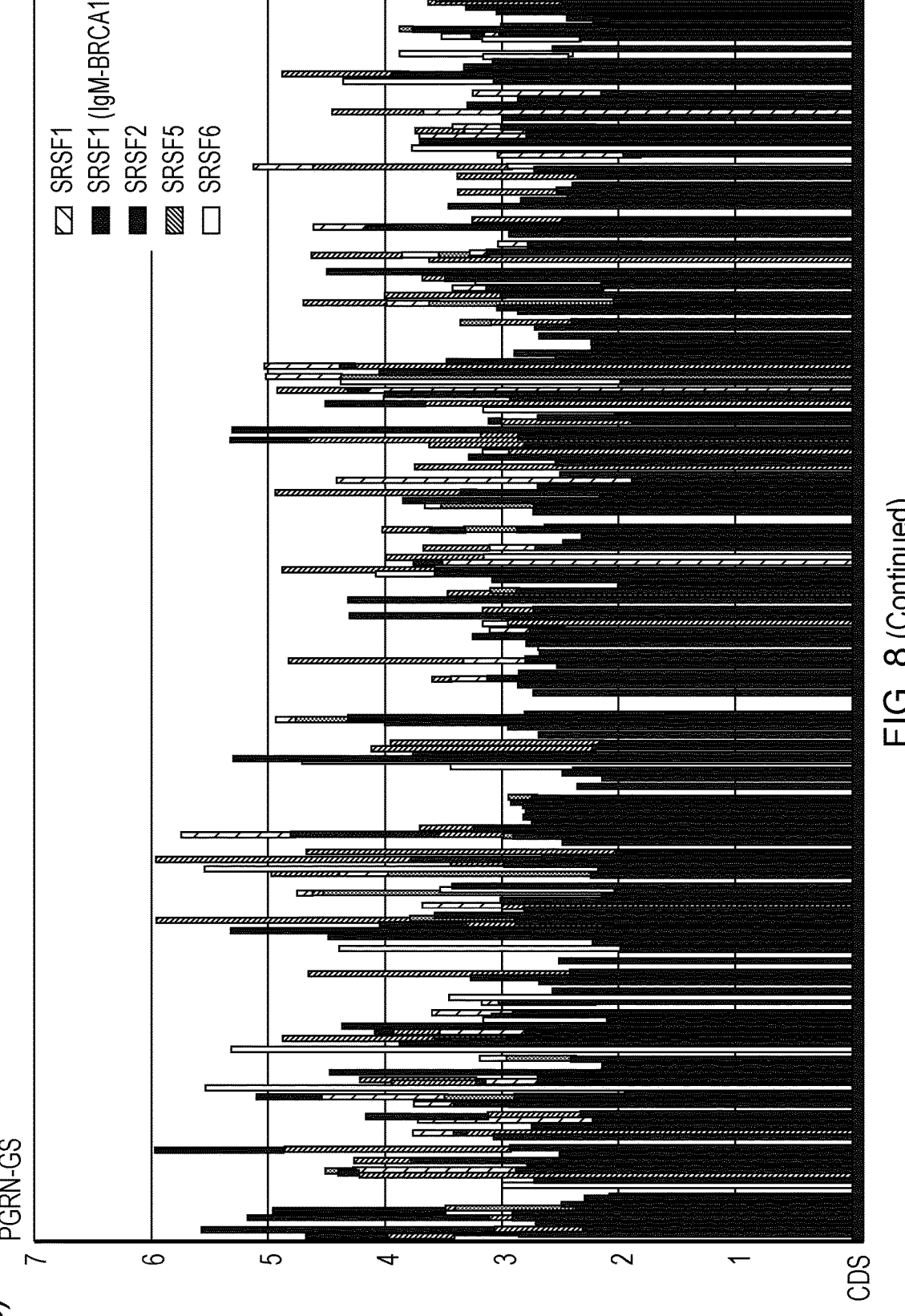

Surprisingly, there was no enhancing effect of hGHi3 on PGRN-GS expression (see FIGS. 8a and 8b) as the inclusion of intron 3 decreased PGRN modestly. This suggested that the effect of hGHi3 might require an exonic splicing element (ESE) within wildtype PGRN sequence to generate a synergistic effect on splicing. ESE elements in wild type PGRN and codon optimised PGRN-GS sequences were sought using the software ESE finder 3.0 (see FIG. 8c). The ESE distribution pattern in codon optimised PGRN-GS was markedly altered when compared to wild-type PGRN. Thus, efforts to codon optimise PGRN had inadvertently removed the ESEs required to deliver enhancement due to the inclusion of hGHi3.

Figure 9:
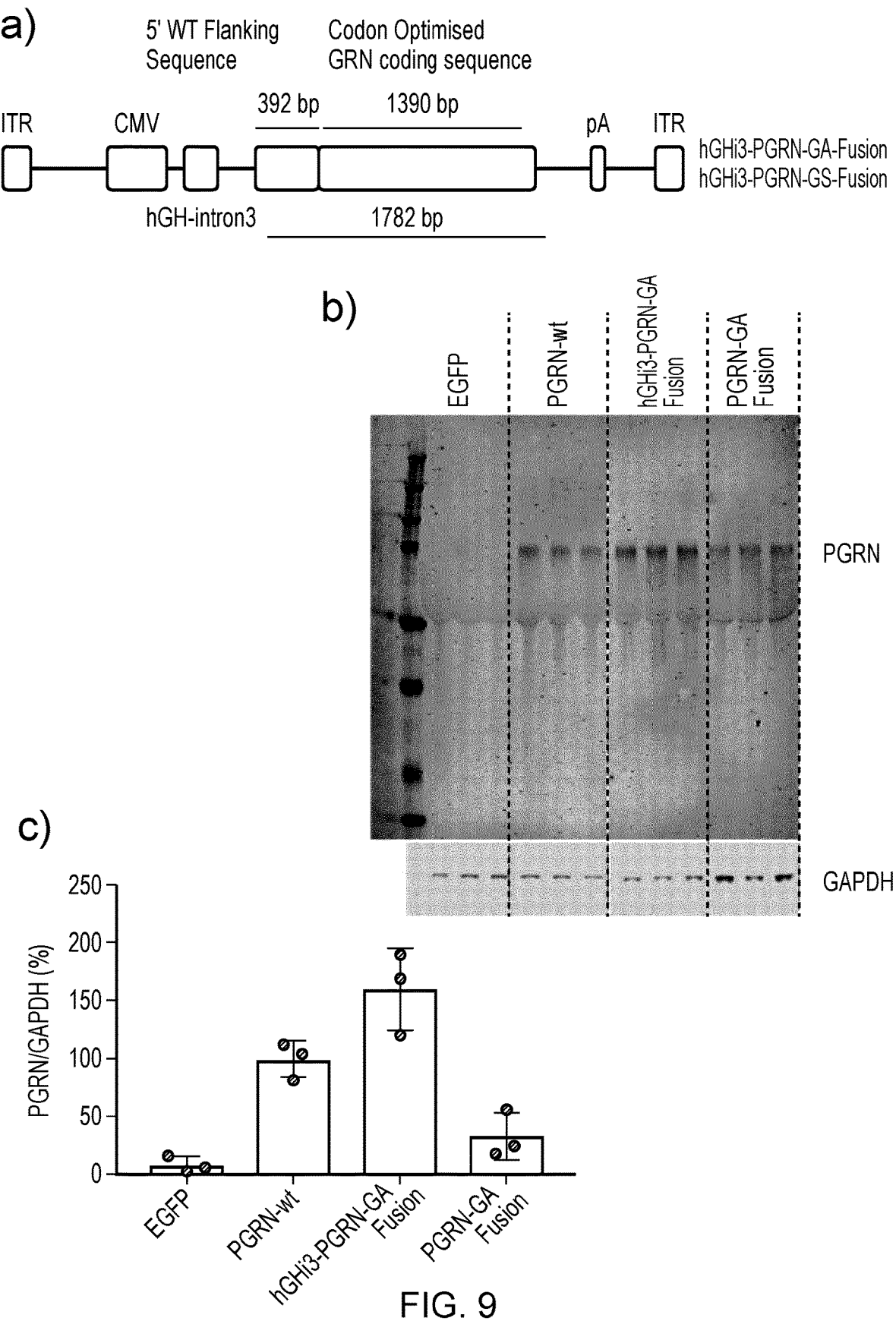
FIG. 9. hGHi3-PGRN-fusion construct enhanced the GRN expression in primary neuron.

As a result, the intronic enhancer, hGHi3 was combined with the PGRN fusion constructs which harboured the initial 392 bp sequence of wildtype GRN fused to PGRN-GA codon optimised sequence (see FIG. 9a). This was packaged into an AAV9 vector and delivered to rat primary cortical neurons in culture at the MOI of 1e6.

The 5' ESE Flanking sequences were as follows:

```
RPL41:
                                    (SEQ ID NO: 11)
CGACACCCGGCGCTCCATTAAATAGCCGTAGACGGAACTTCGCCTTTCTC

TCGGCCTTAGCGCCATTTTTTTGGGTGAGTGTTTTTTGGTTCCTGCGTTG

GGATTCCGTGTACAATCCATAGACATCTGACCTCGGCACTTAGCATCATC

ACAGCAAACTAACTGTAGCCTTTCTCTCTTTCCCTGTAGAAACCTCTGCG

CC;

UCHL1:
                                    (SEQ ID NO: 12)
TTTCCCCCTCGCTTGGTTCTGCCCCTGCTCCCCCTGCACAGGCCTCACAG

TGCGTCTGGCCGGCGCTTTATAGCTGCAGCCTGGGCGGCTCCGCTAGCTG

TTTTTCGTCTTCCCTAGGCTATTTCTGCCGGGCGCTCCGCGAAGG;

RPL38:
                                    (SEQ ID NO: 13)
ACTGCCCGGAAACGGAAGTCTCGTTCTTTTTCGTCCTTTTCCCCGGTTGC

TGCTTGCTGTGAGTGTCTCTAGGGTGATACGTGGGTGAGAAAG.
```

The 5' ESE flanking sequences described above can be used in some embodiments of the present invention. However in the following examples these sequences were not further studied.

For each virus 10×145 cm² plates of low passage (≤P30), HEK-293T cells were used at approximately 80% confluence on the day of transfection. Cells were cultured at 37° C., 5% $CO_2$ in Dulbecco's Modified Eagle Medium (DMEM, Gibco) with 10% heat-inactivated FBS. For the transfection mixture 800 µL of 1 mg/mL PEI was added to 15 mL serum free DMEM. In a separate tube 240 m of Adeno helper plasmid (containing essential genes from the adenoviral genome that support rescue and replication of AAV genomes), 80 µg of Rep2/Cap9 plasmid and 80 µg of single stranded transgene containing plasmid was added to serum free DMEM to a final volume of 30 mL. The mixture containing DNA was then filtered into the PEI-containing mixture through a 0.45 µm of polyethersulphone (PES, Sartorius, Epsom, UK) syringe filter. The solution was mixed and incubated at room temperature for 15 minutes. The transfection solution was then added drop wise to each 145 cm² dish.

The AAV virus particles were harvested after 72 hours of transfection. The soup and pellets were collected and subjected to freeze thaw cycles. All supernatant and pellets were treated with benzonase (50 Unit/mL, 37 C, 30 minutes) then centrifuged at 2000×g for 30 mins at 18° C. The supernatants were filtered with 0.45 µM pore size filter and then applied to a pre-equilibrized AAVX POROS affinity column (Thermo Fisher) on the AKTA system for AAV purification. The purified AAV is kept at −80° C.

Neuronal cells were isolated from cortical tissue at embryonic day 18 (E18) (Sprague-Dawley rat). 100,000 cells were plated on PDL-coated 24-well plates. Cells were grown in Neurobasal media that was supplemented with penicillin/streptomycin (0.5%), Glutamax (1%) and B27 (2%, Thermo Fisher). Cells were transduced with AAV on the day in vitro (DIV) 7 at the multiplicity of infection (MOI) of 1e6. Neurons were harvested on DIV 12 and processed for western blot (see above for methodology) and ELISA.

Genomic DNA was isolated 48 hours post-transfection using DNeasy Blood and Tissue kits (Qiagen) following the manufacturer's protocol. DNA concentrations were measured using Nanodrop™.

The PGRN content of samples was assessed using the Adipogen Life Sciences Progranulin (human) ELISA Kit (AG-45A-0018YEK-KI01). The sandwich ELISA Kit captures human progranulin in the sample with a polyclonal antibody precoated on microtitre plates and detects protein using a second biotinylated polyclonal antibody. A STREP-HRP solution was added to the wells and the PGRN signal was detected by using TMB substrate for 10 minutes, adding an acidic stop solution and measuring the absorbance of each well at 450 nm. The concentration of PGRN was calculated within a range of 0.063-4 ng/ml using a recombinant human PGRN standard. The standard and all other reagents required for the assay were included within the kit.

As shown in FIGS. 9b and 9c, PGRN secretion by cortical neurons transduced by the hGHi3-PGRN-GA construct was greater than that of hGHi3-wild type PGRN alone.

These results demonstrate that the increase in expression and secretion generated by hGHi3 is because hGHi3 is acting as an intronic splicing element (ISE). Preferably hGHi3 works in combination with an exonic splicing element (ESE) which is present in the initial 392 bp sequence of wild-type PGRN. Thus, hGHi3 is likely to harbour a cryptic ISE sequence, which may require an ESE present in wild-type PGRN sequence to enhance splicing (McCarthy and Philips (1998) *Human Molecular Genetics.* 7; 1491-1496). Without wishing to be bound by theory, the predicted mechanism is that this combination facilitates the binding of serine and arginine rich (SR) splicing proteins which accelerates RNA processing and subsequent translation.

Example 4. Restricting Expression Using the Neuronal-Specific Promoter Synapsin PGRN is used by many cell types. However, in the brain, its expression and secretion are largely determined by microglia and neurons and both cell types are affected by PGRN deficiency. Microglia are very difficult to transduce using viral vectors, so the focus was on maximising the transduction and expression of PGRN into post mitotic neurons, which also avoids the risk of accelerating cell division in microglia and astrocytes by PGRN which could be carcinogenic. Wild-type PGRN expression under the pan-mammalian generic promoter CMV was compared to the human neuron-specific promoter synapsin. As shown in FIG. 10, expression was restricted and PGRN secretion was significantly increased in rat cortical neuron cultures with the synapsin promoter.

Figures 11, 12:
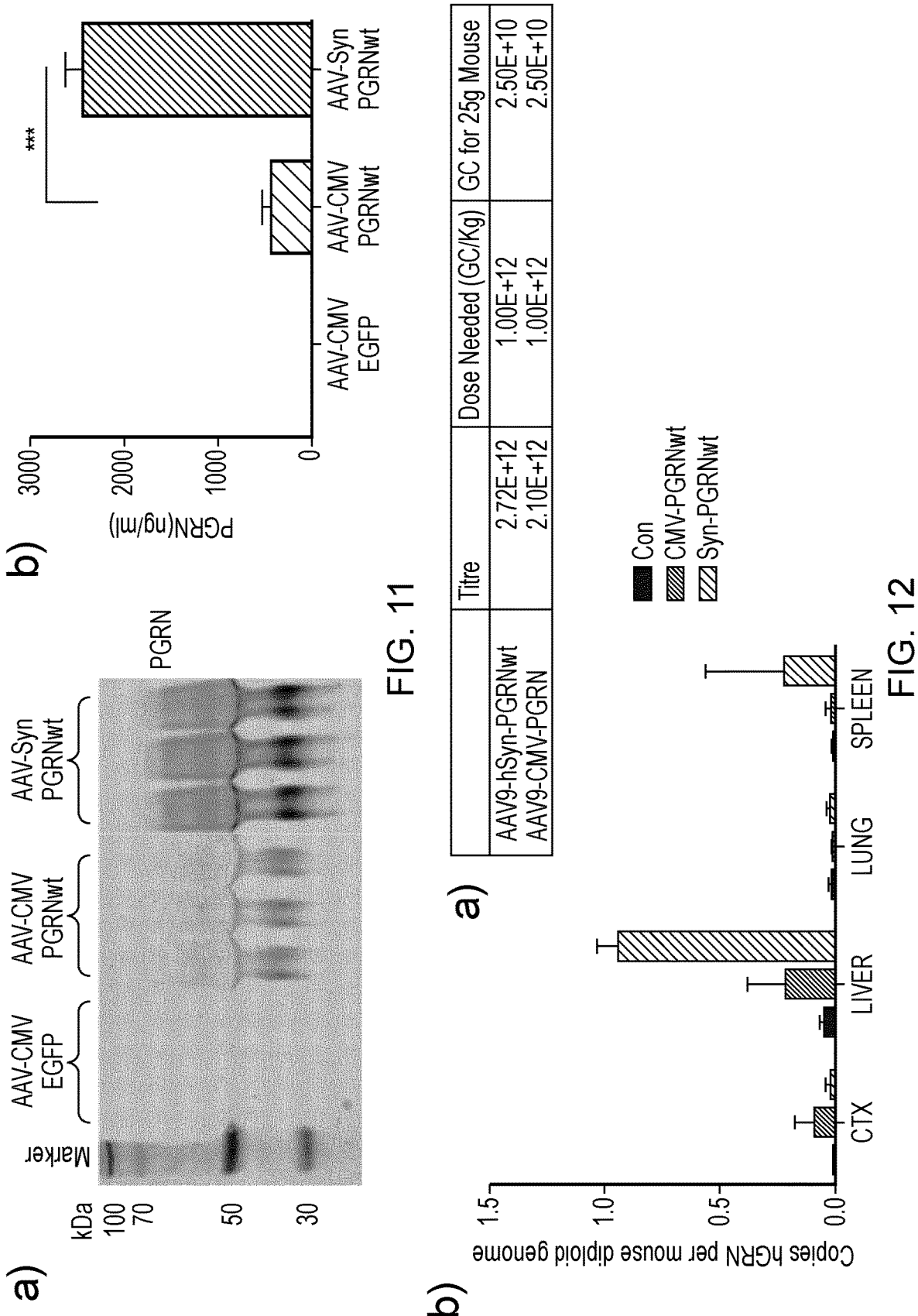
FIG. 11. AAV9 carrying Syn-PGRNwt enhanced the PGRN expression in cultured rat neurons.
FIG. 12. Biodistribution of the AAV9-PGRN transduction in mouse organs.

To test whether packaging of the PGRN cassette in the AAV9 vector supported the initial findings from plasmid transfection, AAV9 carrying either CMV-PGRNwt or Syn-PGRNwt was generated. Rat primary cortical neurons were cultured for seven days and transduced with AAV9-GRN vectors. After five days the cell culture medium was sampled and processed by Western blot. The synapsin promoter increased GRN expression by 5.4-fold compared to CMV, which was confirmed by PGRN ELISA (see FIG. 11).

In order to validate these studies in vivo, AAV9-CMV-PGRNwt and AAV9-Syn-PGRN vectors were injected via bilateral intra-cerebroventricular (ICV) into 8-week old C57BL\6J male mice (FIG. 12a). Mice were deeply anaesthetized with isoflurane and immobilised in a stereotaxic frame installed with a digital stereotaxic control panel. Mice were injected bilaterally in the anterior ventricle or the posterior thalamus using a Hamilton syringe. Each mouse received 3 µL of total dose of 5e+10 VG, infused at a rate of 0.5 µL/min with 2 minutes wait time post-infusion prior to withdrawal of the trochanter. Mice were injected at 8 weeks of age and sacrificed 4 weeks post-injection at 12 weeks of age. Half of the brain and spinal cord, spleen, heart, liver, kidney, lung, testes, blood and cerebrospinal fluid (CSF) were harvested and freshly frozen in liquid nitrogen. The other half of the brain was paraformaldehyde (PFA) post-fixed and processed for histology and immunocytochemistry (IHC).

For brain, plasma and organ collection, the mice were anesthetised with pentobarbital (100 mg/kg, Fatal Plus, Vortech Pharmaceuticals, Dearborn, MI) and blood was collected by cardiac puncture in syringes containing EDTA (250 mM) to prevent clotting. The blood was kept on ice and later centrifuged at 1000×g for 10 minutes at 4° C. to separate plasma. The mice were then transcardially perfused with PBS. Brains were removed and bisected into hemispheres, one of which was micro dissected into prefrontal cortex, striatum, hippocampus, cerebellum, subcortical regions and cortices and flash-frozen in liquid nitrogen for biochemical analysis, and one of which was post-fixed for 24 hours in 4% paraformaldehyde for histological analysis. Spinal cord, spleen, heart, liver, kidney, lung, testes, blood and cerebrospinal fluid were removed and frozen immediately in liquid nitrogen for ELISA and western blot analysis.

The distribution and quantification of CMV-PGRN and Syn-PGRN transduction in each tissue was measured by amplifying human PGRN from genomic DNA by qPCR. Genomic DNA was diluted to 7.5 ng/ul in nuclease-free H₂O. qPCR was carried out using the Powerup™ SYBR® Green Master Mix following a standard protocol. For each set of reactions, a standard curve was also run using known concentrations of DNA.

Fixed hemispheres were cryoprotected in 30% sucrose and cut into 30 μm sections on a sliding microtome (Leica Biosystems). The sections were then immunostained. For analysis of pathology and a qualitative assessment of progranulin immunoreactivity, the sections were incubated overnight in primary antibody (PGRN, markers for neurons (NeuN) or microglia (Iba1)) and, the following day, were incubated with a species-matched secondary antibody AlexaFluor®-488-conjugated antibody for PGRN and species matched AlexaFluor-647-conjugated antibodies for NeuN and Iba1.

Low magnification, high resolution images of progranulin immunostaining were obtained with a slide scanner (Olympus VS120) for image analysis.

Low levels of CMV-PGRN and Syn-PGRN were detected in cerebral cortex, lung and spleen. However, a relatively high copy number of the virus was detected in the liver (see FIG. 12).

Figure 13:
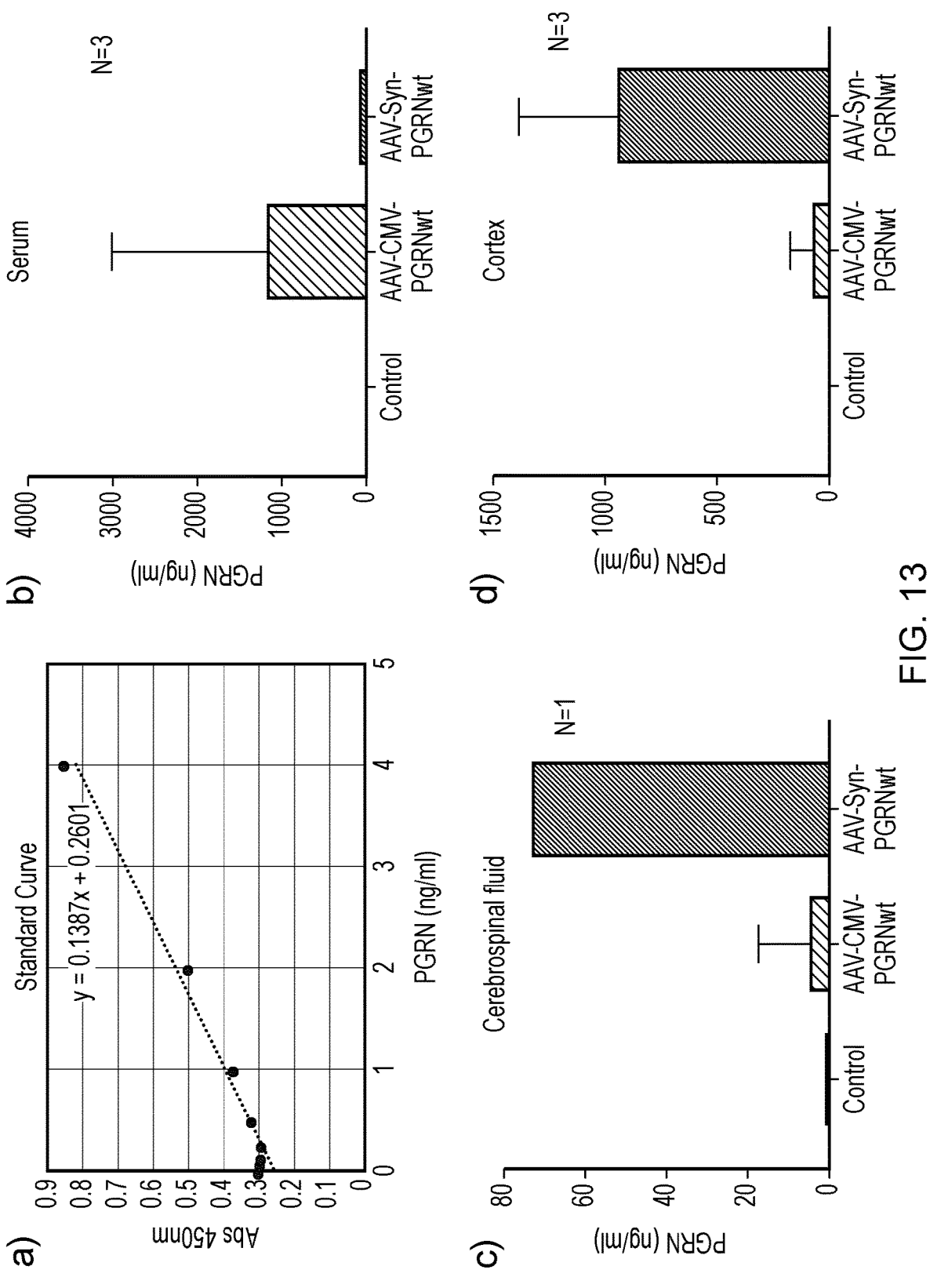
FIG. 13. AAV9 carrying Syn-PGRNwt enhanced the PGRN expression in mouse cortex. AAV9 vectors carrying CMV-PGRN-WT and Syn-PGRN-WT were delivered by bilateral ICV injection (1E+12 GC/Kg).

ELISA was used to quantify PGRN expression levels from serum, CSF and cortical tissue of transduced mice. Mice injected with AAV9-CMV-PGRN showed high serum PGRN levels which was almost undetectable in AAV9-Syn-PGRN injected mice (see FIG. 13). Conversely, PGRN levels in the cortex and CSF were much higher in AAV9-Syn-PGRN compared to AAV9-CMV-PGRN injected mice (see FIGS. 13c and 13d), confirming the neuronal specificity of synapsin in vivo.

Figure 15:
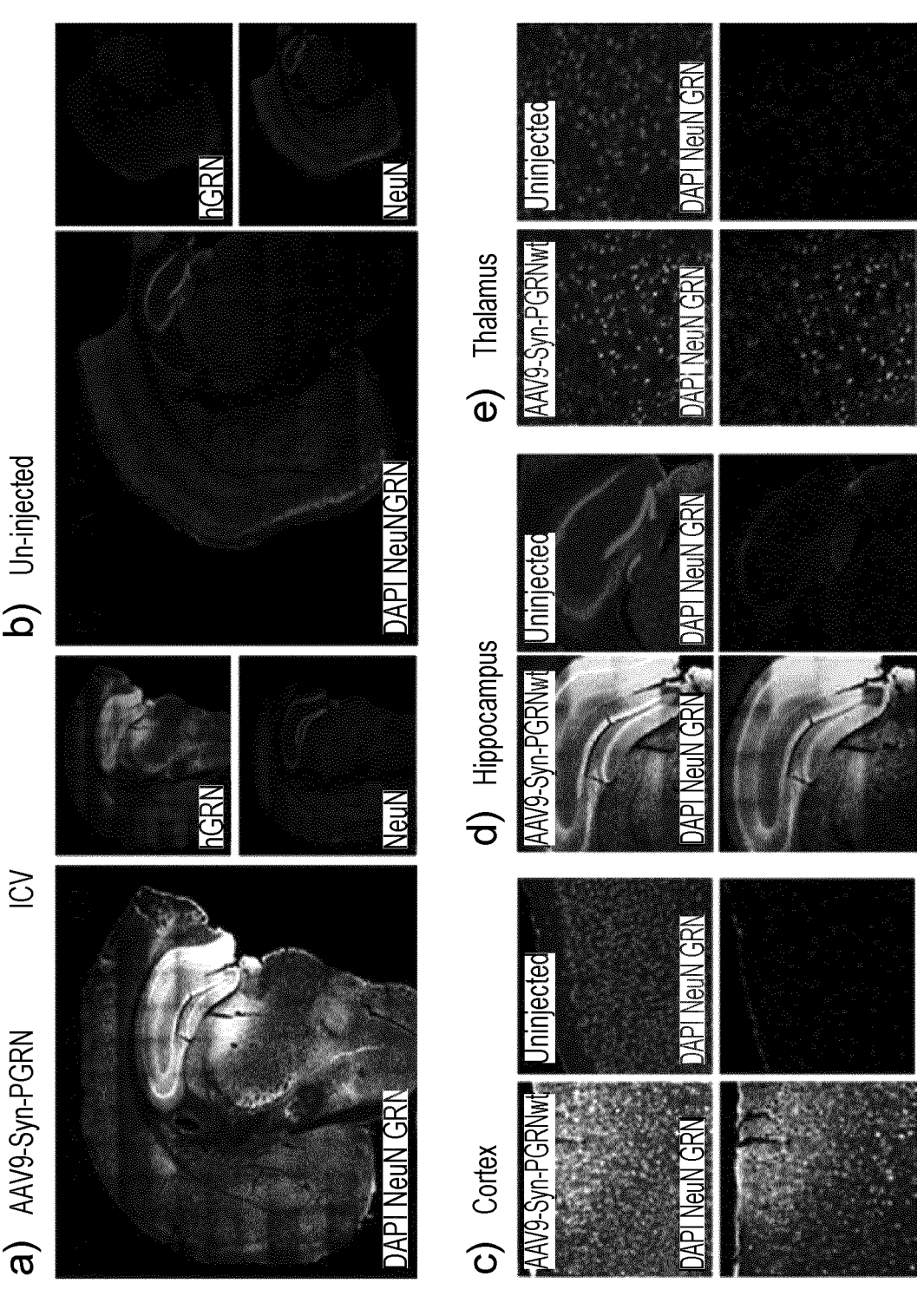
FIG. 15. ICV delivery of AAV9-Syn-PGRNwt showing wide distribution of PGRN in mouse brain. a) The 4 weeks old mouse brain slice were used for IHC to detect the human GRN expression. The images were taken by Nikon MR confocal. To reconstitute the whole brain image, the scanned images were stitched by 20% overlapping in automatic setting in NIC software. Human GRN (green), NeuN (red). b) Un-injected brain slices were subjected to IHC, which show no GRN detection. c) Cortex, d) hippocampus, e) Thalamus.
Figure 16:
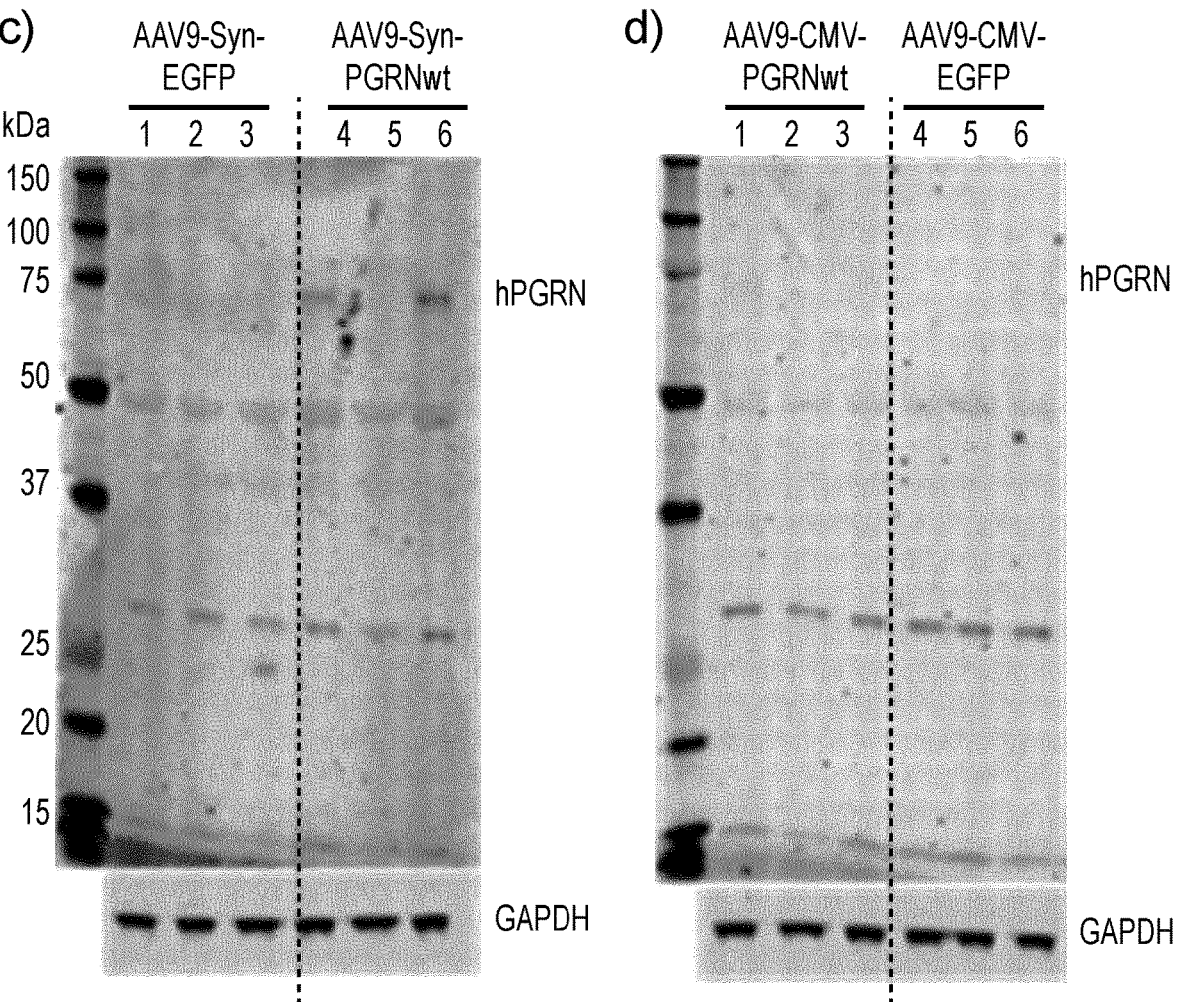
FIG. 16. AAV9 carrying Syn-PGRNwt enhanced the PGRN expression in mouse hippocampus. AAV9 vectors carrying CMV-PGRN-WT and Syn-PGRN-WT were delivered by bilateral ICV injection (2.5E+10). a) Commercial ELISA kit (Adipogen) was use for the quantitative analysis of PGRN expression levels in the serum, CSF and cortex. b) PGRN ELISA for AAV9-Syn-EGFP, AAV9-Syn-PGRNwt, AAV9-CMV-EGFP, and AAV9-CMV-PGRNwt (N=3) c) PGRN Western blot for AAV9-Syn-EGFP and AAV9-Syn-PGRNwt. The PGRN is detected around 68 kDa only from AAV9-Syn-PGRNwt injected hippocampal lysate. d) PGRN western blot for AAV9-CMV-EGFP and AAV9-CMV-PGRNwt FIG. 17. Schematic diagram of Syn-hGHi3-PGRN-GS-UTR a). Schematic diagram of the Syn promoter driven PGRN codon optimised construct, which is composed of hGH3 intron3 and 3'UTR. b). DNA sequence for human PGRN-UTR.

Example 5. Widespread PGRN Expression of AAV9-Syn-PGRNwt after ICV Injection Mice injected with AAV9-Syn-PGRN-wt via ICV injection were harvested after 4 weeks (FIG. 15). Post PFA fixed brains were sliced and used for IHC. The goat anti-human specific PGRN antibody (green) showed widespread GRN expression in the cortex (FIG. 15c), hippocampus (FIG. 15d) and thalamus (FIG. 15e). The rabbit anti-neuron-specific antibody NeuN was used for counter staining. No human PGRN was detected in un-injected mice brain tissues, whereas intense staining in the hippocampus, and to a lesser extent the thalamus and cortex of mice that were injected with AAV-Syn-PGRNwt (FIG. 15d). PGRN ELISA of hippocampal tissue lysate confirmed that the Synapsin promoter generated a 3-fold increase in PGRN expression over the CMV promoter (FIG. 16b). The western blot confirms that the strong PGRN band detected at around 68 kDA (FIG. 16c, d).

Example 6. Combining Intronic Sequence hGHi3 and 3' UTR Elements

We then tested whether the 3' UTR could be used as an exonic enhancing element (ESE) to enhance and potentially regulate PGRN expression. We synthesized 284 bp of the wild type PGRN 3' UTR and cloned into the 3' region in addition to the intronic enhancer, hGHi3, and our codon optimised PGRN-GS to generate Syn-hGHi3-PGRN-GS-UTR (FIG. 17).

The 3'UTR sequence (284 bp) of wild type PGRN is shown in FIG. 17b and below (SEQ ID NO:14):

```
GGGACAGTACTGAAGACTCTGCAGCCCTCGGGACCCCACTCGGAGGGTGC

CCTCTGCTCAGGCCTCCCTAGCACCTCCCCCTAACCAAATTCTCCCTGGA

CCCCATTCTGAGCTCCCCATCACCATGGGAGGTGGGGCCTCAATCTAAGG

CCTTCCCTGTCAGAAGGGGGTTGTGGCAAAAGCCACATTACAAGCTGCCA

TCCCCTCCCCGTTTCAGTGGACCCTGTGGCCAGGTGCTTTTCCCTATCCA

CAGGGGTGTTTGTGTGTGTGCGCGTGTGCGTTTC
```

Figure 21:
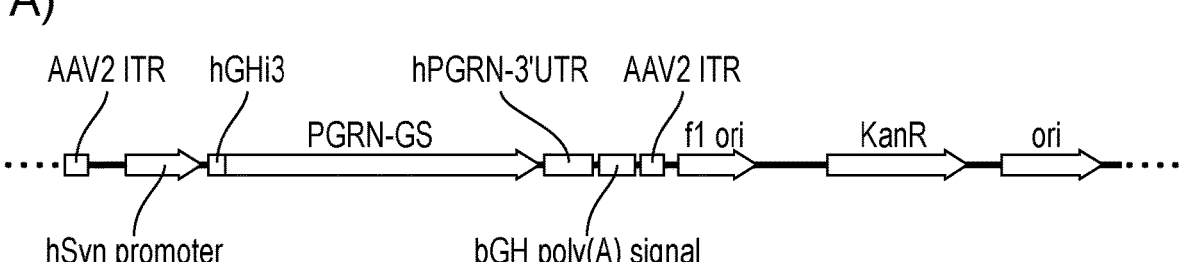

This sequence including 5' PmeI and 3' XhoI was synthesized using gene synthesis service from GenScript. The UTR sequences was cloned into AAV-Syn-hGHi3-PGRN-GS to form AAV-Syn-hGHi3-PGRN-GS-UTR. A vector map showing a plasmid comprising the cassette as shown in FIG. 17 is shown in FIG. 21. The DNA sequence for the Syn-hGHi3-PGRN-GS-UTR vector cassette (from ITR to ITR) is shown below (SEQ ID NO:17).

```
CCTGCAGGCAGCTGCGCGCTCGCTCGCTCACTGAGGCCGCCCGGGCGTCG

GGCGACCTTTGGTCGCCCGGCCTCAGTGAGCGAGCGAGCGCGCAGAGAGG

GAGTGGCCAACTCCATCACTAGGGGTTCCTGCGGCCGCACGCGTTGCAAA

GATGGATAAAGTTTTAAACAGAGAGGAATCTTTGCAGCTAATGGACCTTC

TAGGTCTTGAAAGGAGTGGGAATTGGCTCCGGTGCCCGTCAGTGGGCAGA

GCGCACATCGCCCACAGTCCCCGAGAAGTTGGGGGGAGGGGTCGGCAGCA

AATGGTTAATTAATCTAGACTGCAGAGGGCCCTGCGTATGAGTGCAAGTG

GGTTTTAGGACCAGGATGAGGCGGGGTGGGGGTGCCTACCTGACGACCGA

CCCCGACCCACTGGACAAGCACCCAACCCCCATTCCCCAAATTGCGCATC

CCCTATCAGAGAGGGGGAGGGGAAACAGGATGCGGCGAGGCGCGTGCGCA

CTGCCAGCTTCAGCACCGCGGACAGTGCCTTCGCCCCCGCCTGGCGGCGC

GCGCCACCGCCGCCTCAGCACTGAAGGCGCGCTGACGTCACTCGCCGGTC

CCCCGCAAACTCCCCTTCCCGGCCACCTTGGTCGCGTCCGCGCCGCCGCC

GGCCCAGCCGGACCGCACCACGCGAGGCGCGAGATAGGGGGGCACGGGCG

CGACCATCTGCGCTGCGGCGCCGGCGACTCAGCGCTGCCTCAGTCTGCGG

TGGGCAGCGGAGGAGTCGTGTCGTGCCTGAGAGCGCAGTCGAGAGGATCC

GTGAGTGGATGCCTTCTCCCCAGGCGGGGATGGGGGAGACCTGTAGTCAG

AGCCCCGGGCAGCACAGCCAATGCCCGTCCTTCCCCTGCAGACCGGTGC

CACCATGTGGACTCTGGTCTCCTGGGTCGCTCTGACCGCTGGCCTGGTCG

CTGGGACAAGATGCCCCGATGGACAGTTTTGCCCCGTCGCTTGCTGTCTG

GACCCAGGAGGAGCCAGCTACTCCTGCTGTCGGCCACTGCTGGATAAGTG

GCCCACCACACTGTCCCGCCACCTGGGAGGACCATGCCAGGTGGACGCAC

ACTGTTCCGCCGGACACTCTTGCATCTTCACAGTGTCTGGCACCAGCTCC

TGCTGTCCATTTCCTGAGGCAGTGGCATGCGGCGACGGACACCACTGCTG

TCCCAGGGGCTTCCACTGTAGCGCCGATGGCAGGTCCTGCTTTCAGAGAA
```

-continued

```
GCGGCAACAATTCCGTGGGCGCCATCCAGTGTCCTGACAGCCAGTTCGAA

TGCCCAGATTTTTCCACCTGCTGCGTGATGGTGGACGGCTCTTGGGGCTG

CTGTCCAATGCCACAGGCCAGCTGCTGTGAGGACAGGGTGCACTGCTGTC

CTCACGGAGCCTTCTGTGATCTGGTGCACACACGCTGCATCACCCCCACA

GGCACCCACCCTCTGGCCAAGAAGCTGCCAGCACAGAGGACCAACAGGGC

AGTGGCCCTGAGCAGCAGCGTGATGTGCCCCGACGCCAGGTCTAGATGCC

CTGATGGCAGCACCTGCTGTGAGCTGCCAAGCGGCAAGTACGGCTGCTGT

CCTATGCCAAACGCCACATGCTGTTCCGACCACCTGCACTGCTGTCCTCA

GGACACCGTGTGCGATCTGATCCAGTCTAAGTGCCTGAGCAAGGAGAATG

CCACCACAGACCTGCTGACAAAGCTGCCTGCCCACACCGTGGGCGACGTG

AAGTGTGATATGGAGGTGTCCTGCCCAGATGGCTATACATGCTGTAGGCT

GCAGTCTGGAGCATGGGGATGCTGTCCCTTCACCCAGGCCGTGTGCTGTG

AGGACCACATCCACTGCTGTCCTGCCGGCTTTACATGTGATACCCAGAAG

GGCACATGCGAGCAGGGCCCTCACCAGGTGCCATGGATGGAGAAGGCACC

AGCACACCTGTCCCTGCCCGACCCTCAGGCCCTGAAGAGAGACGTGCCTT

GTGATAACGTGTCTAGCTGCCCATCCTCTGATACATGCTGTCAGCTGACC

TCTGGCGAGTGGGGCTGCTGTCCAATCCCCGAGGCCGTGTGCTGTAGCGA

CCACCAGCACTGCTGTCCTCAGGGCTATACCTGCGTGGCAGAGGGACAGT

GCCAGAGGGGCTCCGAGATCGTGGCAGGCCTGGAGAAGATGCCAGCCAGG

AGAGCCTCTCTGAGCCACCCCAGAGACATCGGCTGTGATCAGCACACAAG

CTGCCCAGTGGGACAGACCTGCTGTCCATCCCTGGGAGGCTCTTGGGCAT

GCTGTCAGCTGCCTCACGCCGTGTGCTGTGAGGATAGGCAGCACTGCTGT

CCAGCCGGCTACACATGCAATGTGAAGGCCAGATCCTGCGAGAAGGAGGT

GGTGTCTGCCCAGCCAGCCACCTTCCTGGCACGCAGCCCTCACGTGGGCG

TGAAGGACGTGGAGTGTGGCGAGGGCCACTTTTGCCACGACAACCAGACA

TGCTGTAGGGATAATAGACAGGGCTGGGCCTGCTGTCCATATAGGCAGGG

CGTGTGCTGTGCAGATCGGCGCCACTGCTGTCCAGCAGGCTTTCGGTGCG

CAGCCAGGGGCACCAAGTGCCTGCGCAGAGAAGCCCCCGGTGGGACGCC

CCCCTGCGAGACCCCGCCCTGAGCAGCTGCTGTGAGTCGCTGGTTTAAA

CGGGACAGTACTGAAGACTCTGCAGCCCTCGGGACCCCACTCGGAGGGTG

CCCTCTGCTCAGGCCTCCCTAGCACCTCCCCCTAACCAAATTCTCCCTGG

ACCCCATTCTGAGCTCCCCATCACCATGGGAGGTGGGGCCTCAATCTAAG

GCCTTCCCTGTCAGAAGGGGGTTGTGGCAAAAGCCACATTACAAGCTGCC

ATCCCCTCCCCGTTTCAGTGGACCCTGTGGCCAGGTGCTTTTCCCTATCC

ACAGGGGTGTTTGTGTGTGTGCGCGTGTGCGTTTCGCTAGCCTCGAGAGA

TCGATCTGCCTCGACTGTGCCTTCTAGTTGCCAGCCATCTGTTGTTTGCC

CCTCCCCCGTGCCTTCCTTGACCCTGGAAGGTGCCACTCCCACTGTCCTT

TCCTAATAAAATGAGGAAATTGCATCGCATTGTCTGAGTAGGTGTCATTC

TATTCTGGGGGGTGGGGTGGGGCAGGACAGCAAGGGGGAGGATTGGGAAG

ACAATAGCAGGCATGCTGGGGACACGTGCGGACCGAGCGGCCGCAGGAAC
```

-continued
```
CCCTAGTGATGGAGTTGGCCACTCCCTCTCTGCGCGCTCGCTCGCTCACT

GAGGCCGGGCGACCAAAGGTCGCCCGACGCCCGGGCTTTGCCCGGGCGGC

CTCAGTGAGCGAGCGAGCGCGCAGCTGCCTGCAGG
```

SEQ ID NO:17 includes the following sequence elements
AAV2 ITR—residues 1-130
hSyn promoter—residues 341-788
hGHi3—residues 801-892
PGRN-GS—residues 905-2686
3' UTR—residues 2702-2985
bGH poly(A) signal—residues 3015-3222
AAV2 ITR—residues 3245-3385

Figure 19:
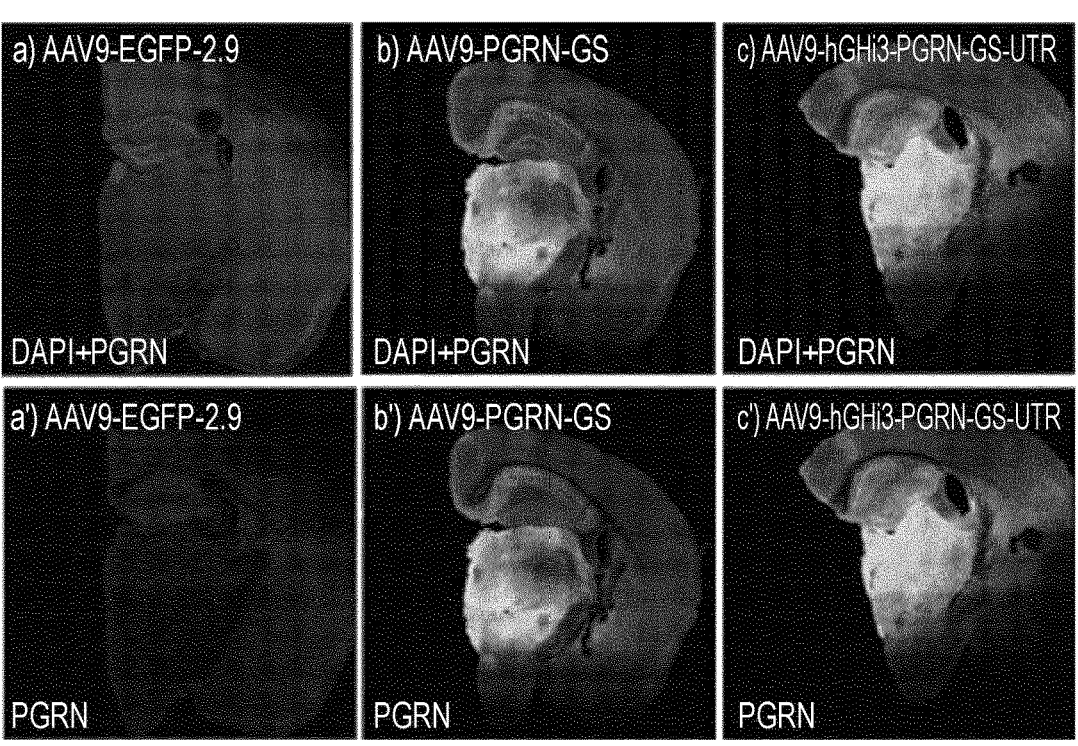
FIG. 19. Immunohistochemisty of AAV9-PGRN-GS and AAV9-hGHi3-PGRN-GS-UTR. The mice were harvested at 4 weeks after the IT injection. Free frozen tissues were sectioned at the thickness 30 uM and immunostained with human specific Goat-anti GRN antibodies (Green) for overnight. DAPI is used as counter staining (Blue). a, a') AAV-EGFP, b, b') AAV9-PGRN-GS, and c, c') AAV9-PGRN-GS-UTR.

Example 7. Widespread PGRN Expression of AAV9-Syn-PGRN-GS, AAV9-Syn-hGHi3-PGRN-GS and AAV9-Syn-hGHi3-PGRN-GS-UTR after Intra-Thalamic Injection An optimised dose of AAV particles containing the final PGRN cassettes (FIGS. 2, 5, 9, 14 and 17) were injected to mouse brain via an intra-thalamic injection to compare the efficiency of the vectors. The transduction efficacy of the AAV-PGRN viruses were tested by PGRN protein expression by ELISA and IHC. We chose an intra-thalamic route (IT) of administration over as this gives better cortical expression of EGFP and PGRNwt. The addition of the hGHi3 intronic enhancing element consistently increased the PGRN level by ~27% and the addition of the 3' UTR exonic enhancing element increased PGRN expression by ~37% (FIGS. 18b and 19). Cortical levels of PGRN were quantified by ELISA and IHC following IT injection of low (6.2E+10), middle (1.2E+11) and high (2.5E+11) dose of vector, confirming a dose-abundance effect in target tissues (FIG. 18c).

Figure 20:
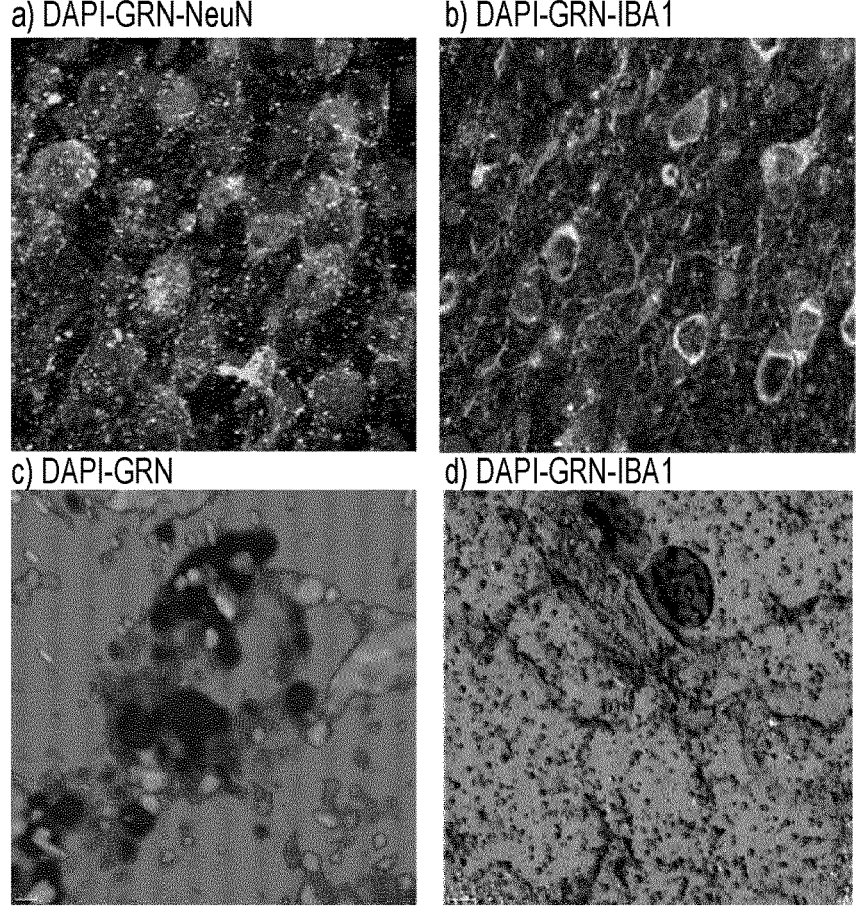
FIG. 20. High power and 3d rendered images of PGRN in mouse brain. The distribution of human PGRN was studied in the mouse cortex by immunofluorescence to determine whether PGRN is being secreted and taken up by other cells. (a) Many cortical neurons (stained red with NeuN) were positive for human PGRN (green) also seen in 3D rendered images (c). Some NeuN negative cells, indicating PGRN secreted by neurons is taken up by glia. (b) Some microglia labelled with IBA1 (red in b) showed GRN positive foci (green), also seen in 3D rendered images (d), indicating that they were able to take up PGRN secreted by neurons. Brain sections were imaged with a 2-photon microscope (a,b) or serially scanned by MR confocal. The stacked images were processed for 3D rendering by using IMAMS 8.3 to show the GRN granules. In neurons (c) and microglia (d). Scale bar=2 μM FIG. 21. Plasmid map for AAV PGRN vector. Human growth hormone intron is inserted between synapsin promoter and hPGRN. The natural sequence of hPGRN UTR was added in at the 3' end of hPGRN. The ITR to ITR were cloned in newly synthesized Kanamycin resistant backbone plasmid. A) linear form. B) circular plasmid form. AAV2 ITR=adeno-associated virus type 2 inverted terminal repeat; hSyn promoter=human synapsin promoter; hGHi3=human growth hormone intron 2; PGRN-GS=GenScript® codon-optimised human progranulin; hPGRN-3'UTR=human progranulin 3' untranslated region; bGH poly(A) signal=bovine growth hormone polyadenylation signal; f1 ori=F1 replication origin; KanR=kanamycin resistance gene.

Granular PGRN positive foci are abundant in cortical neurons (FIGS. 20a and c). Because pathological changes are seen in microglia and neurons, we sought to determine whether PGRN secreted by neurons is taken up by non-neuronal cells including microglia. PGRN under the synapsin promoter is exclusively expressed in neurons but is detected in many NeuN-negative cells (FIG. 20a) and small foci of PGRN can be detected within MA1-positive microglia (FIGS. 20b and d).

Example 8. GRN Biodistribution, Toxicology and Efficacy Using In Vivo Models An optimised dose of AAV particles containing a PGRN cassette as illustrated in FIG. 2, 5, 9, 14, or 17 is injected to non-transgenic (NTg) mice via intraparenchymal and intracerebroventricular injections to compare the efficiency of different routes of administration. The transduction efficacy of AAV-PGRN is tested by qPCR and protein expression by ELISA and IHC.

The biodistribution and toxicology of AAV-PGRN is tested in non-transgenic (NTg) and PGRN knockout (PGRN +/− and −/−) mice (see above for stereotactic surgery procedure). Additionally, the biodistribution is investigated by injection of AAV-PGRN into wild-type sheep, whose spinal cord is the same length as man and brain is twice that of the other common non-human primate model, the macaque.

Efficacy studies are performed by injecting AAV-PGRN into PGRN +/− and −/−, TDP-43 Q331K and TDP-43 Q331KxWT transgenic mice. TDP-43 transgenic mice develop either a slow (Q331K) or more rapid disease progression (TDP-43 Q331K xWT). Their behaviour is monitored using rotarod and grip strength tests to assess motor function, as well as an elevated plus maze for short-term social working memory cognitive testing. Tissues are collected and processed as described above. Animals are injected at 8 weeks of age (IT or ICV) for PGRN and TDP-43 Q331K transgenic mice or 2 weeks of age in the case of the TDP-43 Q331KxWT transgenic mice due to their aggressive phenotype. Animals are kept for 4 weeks or 6 months and behaviour is monitored on a monthly basis using the tests described above. Tissue collected from both sheep and mice is processed for IHC, ELISA, ddPCR and Western blot to measure levels of expression and protein of PGRN, to quantify PGRN mRNA levels and to determine vector genome levels. Therapeutic efficacy in TDP-43 transgenic animals is determined by quantifying insoluble TDP-43 levels and activation of microglia and astrocytes by western blot and IHC. Differences in the rate of disease progression and severity of pathology between PGRN and a control vector are statistically analysed.

Efficacy studies of AAV-PGRN in PGRN +/- and -/- mice is more difficult as the mice show only a very mild phenotype of decreased social dominance in the test tube test and no neuronal loss. The -/- mice do show an accumulation of lipofuscin and activated microglia which are readily quantifiable. Target engagement will be measured by quantifying lipofuscin reduction and levels of microglia and astroglia activation. Additionally, PGRN localisation to lysosomes will be confirmed to establish correct cellular targeting. Differences in the severity of pathology between PGRN and a control vector will be statistically analysed.

Example 9. GRN Expression Using Different AAV Capsid Serotypes

The PGRN cassette illustrated in FIG. 2, 5, 9, 14 or 17 is packaged into AAV serotype 9 and 5 to determine whether the enhanced PRGRN expression is specific to AAV9 or is relevant to other AAV serotypes. AKTA purified AAV is tested in vivo and in vitro.

Overall, the experiments described above demonstrate that the codon optimised AAV9-Syn-PGRN-GS, AAV9-Syn-hGHi3-PGRN-GS and AAV-Syn-hGHi3-PGRN-GS-UTR expression cassettes significantly increase the expression levels, transduction efficiency and cellular specificity of PGRN protein expression. These cassettes are expected to enable a reduction in vector dose given to FTD, NCL11 and ALS patients, thereby reducing the risk of toxicity and the cost of vector production.

The present application claims priority from UK patent application no. 1913974.0, filed 27 Sep. 2019, the contents of which are incorporated herein by reference. All publications mentioned in the above specification are herein incorporated by reference. Various modifications and variations of the described embodiments of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

---

The invention claimed is:

1. An adeno-associated virus (AAV) vector comprising a nucleic acid comprising:
- (i) a human growth hormone intron 3 (hGHi3) sequence, wherein the hGHi3 sequence comprises the nucleic acid sequence of SEQ ID NO: 7;
- (ii) a synapsin promoter sequence;
- (iii) a polynucleotide coding sequence encoding pro-granulin (PGRN) and comprising a 5' exonic splicing element (ESE); and
- (iv) a PGRN 3' untranslated region (UTR) sequence.

2. The AAV vector according to claim 1, wherein the AAV vector is of serotype AAV9.

3. The AAV vector according to claim 1, wherein the ESE is part of, or inserted into, a 5' flanking sequence.

4. The AAV vector according to claim 1, wherein the ESE is part of, or inserted into, a guide sequence.

5. The AAV vector according to claim 1, wherein the ESE is part of a 5' flanking sequence derived from a wild-type polynucleotide sequence.

6. The AAV vector according to claim 3, wherein the 5' flanking sequence is a 5' guide sequence derived from wild-type granulin (GRN).

7. The AAV vector according to claim 6, wherein the wild-type GRN 5' guide sequence comprises 350 to 450 base pairs.

8. The AAV vector according to claim 1, wherein the polynucleotide sequence comprises the sequence of SEQ ID NO: 2, SEQ ID NO: 3, or SEQ ID NO: 4.

9. A pharmaceutical composition or medicament comprising an AAV vector as claimed in claim 1 and one or more pharmaceutically or physiologically acceptable carriers, excipients, and/or diluents.

10. A method of treating a neurological disorder in a subject in need thereof, the method comprising administering to the subject the pharmaceutical composition or medicament of claim 9.

11. The method of claim 10, wherein the neurological disorder is frontotemporal dementia (FTD), neuronal ceroid lipofuscinosis (NCL11), amyotrophic lateral sclerosis (ALS), Huntington's disease, Parkinson's disease, or Alzheimer's disease.

12. The method of claim 10, wherein the subject: (i) is heterozygous, homozygous or compound heterozygous for GRN mutations, (ii) is suffering from sporadic neurological disease, and/or (iii) has PGRN levels below a physiologically normal level.

13. The AAV vector according to claim 1, wherein:
- a) the polynucleotide sequence is codon-optimized for expression in humans; or
- b) the ESE is upstream of the polynucleotide coding sequence.

* * * * *

SEQUENCE LISTING

<160> NUMBER OF SEQ ID NOS: 20

<210> SEQ ID NO 1
<211> LENGTH: 1782
<212> TYPE: DNA
<213> ORGANISM: Homo sapiens

<400> SEQUENCE: 1

```
atgtggaccc tggtgagctg ggtggcctta acagcagggc tggtggctgg aacgcggtgc      60
ccagatggtc agttctgccc tgtggcctgc tgcctggacc ccggaggagc cagctacagc     120
tgctgccgtc cccttctgga caaatggccc acaacactga gcaggcatct gggtggcccc     180
tgccaggttg atgcccactg ctctgccggc cactcctgca tctttaccgt ctcagggact     240
tccagttgct gccccttccc agaggccgtg gcatgcgggg atggccatca ctgctgccca     300
cggggcttcc actgcagtgc agacgggcga tcctgcttcc aaagatcagg taacaactcc     360
gtgggtgcca tccagtgccc tgatagtcag ttcgaatgcc cggacttctc cacgtgctgt     420
gttatggtcg atggctcctg ggggtgctgc cccatgcccc aggcttcctg ctgtgaagac     480
agggtgcact gctgtccgca cggtgccttc tgcgacctgg ttcacacccg ctgcatcaca     540
cccacgggca cccaccccct ggcaaagaag ctccctgccc agaggactaa cagggcagtg     600
gccttgtcca gctcggtcat gtgtccggac gcacggtccc ggtgccctga tggttctacc     660
tgctgtgagc tgcccagtgg gaagtatggc tgctgcccaa tgcccaacgc cacctgctgc     720
tccgatcacc tgcactgctg cccccaagac actgtgtgtg acctgatcca gagtaagtgc     780
ctctccaagg agaacgctac cacggacctc ctcactaagc tgcctgcgca cacagtgggg     840
gatgtgaaat gtgacatgga ggtgagctgc ccagatggct atacctgctg ccgtctacag     900
```

-continued

```
tcgggggcct ggggctgctg cccttttacc caggctgtgt gctgtgagga ccacatacac    960
tgctgtcccg cggggtttac gtgtgacacg cagaagggta cctgtgaaca ggggccccac   1020
caggtgccct ggatggagaa ggccccagct cacctcagcc tgccagaccc acaagccttg   1080
aagagagatg tcccctgtga taatgtcagc agctgtccct cctccgatac ctgctgccaa   1140
ctcacgtctg gggagtgggg ctgctgtcca atcccagagg ctgtctgctg ctcggaccac   1200
cagcactgct gcccccaggg ctacacgtgt gtagctgagg ggcagtgtca gcgaggaagc   1260
gagatcgtgg ctggactgga gaagatgcct gcccgccggg cttccttatc ccaccccaga   1320
gacatcggct gtgaccagca caccagctgc ccggtggggc agacctgctg cccgagcctg   1380
ggtgggagct gggcctgctg ccagttgccc catgctgtgt gctgcgagga tcgccagcac   1440
tgctgcccgg ctggctacac ctgcaacgtg aaggctcgat cctgcgagaa ggaagtggtc   1500
tctgcccagc ctgccacctt cctggcccgt agccctcacg tgggtgtgaa ggacgtggag   1560 tgtgggaag gacacttctg ccatgataac cagacctgct gccgagacaa ccgacagggc   1620
tgggcctgct gtccctaccg ccagggcgtc tgttgtgctg atcggcgcca ctgctgtcct   1680
gctggcttcc gctgcgcagc caggggtacc aagtgtttgc gcaggaggc cccgcgctgg   1740 gacgccctt tgagggaccc agccttgaga cagctgctgt ga                       1782
```

<210> SEQ ID NO 2
<211> LENGTH: 1782
<212> TYPE: DNA
<213> ORGANISM: Artificial Sequence
<220> FEATURE:
<223> OTHER INFORMATION: Candidate I (PGRN-IDT) artificial
      codon-optimised PGRN DNA coding sequence

<400> SEQUENCE: 2

```
atgtggactc tcgtgagttg ggtcgccctt actgctggac ttgtggctgg cacaaggtgc     60
ccggacgggc agttctgccc tgtggcatgt tgccttgatc ccggtggcgc aagctactca    120
tgctgtaggc cactgctgga caaatggcct acaaccctct cacgacacct cggcggccca    180
tgtcaagtag atgcacattg ttccgccggt catagctgta tttcaccgt aagtggcacc     240 agctcttgtt gcccttccc tgaggccgtt gcgtgtggtg atggacacca ttgttgcccc     300
aggggctttc actgctccgc tgatgggcga tcttgctttc agcggagtgg taacaactcc     360
gttggagcta ttcagtgccc tgactcccaa ttcgaatgtc cggatttctc aacgtgttgt     420
gtgatggttg acggctcttg gggttgctgc ccaatgcctc aggcaagttg ttgcgaggac     480
cgagtccatt gttgtccaca tggtgctttc tgcgatctcg tccacacccg atgcattaca     540
ccaacaggga cgcacccgtt ggcaaagaaa ctccctgcgc aaagaactaa tcgcgcagtt     600
gcgctttcta gcagcgttat gtgcccggat gcgcggagtc gctgtcctga tggttcaact     660
tgttgcgaac tcccgtcagg caaatacgga tgctgccta tgccaaatgc gacatgttgc     720
tcagaccatc ttcattgttg tccccaggat accgtatgtg acttgattca gagcaagtgt     780
ttgtccaaag agaacgcgac cacggatctt ctcaccaagc tcccggcaca cacggtcggc     840
gatgtgaaat gtgacatgga ggtctcctgc ccagatggct acacgtgctg tcggttgcag     900
tcaggggcct ggggctgttg tccattcacc caggctgttt gctgtgaaga tcatatccat     960
tgttgtccag cgggatttac gtgtgacact caaaaaggca catgcgagca aggaccacac    1020
caggttcctt ggatggagaa ggccccagct catctgtctc ttcctgatcc ccaggcgctc    1080
aagagagacg ttccttgcga caacgtttcc tcatgtccct catctgacac atgctgtcag    1140
```

-continued

```
ttgacgagcg gtgagtgggg atgctgtcca atccctgagg ctgtctgctg ctcagatcac      1200
caacattgct gcccacaggg ctatacatgc gtcgcgcgaag ggcaatgcca acgggggagt      1260
gaaatagtcg ccggcctgga gaaaatgccc gcgcgcaggg cttcattgtc tcatccccga      1320
gacattggct gcgaccagca tacgtcctgc cctgtaggcc aaacttgttg ccctccctg      1380 ggtggatctt gggcatgttg tcagcttccc catgctgtgt gttgtgagga tcgacaacat      1440
tgttgccctg ccgggtacac ttgcaatgta aaggccagga gctgcgagaa ggaagtagtt      1500
tcagcacagc ccgctacgtt tttggctagg tcaccacacg tcggggtaaa agacgttgag      1560
tgcggcgagg gtcatttctg ccacgataac cagacctgtt gcagagataa tagacaaggg      1620
tgggcgtgct gtccctatcg acaaggagtg tgctgtgccg atcggcgcca ttgctgcccg      1680
gcgggattcc gatgcgcagc aagaggcact aaatgtttgc gccgagaggc cccacgctgg      1740
gatgccccgc tccgggaccc cgctcttcgg cagttgctgt ga      1782
```

```
<210> SEQ ID NO 3
<211> LENGTH: 1782
<212> TYPE: DNA
<213> ORGANISM: Artificial Sequence
<220> FEATURE:
<223> OTHER INFORMATION: Candidate II (PGRN-GA) artificial
      codon-optimised PGRN DNA coding sequence

<400> SEQUENCE: 3
atgtggacac tggtgtcttg ggttgccctg acagctggac tggtggccgg aaccagatgt       60
cctgatggcc agttttgccc cgtggcctgt tgtcttgatc ctggcggagc cagctacagc      120
tgctgcagac ctctgctgga taagtggccc accacactga gcagacacct cggaggacct      180
tgtcaggtgg acgcccactg ttctgccggc cacagctgta tctttaccgt gtctggcacc      240
tccagctgct gtccatttcc tgaggctgtg gcctgcggag atggccacca ctgttgtcct      300
agaggcttcc actgtagcgc cgacggcaga agctgctttc agagaagcgg caacaatagc      360
gtgggcgcca tccagtgtcc tgactctcag ttcgaatgcc ccgacttcag cacctgttgc      420
gtgatggtgg atggcagctg gggctgttgt ccaatgcctc aggcttcctg ctgcgaggac      480
agagtgcact gttgccctca cggcgccttt tgcgatctgg tgcacacccg gtgcatcacc      540
ccaacaggca cacatcctct ggccaagaag ctgcctgctc agcggaccaa tagagccgtg      600
gctctgagca gcagcgtgat gtgccctgac gccagatcta gatgccccga tggctccaca      660
tgttgcgaac tgcccagcgg caaatacggc tgctgcccca tgcctaacgc cacatgctgt      720
agcgaccatc ttcactgctg cccacaagat accgtgtgcg acctgatcca gagcaagtgc      780
ctgagcaaag agaacgccac caccgacctg ctgaccaaac tgccagctca caccgtgggc      840
gacgtgaagt gcgacatgga agtgtcttgc cccgacggct atacctgctg tagactgcaa      900
tctggcgcct ggggatgctg ccctttttaca caggctgtgt gttgcgagga ccacatccat      960
tgctgccctg ccggcttcac ctgtgacaca cagaaaggca catgcgagca gggccctcat     1020
caggtgccat ggatggaaaa agccctgct cacctgagcc tgcctgatcc tcaagctctg     1080
aagagggacg tgccctgcga caatgtgtct agctgcccta gcagcgacac atgctgccag     1140
ctgacatctg gcgaatgggg ctgctgtcct ataccagagg ccgtgtgttg tagcgatcac     1200
cagcactgct gtccccaagg ctacacctgt gtggccgaag ccaatgtca acggggctct     1260 gaaatcgtgg ccggcctgga aaaaatgccc gccagaaggg cctctctgtc tcaccctaga     1320
gacatcggct gcgaccagca cacatcttgt cctgtgggcc agacctgttg tccctctctt     1380
```

-continued

```
ggtggatctt gggcctgctg tcagctgcct catgccgtgt gctgcgaaga tagacaacat    1440
tgctgtcccg ctggctacac atgcaacgtg aaggccagat cctgcgagaa agaagtggtg    1500
tctgcccagc ctgccacctt cctggctaga agtcctcacg tgggcgtgaa ggatgtggaa    1560
tgtggcgagg gccacttctg ccacgacaat cagacatgct gcagagacaa ccggcaaggc    1620
tgggcttgct gcccatatag acagggcgtg tgctgtgccg acagaaggca ctgttgtcca    1680
gccggcttta gatgtgccgc caggggcaca aagtgtctga aagagaagc ccctagatgg    1740 gacgcccctc tgagagatcc tgctctgaga cagctgctct ga                       1782
```

<210> SEQ ID NO 4
<211> LENGTH: 1782
<212> TYPE: DNA
<213> ORGANISM: Artificial Sequence
<220> FEATURE:
<223> OTHER INFORMATION: Candidate III (PGRN-GS) artificial
      codon-optimised PGRN DNA coding sequence

<400> SEQUENCE: 4

```
atgtggactc tggtctcctg ggtcgctctg accgctggcc tggtcgctgg gacaagatgc      60
cccgatggac agttttgccc cgtcgcttgc tgtctggacc caggaggagc cagctactcc     120
tgctgtcggc cactgctgga taagtggccc accacactgt cccgccacct gggaggacca     180
tgccaggtgg acgcacactg ttccgccgga cactcttgca tcttcacagt gtctggcacc     240
agctcctgct gtccatttcc tgaggcagtg gcatgcggcg acggacacca ctgctgtccc     300
aggggcttcc actgtagcgc cgatggcagg tcctgctttc agagaagcgg caacaattcc     360
gtgggcgcca tccagtgtcc tgacagccag ttcgaatgcc agattttttc cacctgctgc     420
gtgatggtgg acgctcttg gggctgctgt ccaatgccac aggccagctg ctgtgaggac     480
agggtgcact gctgtcctca cggagccttc tgtgatctgg tgcacacacg ctgcatcacc     540
cccacaggca cccaccctct ggccaagaag ctgccagcac agaggaccaa cagggcagtg     600
gccctgagca gcagcgtgat gtgcccgac gccaggtcta gatgccctga tggcagcacc     660
tgctgtgagc tgccaagcgg caagtacggc tgctgtccta tgccaaacgc cacatgctgt     720
tccgaccacc tgcactgctg tcctcaggac accgtgtgcg atctgatcca gtctaagtgc     780
ctgagcaagg agaatgccac cacagacctg ctgacaaagc tgcctgccca ccgtgtgggc     840
gacgtgaagt gtgatatgga ggtgtcctgc ccagatggct atacatgctg taggctgcag     900
tctggagcat ggggatgctg tcccttcacc caggccgtgt gctgtgagga ccacatccac     960
tgctgtcctg ccggctttac atgtgatacc cagaagggca catgcgagca gggccctcac    1020
caggtgccat ggatggagaa ggcaccagca cacctgtccc tgcccgaccc tcaggccctg    1080
aagagagacg tgccttgtga taacgtgtct agctgcccat cctctgatac atgctgtcag    1140
ctgacctctg gcgagtgggg ctgctgtcca atccccgagg ccgtgtgctg tagcgaccac    1200
cagcactgct gtcctcaggg ctatacctgc gtggcagagg acagtgcca gagggctcc    1260 gagatcgtgg caggcctgga gaagatgcca gccaggagag cctctctgag ccaccccaga    1320
gacatcggct gtgatcagca cacaagctgc ccagtgggac agacctgctg tccatccctg    1380
ggaggctctt gggcatgctg tcagctgcct cacgccgtgt gctgtgagga taggcagcac    1440
tgctgtccag ccggctacac atgcaatgtg aaggccagat cctgcgagaa ggaggtggtg    1500
tctgcccagc agccaccctt cctggcacgc agccctcacg tgggcgtgaa ggacgtggag    1560
tgtggcgagg gccacttttg ccacgacaac cagacatgct gtagggataa tagacagggc    1620
```

-continued

```
tgggcctgct gtccatatag gcagggcgtg tgctgtgcag atcggcgcca ctgctgtcca    1680
gcaggctttc ggtgcgcagc caggggcacc aagtgcctgc gcagagaagc cccccggtgg    1740 gacgccccc tgcgagaccc cgccctgaga cagctgctgt ga                        1782
```

<210> SEQ ID NO 5
<211> LENGTH: 260
<212> TYPE: DNA
<213> ORGANISM: Homo sapiens

<400> SEQUENCE: 5

```
gtaagcgccc ctaaaatccc tttgggcaca atgtgtcctg aggggagagg cagcgacctg      60
tagatgggac gggggcacta accctcaggt ttggggcttc tgaatgtgag tatcgccatg     120
taagcccagt atttggccaa tctcagaaag ctcctggtcc ctggagggat ggagagagaa     180
aaacaaacag ctcctggagc agggagagtg ctggcctctt gctctccggc tccctctgtt     240
gccctctggt ttctccccag                                                 260
```

<210> SEQ ID NO 6
<211> LENGTH: 209
<212> TYPE: DNA
<213> ORGANISM: Homo sapiens

<400> SEQUENCE: 6

```
gtaagctctt ggggaatggg tgcgcatcag gggtggcagg aaggggtgac tttcccccgc      60
tgggaaataa gaggaggaga ctaaggagct cagggttttt cccgaagcga aaatgcaggc     120
agatgagcac acgctgagtg aggttcccag aaaagtaaca atgggagctg gtctccagcg     180
tagaccttgg tgggcggtcc ttctcctag                                       209
```

<210> SEQ ID NO 7
<211> LENGTH: 92
<212> TYPE: DNA
<213> ORGANISM: Homo sapiens

<400> SEQUENCE: 7

```
gtgagtggat gccttctccc caggcgggga tgggggagac ctgtagtcag agcccccggg      60
cagcacagcc aatgcccgtc cttcccctgc ag                                   92
```

<210> SEQ ID NO 8
<211> LENGTH: 253
<212> TYPE: DNA
<213> ORGANISM: Homo sapiens

<400> SEQUENCE: 8

```
gtgagggtgg cgccaggggt ccccaatcct ggagccccac tgactttgag agctgtgtta      60
gagaaacact gctgccctct ttttagcagt caggccctga cccaagagaa ctcaccttat     120
tcttcatttc ccctcgtgaa tcctccaggc ctttctctac accctgaagg ggagggagga     180
aaatgaatga atgagaaagg gagggaacag tacccaagcg cttggcctct ccttctcttc     240
cttcactttg cag                                                        253
```

<210> SEQ ID NO 9
<211> LENGTH: 78
<212> TYPE: DNA
<213> ORGANISM: Homo sapiens

<400> SEQUENCE: 9

-continued

```
atggctacag gctcccggac gtccctgctc ctggcttttg gcctgctctg cctgccctgg          60
cttcaagagg gcagtgcc                                                        78

<210> SEQ ID NO 10
<211> LENGTH: 26
<212> TYPE: PRT
<213> ORGANISM: Homo sapiens

<400> SEQUENCE: 10

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 11
<211> LENGTH: 202
<212> TYPE: DNA
<213> ORGANISM: Homo sapiens

<400> SEQUENCE: 11
cgacacccgg cgctccatta aatagccgta gacggaactt cgcctttctc tcggccttag          60
cgccattttt ttgggtgagt gtttttttggt tcctgcgttg ggattccgtg tacaatccat        120
agacatctga cctcggcact tagcatcatc acagcaaact aactgtagcc tttctctctt        180
tccctgtaga aacctctgcg cc                                                  202

<210> SEQ ID NO 12
<211> LENGTH: 145
<212> TYPE: DNA
<213> ORGANISM: Homo sapiens

<400> SEQUENCE: 12 tttcccctc gcttggttct gccctgctc ccctgcaca ggcctcacag tgcgtctggc           60
cggcgcttta tagctgcagc ctgggcggct ccgctagctg tttttcgtct tccctaggct        120
atttctgccg ggcgctccgc gaagg                                              145

<210> SEQ ID NO 13
<211> LENGTH: 93
<212> TYPE: DNA
<213> ORGANISM: Homo sapiens

<400> SEQUENCE: 13
actgcccgga aacggaagtc tcgttctttt tcgtcctttt ccccggttgc tgcttgctgt         60
gagtgtctct agggtgatac gtgggtgaga aag                                      93

<210> SEQ ID NO 14
<211> LENGTH: 284
<212> TYPE: DNA
<213> ORGANISM: Homo sapiens

<400> SEQUENCE: 14
gggacagtac tgaagactct gcagccctcg gacccccact cggagggtgc cctctgctca         60
ggcctcccta gcacctcccc ctaaccaaat tctccctgga ccccattctg agctccccat        120
caccatggga ggtggggcct caatctaagg ccttccctgt cagaagggg ttgtggcaaa        180 agccacatta caagctgcca tcccctcccc gtttcagtgg accctgtggc caggtgcttt        240
tccctatcca caggggtgtt tgtgtgtgtg cgcgtgtgcg tttc                         284
```

-continued

```
<210> SEQ ID NO 15
<211> LENGTH: 448
<212> TYPE: DNA
<213> ORGANISM: Homo sapiens

<400> SEQUENCE: 15
agtgcaagtg ggttttagga ccaggatgag gcggggtggg ggtgcctacc tgacgaccga      60
ccccgaccca ctggacaagc acccaacccc cattccccaa attgcgcatc ccctatcaga     120 gaggggggagg ggaaacagga tgcggcgagg cgcgtgcgca ctgccagctt cagcaccgcg     180
gacagtgcct tcgcccccgc ctggcggcgc gcgccaccgc cgcctcagca ctgaaggcgc     240
gctgacgtca ctcgccggtc ccccgcaaac tccccttccc ggccaccttg gtcgcgtccg     300
cgccgccgcc ggcccagccg gaccgcacca cgcgaggcgc gagatagggg ggcacgggcg     360
cgaccatctg cgctgcggcg ccggcgactc agcgctgcct cagtctgcgg tgggcagcgg     420
aggagtcgtg tcgtgcctga gagcgcag                                       448

<210> SEQ ID NO 16
<211> LENGTH: 593
<212> TYPE: PRT
<213> ORGANISM: Homo sapiens

<400> SEQUENCE: 16

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
            115                 120                 125

Ser Gln Phe Glu Cys Pro Asp Phe Ser Thr Cys Cys Val Met Val Asp
        130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
            195                 200                 205

Pro Asp Ala Arg Ser Arg Cys Pro Asp Gly Ser Thr Cys Cys Glu Leu
        210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255
```

-continued

```
Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
            275                 280                 285

Ser Cys Pro Asp Gly Tyr Thr Cys Cys Arg Leu Gln Ser Gly Ala Trp
            290                 295                 300

Gly Cys Cys Pro Phe Thr Gln Ala Val Cys Cys Glu Asp His Ile His
305                 310                 315                 320

Cys Cys Pro Ala Gly Phe Thr Cys Asp Thr Gln Lys Gly Thr Cys Glu
                325                 330                 335

Gln Gly Pro His Gln Val Pro Trp Met Glu Lys Ala Pro Ala His Leu
            340                 345                 350

Ser Leu Pro Asp Pro Gln Ala Leu Lys Arg Asp Val Pro Cys Asp Asn
            355                 360                 365

Val Ser Ser Cys Pro Ser Ser Asp Thr Cys Cys Gln Leu Thr Ser Gly
            370                 375                 380

Glu Trp Gly Cys Cys Pro Ile Pro Glu Ala Val Cys Cys Ser Asp His
385                 390                 395                 400

Gln His Cys Cys Pro Gln Gly Tyr Thr Cys Val Ala Glu Gly Gln Cys
                405                 410                 415

Gln Arg Gly Ser Glu Ile Val Ala Gly Leu Glu Lys Met Pro Ala Arg
            420                 425                 430

Arg Ala Ser Leu Ser His Pro Arg Asp Ile Gly Cys Asp Gln His Thr
            435                 440                 445

Ser Cys Pro Val Gly Gln Thr Cys Cys Pro Ser Leu Gly Gly Ser Trp
            450                 455                 460

Ala Cys Cys Gln Leu Pro His Ala Val Cys Cys Glu Asp Arg Gln His
465                 470                 475                 480

Cys Cys Pro Ala Gly Tyr Thr Cys Asn Val Lys Ala Arg Ser Cys Glu
                485                 490                 495

Lys Glu Val Val Ser Ala Gln Pro Ala Thr Phe Leu Ala Arg Ser Pro
            500                 505                 510

His Val Gly Val Lys Asp Val Glu Cys Gly Glu Gly His Phe Cys His
            515                 520                 525

Asp Asn Gln Thr Cys Cys Arg Asp Asn Arg Gln Gly Trp Ala Cys Cys
            530                 535                 540

Pro Tyr Arg Gln Gly Val Cys Cys Ala Asp Arg Arg His Cys Cys Pro
545                 550                 555                 560

Ala Gly Phe Arg Cys Ala Ala Arg Gly Thr Lys Cys Leu Arg Arg Glu
                565                 570                 575

Ala Pro Arg Trp Asp Ala Pro Leu Arg Asp Pro Ala Leu Arg Gln Leu
            580                 585                 590

Leu
```

```
<210> SEQ ID NO 17
<211> LENGTH: 3385
<212> TYPE: DNA
<213> ORGANISM: Artificial Sequence
<220> FEATURE:
<223> OTHER INFORMATION: Syn-hGHi3-PGRN-GS-UTR DNA sequence from ITR to
      ITR

<400> SEQUENCE: 17
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact      120
```

-continued

```
aggggttcct gcggccgcac gcgttgcaaa gatggataaa gttttaaaca gagaggaatc    180
tttgcagcta atggaccttc taggtcttga aaggagtggg aattggctcc ggtgcccgtc    240
agtgggcaga gcgcacatcg cccacagtcc ccgagaagtt gggggagggg gtcggcagca    300
aatggttaat taatctagac tgcagagggc cctgcgtatg agtgcaagtg ggttttagga    360
ccaggatgag gcggggtggg ggtgcctacc tgacgaccga ccccgacccca ctggacaagc    420 acccaacccc cattccccaa attgcgcatc ccctatcaga gagggggagg ggaaacagga    480
tgcggcgagg cgcgtgcgca ctgccagctt cagcaccgcg gacagtgcct cgcccccgc    540 ctggcggcgc gcgccaccgc cgcctcagca ctgaaggcgc gctgacgtca ctcgccggtc    600
ccccgcaaac tcccctttccc ggccaccttg gtcgcgtccg cgccgccgcc ggcccagccg    660
gaccgcacca cgcgaggcgc gagatagggg ggcacgggcg cgaccatctg cgctgcggcg    720
ccggcgactc agcgctgcct cagtctgcgg tgggcagcgg aggagtcgtg tcgtgcctga    780
gagcgcagtc gagaggatcc gtgagtggat gccttctccc caggcgggga tgggggagac    840
ctgtagtcag agccccgggg cagcacagcc aatgcccgtc cttcccctgc agaccggtgc    900
caccatgtgg actctggtct cctgggtcgc tctgaccgct ggcctggtcg ctgggacaag    960
atgccccgat ggacagtttt gccccgtcgc ttgctgtctg acccaggag gagccagcta    1020 ctcctgctgt cggccactgc tggataagtg gcccaccaca ctgtcccgcc acctgggagg    1080
accatgccag gtggacgcac actgttccgc cggacactct tgcatcttca cagtgtctgg    1140
caccagctcc tgctgtccat ttcctgaggc agtggcatgc ggcgacggac accactgctg    1200
tcccaggggc ttccactgta cgccgatgg caggtcctgc tttcagagaa gcggcaacaa    1260
ttccgtgggc gccatccagt gtcctgacag ccagttcgaa tgcccagatt tttccacctg    1320
ctgcgtgatg gtggacggct cttgggggctg ctgtccaatg ccacaggcca gctgctgtga    1380
ggacagggtg cactgctgtc ctcacggagc cttctgtgat ctggtgcaca cacgctgcat    1440
cacccccaca ggcacccacc ctctggccaa gaagctgcca gcacagagga ccaacagggc    1500
agtggccctg agcagcagcg tgatgtgccc cgacgccagg tctagatgcc ctgatggcag    1560
cacctgctgt gagctgccaa gcggcaagta cggctgctgt cctatgccaa cgccacatg    1620 ctgttccgac cacctgcact gctgtcctca ggacaccgtg tgcgatctga tccagtctaa    1680
gtgcctgagc aaggagaatg ccaccacaga cctgctgaca aagctgcctg cccacaccgt    1740
gggcgacgtg aagtgtgata tggaggtgtc ctgcccagat ggctatacat gctgtaggct    1800
gcagtctgga gcatggggat gctgtccctt cacccaggcc gtgtgctgtg aggaccacat    1860
ccactgctgt cctgccggct ttacatgtga tacccagaag ggcacatgcg agcagggccc    1920
tcaccaggtg ccatggatgg agaaggcacc agcacacctg tccctgcccg accctcaggc    1980
cctgaagaga gacgtgcctt gtgataacgt gtctagctgc ccatcctctg atacatgctg    2040
tcagctgacc tctggcgagt ggggctgctg tccaatcccc gaggccgtgt gctgtagcga    2100
ccaccagcac tgctgtcctc agggctatac ctgcgtggca gagggacagt gccagagggg    2160
ctccgagatc gtggcaggcc tggagaagat gccagccagg agagcctctc tgagccaccc    2220
cagagacatc ggctgtgatc agcacacaag ctgcccagtg ggacagacct gctgtccatc    2280
cctgggaggc tcttgggcat gctgtcagct gcctcacgcc gtgtgctgtg aggataggca    2340
gcactgctgt ccagccggct acacatgcaa tgtgaaggcc agatcctgcg agaaggaggt    2400
ggtgtctgcc cagccagcca ccttcctggc acgcagccct cacgtgggcg tgaaggacgt    2460
```

-continued

```
ggagtgtggc gagggccact tttgccacga caaccagaca tgctgtaggg ataatagaca    2520
gggctgggcc tgctgtccat ataggcaggg cgtgtgctgt gcagatcggc gccactgctg    2580
tccagcaggc tttcggtgcg cagccagggg caccaagtgc ctgcgcagag aagccccccg    2640
gtgggacgcc cccctgcgag accccgccct gagacagctg ctgtgagtcg ctggtttaaa    2700
cgggacagta ctgaagactc tgcagccctc gggaccccac tcggagggtg ccctctgctc    2760
aggcctccct agcacctccc cctaaccaaa ttctccctgg accccattct gagctcccca    2820
tcaccatggg aggtggggcc tcaatctaag gccttccctg tcagaagggg gttgtggcaa    2880
aagccacatt acaagctgcc atccctccc cgtttcagtg gaccctgtgg ccaggtgctt    2940
ttccctatcc acaggggtgt ttgtgtgtgt gcgcgtgtgc gtttcgctag cctcgagaga    3000
tcgatctgcc tcgactgtgc cttctagttg ccagccatct gttgtttgcc cctccccgt    3060 gccttccttg accctggaag gtgccactcc cactgtcctt tcctaataaa atgaggaaat    3120
tgcatcgcat tgtctgagta ggtgtcattc tattctgggg ggtggggtgg ggcaggacag    3180 caaggggag gattgggaag acaatagcag gcatgctggg gacacgtgcg gaccgagcgg    3240
ccgcaggaac ccctagtgat ggagttggcc actccctctc tgcgcgctcg ctcgctcact    3300
gaggccgggc gaccaaaggt cgcccgacgc ccgggctttg cccgggcggc ctcagtgagc    3360
gagcgagcgc gcagctgcct gcagg                                         3385

<210> SEQ ID NO 18
<211> LENGTH: 52
<212> TYPE: DNA
<213> ORGANISM: Artificial Sequence
<220> FEATURE:
<223> OTHER INFORMATION: Bovine growth hormone (bGH) poly(A) signal

<400> SEQUENCE: 18
gtcctttcct aataaaatga ggaaattgca tcgcattgtc tgagtaggtg tc           52

<210> SEQ ID NO 19
<211> LENGTH: 130
<212> TYPE: DNA
<213> ORGANISM: Artificial Sequence
<220> FEATURE:
<223> OTHER INFORMATION: 5' AAV2 UTR sequence

<400> SEQUENCE: 19
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct                                                          130

<210> SEQ ID NO 20
<211> LENGTH: 141
<212> TYPE: DNA
<213> ORGANISM: Artificial Sequence
<220> FEATURE:
<223> OTHER INFORMATION: 3' AAV2 UTR sequence

<400> SEQUENCE: 20
aggaacccct agtgatggag ttggccactc cctctctgcg cgctcgctcg ctcactgagg    60
ccgggcgacc aaaggtcgcc cgacgcccgg gctttgcccg gcggcctca gtgagcgagc   120 gagcgcgcag ctgcctgcag g                                             141
```